US009657267B2

(12) United States Patent
Izadyar et al.

(10) Patent No.: US 9,657,267 B2
(45) Date of Patent: May 23, 2017

(54) EX HOST MATURATION OF GERMLINE STEM CELLS

(75) Inventors: Fariborz Izadyar, Irvine, CA (US); Johnny Yung-Chiong Chow, Taipei (TW); Constance Yuen, Newport Coast, CA (US)

(73) Assignee: PrimeGen Biotech LLC, Irvine, CA (US)

( * ) Notice: Subject to any disclaimer, the term of this patent is extended or adjusted under 35 U.S.C. 154(b) by 1177 days.

(21) Appl. No.: 12/940,894

(22) Filed: Nov. 5, 2010

(65) Prior Publication Data

US 2012/0083034 A1    Apr. 5, 2012

Related U.S. Application Data

(60) Provisional application No. 61/258,535, filed on Nov. 5, 2009.

(51) Int. Cl.
*C12N 5/075*        (2010.01)
*C12N 5/076*        (2010.01)

(52) U.S. Cl.
CPC ........... *C12N 5/0609* (2013.01); *C12N 5/061* (2013.01); *C12N 2500/25* (2013.01); *C12N 2500/30* (2013.01); *C12N 2500/84* (2013.01); *C12N 2500/90* (2013.01); *C12N 2501/06* (2013.01); *C12N 2501/10* (2013.01); *C12N 2501/11* (2013.01); *C12N 2501/119* (2013.01); *C12N 2501/125* (2013.01); *C12N 2501/13* (2013.01); *C12N 2501/15* (2013.01); *C12N 2501/235* (2013.01); *C12N 2501/31* (2013.01); *C12N 2501/385* (2013.01); *C12N 2501/998* (2013.01); *C12N 2509/00* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| 6,090,622 | A | 7/2000 | Gerhart et al. |
| 6,872,569 | B2 | 3/2005 | Lee |
| 7,087,371 | B2 | 8/2006 | Dobrinski et al. |
| 2003/0215942 | A1 | 11/2003 | Chow et al. |
| 2004/0091936 | A1 | 5/2004 | West |
| 2004/0258673 | A1 | 12/2004 | Hirose et al. |
| 2006/0010508 | A1 | 1/2006 | Tilly et al. |
| 2006/0078993 | A1 | 4/2006 | Phan et al. |
| 2007/0011756 | A1 | 1/2007 | Shinohara et al. |
| 2007/0020759 | A1 | 1/2007 | Sayre et al. |
| 2008/0044395 | A1* | 2/2008 | Kim et al. ............... 424/93.21 |
| 2008/0102521 | A1 | 5/2008 | Sugaya et al. |
| 2008/0132803 | A1 | 6/2008 | Friedlander |
| 2008/0189045 | A1 | 8/2008 | Moore |
| 2008/0227197 | A1 | 9/2008 | Chow et al. |
| 2009/0018868 | A1 | 1/2009 | Chang et al. |
| 2009/0104593 | A1* | 4/2009 | Werkmeister et al. ........ 435/1.1 |
| 2009/0126285 | A1 | 5/2009 | Suh et al. |
| 2009/0138354 | A1 | 5/2009 | Zech |
| 2009/0170059 | A1 | 7/2009 | Klingemann |
| 2010/0267134 | A1* | 10/2010 | Pera et al. .................... 435/366 |
| 2012/0009156 | A1 | 1/2012 | Izadyar |

FOREIGN PATENT DOCUMENTS

| CN | 1385523 A | 12/2002 |
| CN | 1800371 A | 7/2006 |
| CN | 101062058 A | 10/2007 |
| CN | 101429492 B | 10/2010 |
| CN | 100999722 B | 8/2011 |
| EP | 1741776 A | 1/2007 |
| WO | 2005/017184 A2 | 2/2005 |
| WO | 2005/100551 A1 | 10/2005 |
| WO | 2007/047979 A2 | 4/2007 |
| WO | 2007/051625 A2 | 5/2007 |
| WO | 2007/115216 A1 | 10/2007 |
| WO | 2011/057123 | 5/2011 |

OTHER PUBLICATIONS

Goosens et al. "Spermatogonial survival in long-term human prepubertal xenografts." Fertility and Sterility, vol. 90, No. 5m Nov. 1, 2008, pp. 2019-2022.
Sofikitis et al. "Efforts to create an artificial testis: culture systems of male germ cells under biochemical conditions resembling the seminiferous tubular biochemical environment" Human Reproduction Update, vol. 11, No. 3, May 2005, pp. 229-259.
Vanhoutte et al. "Assessment of a new in vitro maturation system for mouse and human cumulus-enclosed oocytes: three-dimensional prematuration culture in the presence of a phosphodiesterase 3-inhibitor." Human Reproduction, vol. 24, No. 8, Aug. 2009, pp. 1946-1959.
Wyns et al. "Spermatogonial survival after cryopreservation and short-term orthotopic immature human cryptorchid testicular tissue grafting to immunodeficient mice." Human Reproduction, vol. 22, No. 6, Jun. 2007, pp. 1603-1611.
Wyns et al. "Long-term spermatogonial survival in cryopreserved and xenografted immature human testicular tissue." Human Reproduction, vol. 23, No. 11, Nov. 2008, pp. 2404-2414.
International Search Report, PCT/US2010/055711.
Brook et al. "Isolation of germ cells from human testicular tissue for low temperature storage and autotransplantation." Fertility and Sterility, vol. 75, No. 2, Feb. 2001.
Brydoy et al. "Paternity Following Treatment for Testicular Cancer." Journal of the National Cancer Institute, vol. 97, No. 21, Nov. 2, 2005.
Conrad S et al. "Generation of pluripotent stem cells from adult human testis," Nature 456:344-51, 2008.
Grazul-Bilska et al. "Morphology and function of cryopreserved whole ovine ovaries after heterotopic autotransplantation." Reproductve Biology and Endocrinology 2008, 6:16.
Izadyar et al. "Generation of multipotent cell lines from a distinct population of male germ line stem cells." Reproduction (2008) 135; 771-784.

(Continued)

*Primary Examiner* — Sharmila G. Landau
*Assistant Examiner* — Paul D. Pyla
(74) *Attorney, Agent, or Firm* — K&L Gates LLP; Louis C. Cullman; Michelle Glasky Bergman

(57) ABSTRACT

Methods are provided for the ex host maturation of immature germline cells into haploid gametes for restoration of fertility in patients in need thereof.

7 Claims, 63 Drawing Sheets

(56) References Cited

OTHER PUBLICATIONS

Jahnukainen et al. "Clinical Poteintial and Putative Risks of Fertility Preservation in Children Utilizing Gonadal Tissue of Germline Stem Cells." Pediatric Research, vol. 59, No. 4, Pt. 2, 2006.
Kanatsu-Shinohara et al. "Restoration of fertility in infertile mice by transplantation of cryopreserved male germline stem cells." Human Reproduction, vol. 18, No. 12, pp. 2660-2667, 2003.
Kanatsu-Shinohara et al. "Long-Term Proliferation in Culture and Germline Transmission of Mouse Male Germline Stem Cells," Biology of Reproduction, Society for the Study of Reproduction, Champaign, IL, vol. 69, No. 2, Apr. 16, 2003, pp. 612-616.
Kanatsu-Shinohara et al. "The Germ of Pluripotency," Mature Biotechnology, Nature Publishing Group, New York, NY, vol. 24, No. 6, Jun. 1, 2006, pp. 663-664.
Keros et al. "Optimizing cryopreservation of human testicular tissue: comparison of protocols with glycerol, propanediol and dimethylsulphoxide as cryoprotectants." Human Reproduction, vol. 20, No. 6, pp. 1676-1687, 2005.
Kerr CL et al. "Pluripotent stem cells from germ cells," Methods in Enzymology 419:400-426, 2006.
Kvist et al. "Cryopreservation of intact testicular tissue from boys with cryptochidism." Human Reproduction, vol. 21, No. 2, pp. 484-491, 2006.
Maki et al. "Phenotypic and molecular characterization of spermatogonial stem cells in adult primate testes." Human Reproduction, vol. 24, No. 5, pp. 1480-1491, 2009.
Orwig et al. "Cryopreservation and Transplantation of Spermatogonia and Testicular Tissue for Preservation of Male Fertility." Journal of the National Cancer Institute Monographs, No. 34, 2005.
Radford et al. "Fertility after treatment for cancer." BMJ, vol. 319, Oct. 9, 1999.
Radford "Restoration of Fertility after Treatment for Cancer." Hormone Research 2003:59 (suppl 1) 21-23.
Schlatt et al. "Limited survival of adult human testicular tissue as ectopic xenograft." Human Reproduction, vol. 21, No. 2, pp. 384-389, 2006.
Schlatt et al. "Review: Testicular Stem Cells for Fertility Preservation: Preclinical Studies of Male Germ Cell Transplantation and Testicular Grafting." Pediatr Blood Cancer 2009; 53: 574-280.
Turnpenny L et al. "Evaluating human embryonic germ cells: Concord and conflict as pluripotent stem cells," Stem Cells, published online Sep. 6, 2005; doi:10.1634/stemcells.2005-0255.
Yuan et al. "Generation of mice by transplantation of an adult spermatogonial cell line after cropreservation." Cell Proliferation 2009, 42, 123-131.
Zou et al. "Production of offspring from a germline stem cell line derived from neonatal ovaries." Nature Cell Biology, vol. 11, No. 5, May 2009.
International Search Report, PCT/US2010/055706, mailed Mar. 3, 2011.
Huleihel M et al. "In vitro culture of testicular germ cells: regulatory factors and limitations," Growth Factors 25:236-252, 2007.
Lee Dr et al. "Isolation of male germ stem cell-like cells from testicular tissue of non-obstructive azoopermic patients and differentiation into haploid male germ cells in vitro," Human Reproduction 21:471-473, 2006.
Bahadur et al. "Gonadal tissue cryopreservation in boys with paediatric cancers." Human Reproduction 14:11-17, 1999.
Brinster et al. "Spermatogonial stem cell transplantation, cryopreservation and culture." Semin. Cell. Dev. Biol. 9:401-9, 1998.
Jeruss et al. "Preservation of fertility in patients with cancer." N. Eng. J. Med. 360:902-911, 2009.
Keros et al. "Methods of cryopreservation of testicular tissue with viable spermatogonia in pre-pubertal boys undergoing gonadotoxic cancer treatment." Human Reproduction 22:1384-1395, 2007.
Stukenborg et al. "New horizons for in vitro spermatogenesis? An update on novel three-dimensional culture systems as tools for meiotic and post-meiotic differentiation of testicular germ cells." Mol. Hum. Reprod. 15:521-529, 2009.
Shamblott et al. (2004) Derivation and differentiation of human embryonic germ cells. In "Handbook of Stem Cells" (R. Lanza, B. Hogan, D. Melton, R. Pederson, J. Tomson, and M. West, eds.), Elsevier Inc.: New York, vol. 1, pp. 459-469.
Alberts et al., Chapter 20: Germ Cells and Fertilization. Molecular Biology of the Cell, Third Edition, Library of Congress, pp. 1026-1029 (1994).
Meyts et al., The testis in childhood between birth and puberty. Atlas on the human testis, normal morphology and pathology, Springer-Verlag, London, pp. 69-75 (2013).
Setchell, Spermatogenesis and spermatozoa. Reproduction in mammals, Book 1 Germ Cells and fertilization, Austin & Short. Second Edition, Cambridge University Press. Chapter 4, pp. 63-92 (1982).
Cai et al., Methods for Isolation and Purification of Spermatogonial Stem Cell. Shanghai Journal of Animal Husbandry and Veterinary Medicine, vol. 1 (2008). Abstract only.
Li et al., Effects of Slow-freezing Method on the Development Potential of the Human Mature and Immature Oocytes. Journal of Practical Obstetrics and Gynecology, vol. 19, No. 3 (2003). Abstract only.
Lui et al., A simple technique for immature oocytes rescue by in-vitro-maturation culture in controlled ovarian hyperstimulation cycles. Journal of SUN YAT-SEN University (Medical Sciences) vol. 31, No. 2 (2010). Abstract only.
Tan et al., Development in study of premature ovarian failure. Tianjin Journal of Traditional Chinese Medicine, vol. 24, No. 3 (2007). Abstract only.
Wei et al., Effects of EGF on the In vitro Maturation and Parthenogenetic Development of Bovine Oocytes. Chinese Agricultural Science Bulletin, vol. 22, No. 8, pp. 14-17 (2006). Abstract only.
Yin et al., Development in Spermatogonial Stem Cell Transplantation Technology. Animal Science & Veterinary Medicine, vol. 18, No. 3, pp. 13-14 (2001). Abstract only.
Aponte PM et al. "Spermatogonial stem cells: characteristics and experimental possibilities" APMIS 113:11-12, 2005.
Kim, et al.: "Establishment of a Simple and Effective Method for Isolating Male Germline Stem Cells (GSCs) from Testicular Cells of Neonatal and Adult Mice" Journal of Microbiology and Biotechnology, 2006, 16(9), pp. 1347-1354.
Honaramooz A et al. "Sperm from neonatal mammalian testes grafted in mice," Nature 418:778-781, 2002.

* cited by examiner

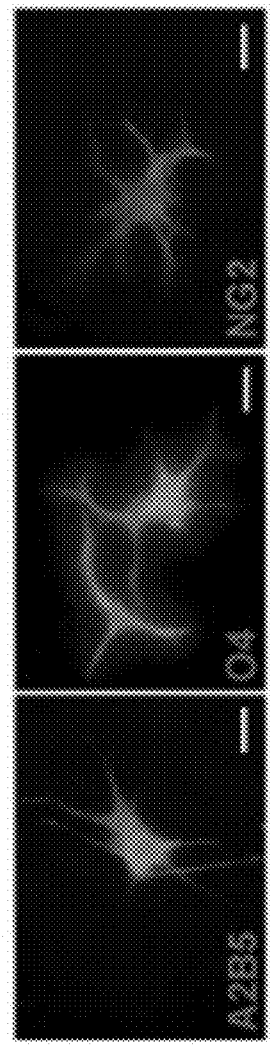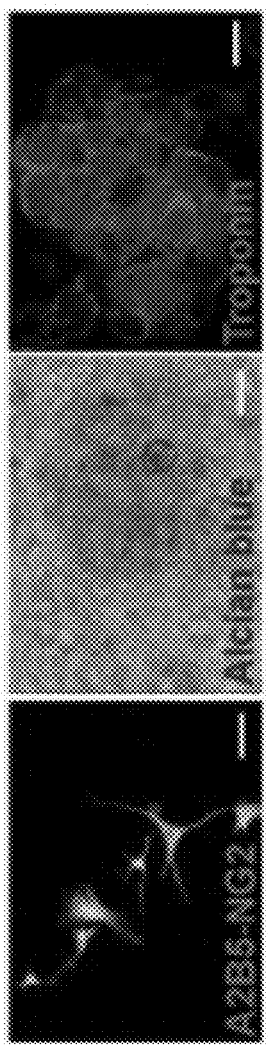

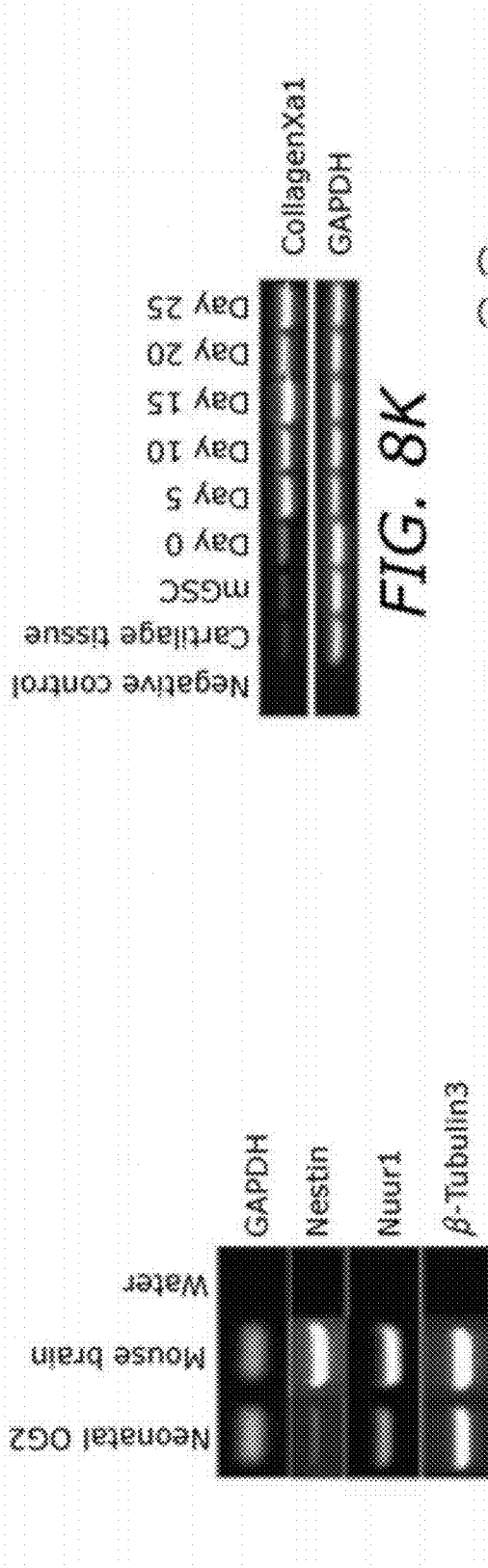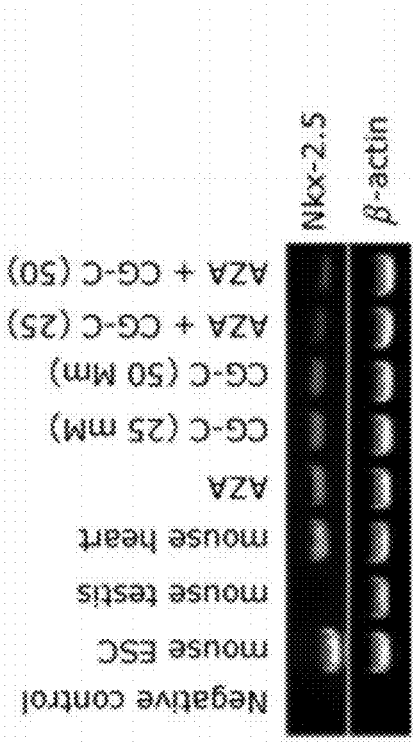
FIG. 8K
FIG. 8L
FIG. 8J

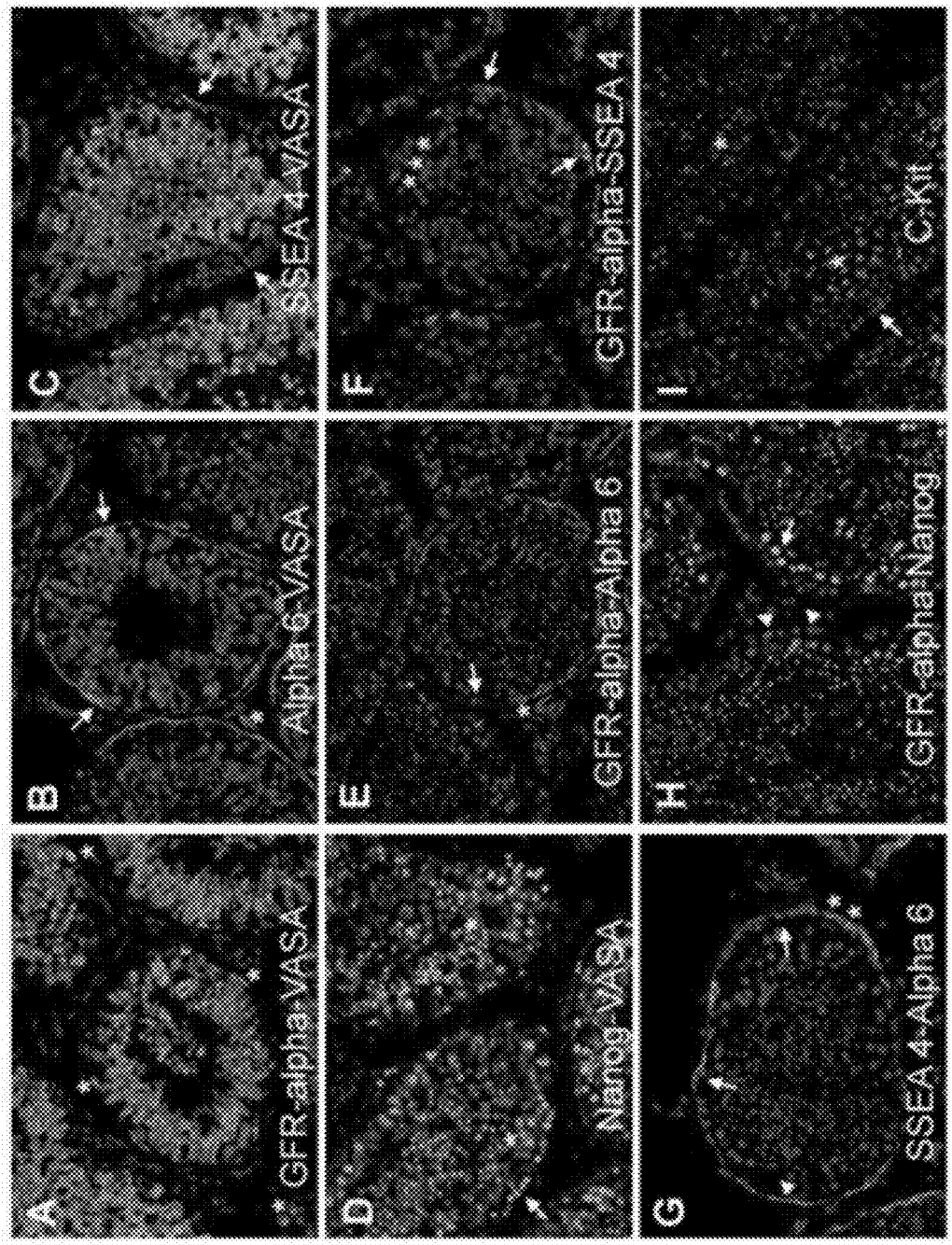

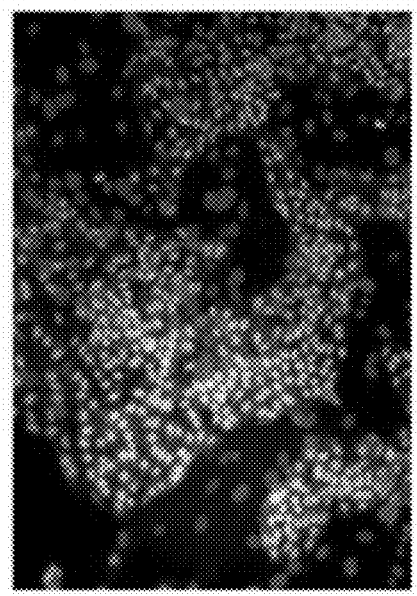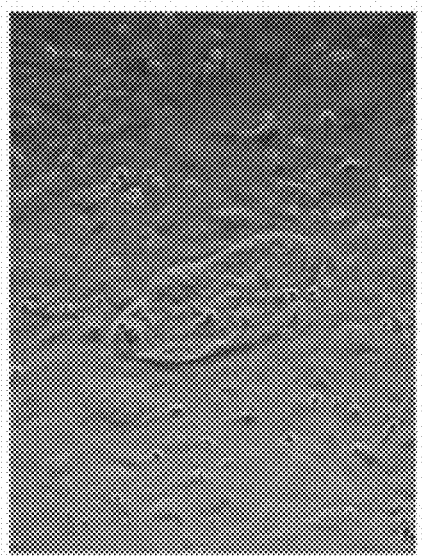

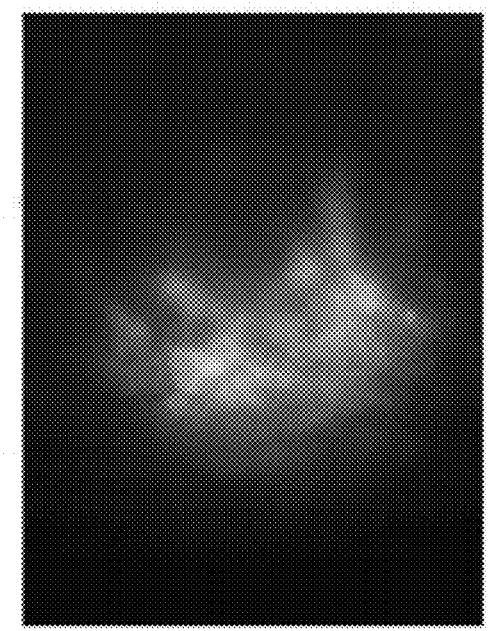
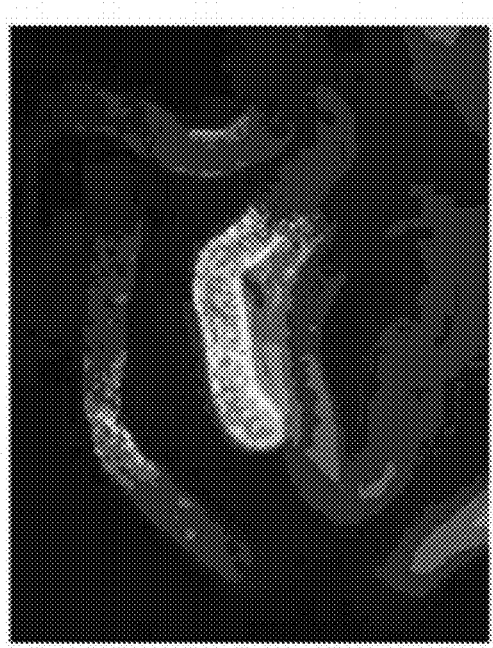
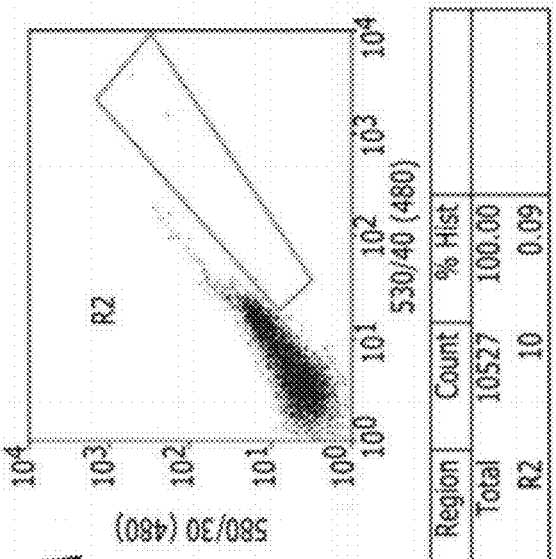
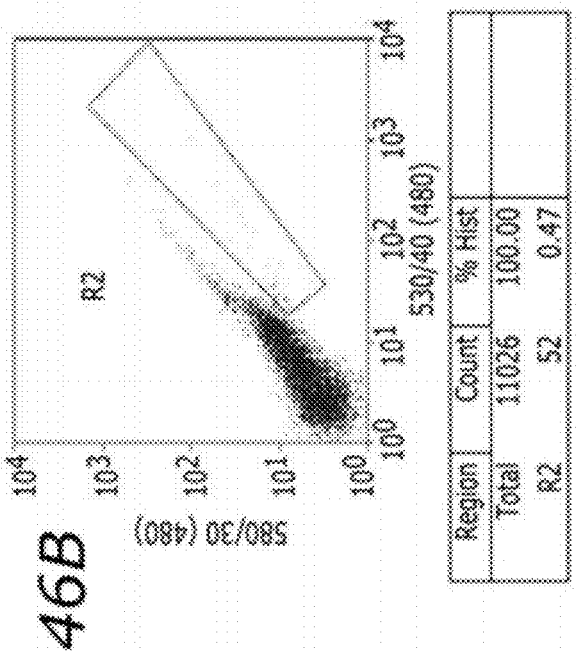
FIG. 46A
FIG. 46B

EX HOST MATURATION OF GERMLINE STEM CELLS

CROSS-REFERENCE TO RELATED APPLICATIONS

This application claims the benefit under 35 U.S.C. §119(e) to U.S. Provisional Application No. 61/258,535 filed Nov. 5, 2009, the entire contents of which is incorporated by reference herein.

FIELD OF THE INVENTION

The present invention relates to a system of maturing of germline stem cells outside of the host or ex host maturation (either in vitro or in vivo in a surrogate animal) from patients at risk of infertility due to damage to their germline stem cells and restoration of fertility in the patients at a later date. Ex host maturation combined with subsequent in vitro fertilization and uterine implantation is necessary if such patients were treated using chemotherapy or radiation therapy for malignancies, and direct re-implantation or autologous transplantation back into the host patient is to be avoided for fear of re-introducing possible tumor cells contaminating the original explanted testicular or ovarian tissue

BACKGROUND OF THE INVENTION

Germline stem cells reside in the reproductive organs, i.e., the ovaries and testes, represent potentially one of the most important and protected classes of stem cells in the mammalian body. Genetic conservation and high telomerase activity has been reported in stem cells derived from these tissues, as well as, extensive DNA modification with chromatin chromosomal modifications. Scientists have differed about what types of stem cells are resident in adult reproductive tissues, as well as, their potentiality in differentiation.

Chemotherapy and radiation treatments not only target cancerous cells, but also rapidly dividing cells. In the testes, the rapidly dividing germ cells are highly sensitive to these exposures. In the prepubertal testis, germline stem cells are similarly sensitive and are acutely and dose-dependently depleted following radiation exposure. Low doses of cytotoxic drugs or irradiation deplete the differentiating spermatogonia while less sensitive spermatogonial stem cells as well as spermatocytes and spermatids may survive. The differentiating germ cells can continue their maturation into sperm cells and can re-colonize the seminiferous tubules with stem cells which are generated from the surviving stem cell population.

However, in cases of severe depletion, spermatogeneis may only be restored in a very few seminiferous tubules, thereby limiting fertility. Patients will be permanently infertile after complete depletion of testicular stem cells. The impact on spermatogenesis manifests itself most acutely at, or before, the time of puberty because sperm cannot be typically obtained and cryopreserved as in postpubertal males. Even a few stem cells can re-colonize the seminiferous tubules if given sufficient time to re-initiate spermatogenesis.

Until recently, it was believed that female gonads of most mammalian species, including humans, house a finite number of meiotically-arrested germ cells (oocytes) enclosed within primordial follicles that serve as the stockpile of eggs released at ovulation during each menstrual cycle. Oocyte numbers decline throughout postnatal life, through mechanisms involving apoptosis, which were widely believed to eventually leave the ovaries barren of germ cells. In humans, exhaustion of the oocyte reserve typically occurs during the fifth decade of life, driving menopause.

According to this basic doctrine of reproductive biology, it was further believed that once depleted, the ovarian germ cell pool could not be replenished. Thus, any treatment that accelerates the loss of oocytes threatens to decrease the fertility and will cause menopause at an earlier age than expected. For example, exposure of women to a wide spectrum of agents that damage the ovary, such as chemotherapeutic agents and radiotherapy, generally leads to premature menopause and irreversible sterility. At present, the limited therapeutic options of preserving fertility and normal ovarian function under various adverse conditions are invasive, such as, for example, cryopreservation of ovarian tissue fragments or single oocytes, and often require prior hormonal therapy, which can be medically inappropriate for many women with hormonally responsive tumors. In addition, there are currently no therapeutic options for postponing normal ovarian failure at menopause.

Two primary approaches have been identified for restoration of functional germ cells in both males and females. The first is the grafting of immature tissue (either ovarian or testis) tissue fragments onto the surviving tissue and the second is based on isolation and transplantation of stem cells.

Germ cell transplantation has been developed in rodent animal models. Microinjection of germ cells from mice or closely-related species into the seminiferous tubules of a mouse re-stimulated spermatogenesis from donor spermatogonial stem cells. The spermatogonial cells can be cryopreserved or cultured prior to transfer. Similarly cyropreserved ovarian cortical tissue has been transplanted in sheep and human with the resulting resumption of estrus and the birth of live offspring following normal matings. However, such direct autologous transplantation back into the donor organism may not be optimal for patients who were originally treated for malignancies. This is because if such patients relapse after chemotherapy or radiation therapy, it is not clear whether the relapse could be from reservoirs of malignant cells in the body that were not killed with chemotherapy or radiation therapy or if the re-transplantation of cryopreserved gonadal tissue and cells harbored such malignant cells. As such, the optimal approach for such patients is to mature the cryopreserved gonadal tissue into functional sperm or eggs, and perform in vitro fertilization (with or without intracytoplasmic sperm injection or ICSI) with the natural or similarly ex host matured egg or sperm of the partner, and then after re-implant the fertilized embryo into female partner. This approach would be free from any possibility of tumor contamination as only the fertilized embryo formed from uncontaminated ex host matured sperm or egg.

Therefore, a germline cell banking system is needed in humans to restore reproductive potential in patients without the ability to bank mature sperm or ova and to mature the banked germline cells ex host/ex vivo or ex host/in vivo to produce mature sperm or ova.

SUMMARY OF THE INVENTION

The present disclosure provides methods to mature immature germline stem cells to produce mature reproductive cells.

In one embodiment disclosed herein, a method is provided for maturing immature germline cells into haploid gametes ex host comprising the steps of obtaining immature germline cells from testes or ovaries; and culturing the immature germline cells in vitro under conditions which mimic the conditions by which the cells mature in vivo, wherein the culturing causes maturation of the immature germline cells into functional sperm or oocytes.

In another embodiment, the immature germline cells are obtained from prepubertal patients. In another embodiment, the immature germline cells are cryopreserved prior to maturation. In another embodiment, the immature germline cells are germline stem cells or premeiotic germ cells.

In one embodiment, culturing comprises culture of immature testicular germline cells in artificial seminiferous tubules. In another embodiment, culturing comprises culture of immature testicular germline cells in the presence of at least one growth promoting factor selected from the group consisting of glial cell line-derived growth factor, fibroblast growth factor, leukemia inhibitor factor and epidermal growth factor. In another embodiment, culturing comprises culture of immature testicular germline cells in the presence of at least one maturation-inducing factor selected from the group consisting of follicle stimulating hormone, stem cell factor and retinoic acid.

In another embodiment, the artificial seminiferous tubules comprise biocompatible tubing coated with extracellular matrix. In another embodiment, the extracellular matrix is testicular extracellular matrix. In yet another embodiment, the testicular extracellular matrix is autologous to the testicular germline cells In one embodiment, culturing comprises culture of immature ovarian germline cells in the presence of granulosa cells and fibrin clot. In another embodiment, culturing comprises culture of immature ovarian germline cells cultured in the presence of growth promoting factors including glial cell line-derived growth factor, fibroblast growth factor, leukemia inhibitor factor, epidermal growth factor and growth hormone. In yet another embodiment, culturing comprises culture of immature ovarian germline cells cultured in the presence of maturation inducing factors including follicle stimulating hormone, stem cell factor, and retinoic acid.

In another embodiment, the fibrin clot is autologous to the ovarian germline cells. In another embodiment, the granulosa cells are autologous to the ovarian germline cells.

BRIEF DESCRIPTION OF THE DRAWINGS

FIG. 2D Day 15-20). Approximately three weeks after culture, colonies containing small round cells were formed (FIG. 2E; Day 20-30). Up-regulation of Oct-4 was observed about one month after culture (FIG. 2F; Day 30-40). Images of three established mGC lines derived from neonatal OG2, adult OG2 or neonatal OG2-LacZ are presented in FIGS. 2G-I (FIG. 2G, Neonatal OG2; FIG. 2H, Adult OG2; FIG. 2I, OG2 LacZ), respectively. Scale bars: 50 µm.

FIG. 7 depicts the spontaneous differentiation of mGCs. Gastulation of embryoid body (EB; FIGS. 7A and 7I: 50 µm; FIGS. 7C and 7E: 30 µm; FIGS. 7B and 7D: 25 µm.

FIG. 8 depicts the induced differentiation of mGCs into lineage-specific phenotypes. Confocal images of the cells expressed neural markers are shown in FIG. 8A-8G. Expression of the neural gene markers is shown in FIG. 8J. Confocal image of mGCs differentiated into cardiomyocytes are presented in FIG. 8I. Expression of the cardiac gene markers is shown in FIG. 8L. Alcian blue positive chondrocyte after differentiation of mGCs is shown in FIG. 8H. Expression of the chondrocyte specific genes is shown in FIG. 8K. Scale bars: FIGS. 8A, 8C and 8G: 20 µm; FIGS. 8B and 8H: 50 µm; FIGS. 8D-8F and 8J: 10 µm.

FIG. 9G-9H), in the muscle (arrows; FIG. 9I-9J), and in the testis (arrows; FIG. 9K). Testes regeneration following transplantation of germline stem cells before and after culture is presented in FIG. 9M-9R. Cross section of the normal testis of an immune deficient mouse is shown in FIG. 9M. One month after busulfan treatment the majority of the seminiferous tubules are depleted from endogenous spermatogenesis (FIG. 9N). Testes of a mouse transplanted with freshly isolated Oct-4+ cells showed spermatogenesis in more than 50% of seminiferous tubule cross sections indicating the presence of cells with SSC property in this population (FIG. 9O). While more than 80% of seminiferous tubules of the mice transplanted with Oct-4+/c-Kit– cells showed some degree of spermatogenesis (FIG. 9P), the majority of tubule cross sections of the mice received Oct-4+/c-Kit+ cells were empty (FIG. 9Q). Transplanted mGC also failed to repopulate recipient testes indicating that they do not have SSC properties (FIG. 9R). Scale bars: FIGS. 9A and 9K: 275 µm; FIGS. 9B, 9D and 9I: 60 µm; FIG. 9C: 140 µm; FIG. 9E: 100 µm; FIG. 9F: 50 µm; FIGS. 9G and 9L: 125 µm; FIGS. 9H and 9J: 40 µm; FIG. 9M-9R: 60 µm.

FIG. 10H-10K show the chimeric pattern in dissected organs and FIG. 10L-10O show the chimeric cell population in histological sections in the brain, heart, liver and gonadal ridge (chimeric LacZ-GFP cells appear in blue). Amplification of the GFP and LacZ DNA in tissues of the chimeric pups is shown in FIGS. 10P and 10Q, respectively. Scale bars: FIGS. 10A and 10C: 50 µm; FIGS. 10B and 10D: 25 µm; FIG. 10E-10D: 1250 µm; FIG. 10H-10K: 625 µm; FIG. 10L-10N: 50 µm; FIG. 10O: 10 µm.

FIG. 11 depicts graphically in a flow cytometric plot the results of freshly isolated neonatal and adult ovarian cells from transgenic OG2 mice wherein the Oct-4 promoter drives expression of GFP.

FIG. 12 depicts germline stem cells identifiable by expression of green fluorescent protein in the ovary of a transgenic OG2 mouse at day 2 after birth.

FIG. 14 depicts microscopic images of isolated and substantially purified ovarian germline stem cells established and growing as colonies on a feeder layer of MEF cells.

FIG. 16 depicts images of differentiating ovarian germline stem cells.

FIG. 17 graphically depicts in a scatter plot the results of a flow cytometric size analysis of the cultured ovarian cells of FIG. 16 confirming and characterizing the large (>15 µm) oocyte-like cells.

FIG. 18 depicts immunohistochemical localization of spermatogonial stem cell and germline cell markers in adult primate testes.

FIG. 29 depicts the morphology of an expanded primate germline stem cell colony 10 days after culture on MEF feeder layer (FIG. 29A); SSEA-4 staining of expanded primate germline stem cell colonies (FIGS. 29B and C); and GFR-α staining of an expanded primate germline stem cell colony after passage 4 (FIG. 29D)

FIG. 45 depicts the average weights of nude offspring conceived as a result of male germline stem cell transplantation.

FIG. 46 depicts flow cytometric analysis of GFP+ sperm and tubules in the right (FIG. 46A) and left (FIG. 46B) testes of an infertile mouse.

DEFINITION OF TERMS

Figure 1A:
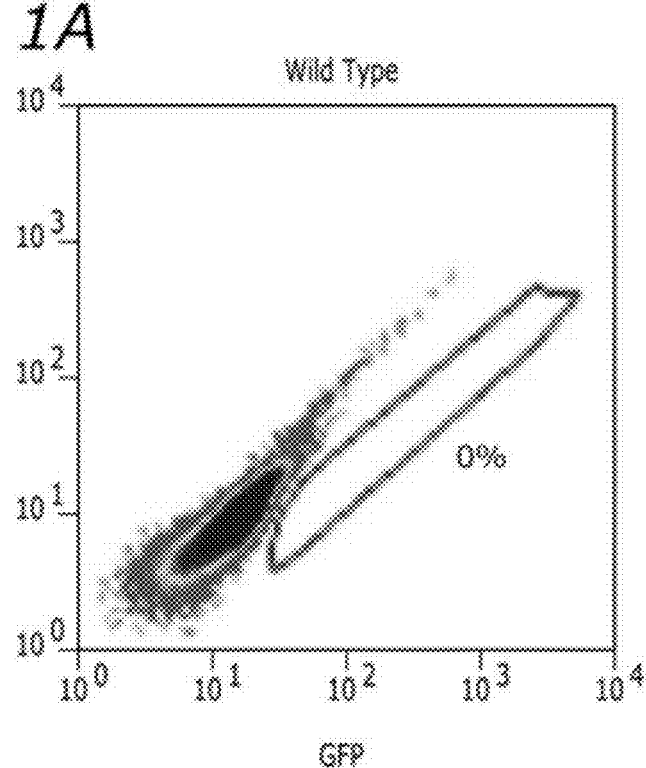
FIG. 1 depicts enrichment of GFP (green fluorescent protein) positive subpopulations of testicular stem cells isolated from the transgenic OG2 mouse using flow cytometry. Oct-4+ cells as indicated by GFP expression were found as a distinct cell population in both neonatal (FIG. 1B) and adult (FIG. 1C) OG2 mouse compared to the wild type (FIG. 1A). Among the Oct-4+ cells, two clear subpopulations consisting of c-Kit+ (R5) and c-Kit− (R2) were found (FIGS. 1D-1E). Correlation between expression of GFP and c-Kit is also shown (FIGS. 1F-1H).

The following definition of terms is provided as a helpful reference for the reader. The terms used in this patent have specific meanings as they related to the present invention. Every effort has been made to use terms according to their ordinary and common meaning. However, where a discrepancy exists between the common ordinary meaning and the following definitions, these definitions supercede common usage.

Committed: As used herein, "committed" refers to cells which are considered to be permanently committed to a specific function. Committed cells are also referred to as "terminally differentiated cells."

Culture: As used herein, "culture" or "cultured" refers to the propagation of cells under controlled conditions such that cell division and increase in cell numbers occurs.

Differentiation: As used herein, "differentiation" refers to the adaptation of cells for a particular form or function. In cells, differentiation leads to a more committed cell.

Embryonic Stem Cell: As used herein, "embryonic stem cell" refers to any cell that is totipotent and derived from a developing embryo that has reached the developmental stage to have attached to the uterine wall. In this context embryonic stem cell and pre-embryonic stem cell are equivalent terms. Embryonic stem cell-like (ESC-like) cells are totipotent cells not directly isolated from an embryo. ESC-like cells can be derived from primordial sex cells that have been isolated and expanded.

Ex Host: As used herein, "ex host" refers to maturation of germline cells outside of the donor's body. For purposes of this disclosure ex host maturation can include ex vivo, in vitro and in vivo (in another non-donors human or another species) maturation of donor germline cells.

Expanded: As used herein, "expanded" refers to a growing culture of cells that has increased in cell number from its original concentration.

Fetal Stem Cell: As used herein, "fetal stem cell" refers to a cell that is multipotent and derived from a developing multi-cellular fetus that is no longer in early or mid-stage organogenesis.

Gamete: As used herein, "gamete" refers to a reproductive cell containing half of the genetic material necessary to form a complete human organism. During fertilization, male and female gametes (sperm and ovum, respectively) fuse, producing a zygote.

Germ Cell: As used herein, "germ cell", "germline cell," or "germline tissue" refers to a reproductive cell such as a spermatocyte or an oocyte, or a cell that will develop into a reproductive cell or a tissue containing such cells.

Germline Precursor Stem Cell: As used herein, "germline precursor stem cell" refers to a reproductive cell such as a precursor of a spermatogonial stem cells or an oocyte precursor stem cell.

Germline Stem Cell: As used herein, "germline stem cell" refers to a reproductive cell such as a spermatogonial stem cell (SSC) or an oocyte precursor stem cell.

Gonad: As used herein, "gonad" refers to any of the paired organs in animals that produce reproductive cells (gametes). These include female ovaries, which produce eggs, and male testes, which produce sperm.

Immature: As used herein, the term "immature" refers to germline cells that have not reached their mature, functional differentiated state.

Long-term culture: As used herein, "long-term culture" refers to the propagation of cells under controlled conditions for longer than at least two months or more than 10 passages. Preferably the long-term cultures are cultured for more than 4 months, more than 6 months or more than 1 year. Preferably the long-term cultures are passaged for more than 15 passages, more than 18 passages or more than 20 passages. The duration of the long-term cultures is highly dependent on the individual cells and there can be variability from cell line to cell line.

Maturation: As used herein, "maturation" refers to a process of coordinated biochemical steps leading toward a terminally differentiated cell type.

Multipotent: As used herein, "multipotent" refers to cells that can give rise to several other cell types, but those cell types are limited in number. An example of multipotent cells is hematopoietic cells—blood stem cells that can develop into several types of blood cells but cannot develop into brain cells.

Multipotent Adult Progenitor Cells: As used herein, "multipotent adult progenitor cells" refers to multipotent cells isolated from the bone marrow which have the potential to differentiate into cells of the ectoderm, mesoderm and endodermal lineages.

Pluripotent: As used herein, "pluripotent" refers to cells that can give rise to any cell type except the cells of the placenta or other supporting cells of the uterus.

Post-natal Stem Cell: As used herein, "post-natal stem cell" refers to any cell that is derived from a multi-cellular organism after birth.

Pre-Pubescent: As used herein, "pre-pubescent" or "pre-pubertal" refers to individuals who have not yet entered puberty. Onset of puberty is associated with high gonadotrophin releasing hormone (GnRH) pulsing, which precedes the rise in sex hormones, lutenizing hormone (LH) and follicle stimulating hormone (FSH). Puberty begins consistently at around 47 kg for girls and 55 kg for boys. Although there is a wide range of normal ages, on average, girls begin the process of puberty about 1-2 years earlier than boys (with average ages of 9 to 14 for girls and 10 to 17 for boys), and reach completion in a shorter time with girls usually having completed puberty by age 17.

Primordial Germ Cell: As used herein, "primordial germ cell" (PGC) refers to cells present in early embryogenesis that are destined to become germ cells.

Primordial Germline Sex Stem Cell: As used herein, "primordial germline sex stem cell", also referred to in short form as a "germline sex cell" abbreviated PGLSC, refers to a cell that is derived from adult male or female reproductive tissue, and which is able to generate germline stem cells and their progeny as evidenced by its ability to repopulate reproductively sterile testicular or ovarian tissues after e.g. radiation or chemotherapy. Germline sex cells can be quiescent or actively dividing in adult reproductive tissues.

Reprogramming: As used herein "reprogramming" refers to the resetting of the genetic program of a cell such that the cell exhibits pluripotency and has the potential to produce a fully developed organism. In addition this reprogramming gives the cell undergoing reprogramming characteristics that would normally not be expressed or found in the cell in its pre-programming state.

Selection" As used herein, "selection" refers to fluorescence-activated cell sorting, magnetic bead sorting or other means of collecting cells bearing a particular marker profile Sex Cell: As used herein, "sex cell" refers to diploid or haploid cells derived from the mammalian male or female reproductive tissues. Representative examples of these cells include male gonocytes, female gonocytes, oogonia, type-A spermatogonia and Type-B spermatogonia.

Somatic Cell: As used herein, "somatic cell" refers to any tissue cell in the body except sex cells and their precursors.

Somatic Stem Cells: As used herein, "somatic stem cells" refers to diploid multipotent or pluripotent stem cells. Somatic stem cells are not totipotent stem cells.

Stem Cells: As used herein, "stem cells" refers to cells capable of self-renewal (the ability to go through numerous cycles of cell division while maintaining the undifferentiated state and being at least multipotent (the capacity to differentiate into more than one specialized cell type.

Substantially Pure: As used herein, "substantially pure" refers to a population of cells wherein greater than 75%, greater than 85%, greater than 90%, greater than 95%, greater than 98% or greater than 99% of the cells have the desired characteristic(s).

Totipotent: As used herein, "totipotent" refers to cells that contain all the genetic information needed to create all the cells of the body plus the placenta. Human cells have the capacity to be totipotent only during the first few divisions of a fertilized egg.

DETAILED DESCRIPTION OF THE INVENTION

The present disclosure provides methods for ex host maturation of germline stem cells from both males and females and restoration of fertility or fertility potential in individuals who cannot mature germ cells in vivo in their own body, for example for fear of tumor cell re-introduction.

Chemotherapy and radiation therapy used in the treatment of cancers, as well as other non-malignant diseases (such as, but not limited to, sickle cell anemia and thalassemia) prior to bone marrow stem cell transplantation has a well-documented, detrimental effect on the fertility of patients undergoing these therapies. These treatments may permanently impair the reproductive capability of patients, presenting a 30% chance that the patients will become infertile.

Related methods of banking germline cells is disclosed in copending application Ser. No. 12/940,888 entitled "Germline stem cell banking system" filed on even date herewith and is incorporated by reference herein in its entirety.

Risks of Infertility in Males

It is desirable to bank testicular gonadal tissue and/or germline stem cells from pre-pubescent patients and to later mature these cells ex host to restore the reproductive potential of the patients.

Disorders or situations in which tissue and germline stem cell banking would be desired in males include, but is not limited to, bilateral cryptorchidism, testicular torsion, undescended testis, varicocele, cancer, including reproductive and non-reproductive cancers, cytotoxic therapy, bone marrow transplant. In one embodiment, the donor is a pre-pubertal male. In another embodiment, the donor is a post-pubertal male.

For adult patients, a precautionary step before treatment is the option to freeze sperm for in vitro fertilization or other assisted reproductive technologies, should the patient become infertile after treatment. For pre-pubescent patients who have not developed mature sperm at the time of chemo/radiotherapy, there is no other option but tissue or cell banking. Before the invention of the current methods by the instant inventors, there were no feasible options for restoring the fertility of male pre-pubescent patients. Extraction and cryopreservation of spermatogonial stem cells for fertility preservation is the subject of considerable research. Additionally, transplantation of cryopreserved testicular tissue (not single cell suspensions) has been successful in animal models but not yet in humans. Proof of concept of fertility restoration following transplantation of testicular tissue has been completed in a variety of animal models including murine, bovine, porcine and primate models as well as in human.

However, in cases where the patients suffered from malignancies, it is feared that direct re-implantation or transplantation of their testicular tissue and cells may re-introduce some contaminating tumor cells back into the host; therefore, it is desirable to mature these testicular cells and tissue into mature sperm ex host (either in vitro or in vivo in another non-human surrogate animal) and then use the matured sperm to perform in vitro fertilization on an egg. Such fertilized egg can then be implanted into the pre-readied uterus of the patient's choice without fear of tumor contamination.

Risks of Infertility in Females

It is desirable to bank ovarian tissue and cells for pre-pubescent patients and ovarian tissue, follicles and cells from adult patients and to later mature these cells ex host to restore the reproductive potential of the patients.

Disorders or situations in which tissue and germline stem cell banking would be desired in females include disorders and situations that directly or indirectly affect fertility such as, but is not limited to, ovarian cysts, ectopic pregnancies, hysterectomy, cancer, including reproductive and non-reproductive cancers, cytotoxic therapy, bone marrow transplant, ovariectomies, endometriosis, or for family planning purposes if woman wants to preserve reproductive potential but is approaching or passing her reproductive prime. In one embodiment, the donor is a pre-pubertal female. In another embodiment, the donor is a post-pubertal female.

In females, cytotoxic treatments cause follicular destruction and result in premature menopause and infertility. In addition to decreased reproductive potential, the loss of estrogen and other hormones can lead to long term health problems such as osteoporosis and cardiovascular disease. More than six percent of female childhood cancer survivors experienced acute ovarian failure. Adult women who had undergone cancer treatment have a 30% incidence of premature menopause. Other medical procedures such as ovariectomies and hysterectomies directly endanger or can affect a woman's fertility. These procedures are often needed when a patient is diagnosed with malignant or benign ovarian tumors, an ectopic pregnancy, endometriosis and ovarian cysts. Breast cancer patients, or those at risk for developing breast or ovarian cancer, often undergo ovariectomies to reduce their chance of developing such cancers due to hormonal complications and genetic predispositions.

There are limited options for women undergoing cytotoxic treatment to ensure reproductive ability in the future. As a precautionary step before cytotoxic or cytostatic therapy or surgical removal of reproductive organ(s), oocytes or eggs can be removed and cryopreserved for use with assisted reproductive technologies, should the patient become infertile after treatment. However, the viability of frozen and thawed human oocytes is quite low due to inherent difficulties in freezing a very large cell with low surface to volume ratio which does not allow cryoprotectant to penetrate the cell membrane easily. Therefore, tissue, primordial follicle, or ovarian cell (which may contain germline stem cells) banking is a viable option instead of, or in addition to, oocyte freezing.

Banked, cryopreserved ovarian tissue or follicles can be transplanted back into patients if they become infertile, at a time after treatment when they are ready to restore their fertility. Alternatively, for patients having undergone treatment for cancer or who do not have intact reproductive organ(s), the frozen tissue or follicles can be used in an ex host maturation process described herein, either in vitro or in an animal host (used only as a support system for maturing oocytes/follicles) and matured eggs can be fertilized by assisted reproductive techniques.

The germline cells disclosed herein are isolated from gonadal tissues from mammals including but not limited to, rodents, domesticated animals, dogs, cats and primates. The term "primates" includes, but is not limited to, humans.

The germline cells are isolated based on their expression, or lack of expression, of a variety of germline, embryonic and pluripotent cell markers. Germline cell markers include, but are not limited to, VASA, promyelocytic leukemia zinc factor (PLZF), glial derived neurotrophic factor receptor α1 (GFR-α1), α6-integrin, Thy-1, CD9, CD90, CD49f, *Dolichos biflourus* agglutinin (DBA), neural cell adhesion molecule (NCAM), germ cell nuclear antigen 1 (GCNA1) and DAZL.

Pluripotent cell markers include, but are not limited to, Oct-4 (POU5F1), Nanog, alkaline phosphatase, SSEA-4, TRA1-60 and TRA1-81.

Furthermore, germline cells can also be isolated based on the expression of germline and/or pluripotent stem cell genes. Germline stem cell genes include, but are not limited to, telomerase, VASA, c-RET, c-Kit, PLZF, DAZL and GFR-α1. Pluripotent cell genes include, but are not limited to, Oct-4, Nanog, Dppa-5, Sox2, alkaline phosphatase and Crypto.

Additional embodiments presented herein include the long-term culture of certain populations of germline cells such that long-term multipotent or pluripotent cells lines are generated. These cells lines can be used as a source of cells for differentiation into tissue-specific lineages. Long term culture of the instant germline cells comprises the steps of isolating a substantially pure population of the desired germline cell based on expression, or lack of expression, of germline and/or pluripotent cell markers and germline and/or pluripotent genes; culturing the cells in growth medium as disclosed in the Examples section which allow continued cell division while maintaining an undifferentiated multipotent or pluripotent state. The long-term cultures described herein can be cryopreserved for future uses.

In certain embodiments, isolated, substantially pure populations of germline cells or germline cell lines can be used for therapeutic applications in regenerative medicine. Germline cells disclosed herein are capable of forming more differentiated germline cells such as spermatocytes, spermatids and sperm in male, and follicles and oocytes in female and are capable of re-populating a sterile reproductive organ in vivo.

The germline tissue banking system comprises the following components and/or steps: 1) Tissue collection; 2) Transport of tissue to central banking location; 3) Processing of tissue at central bank; 4) Cryopreservation of tissue and isolated cells at central bank; and 5) Quality assurance and release of tissue and/or isolated cells. An optional sixth and seventh step comprises re-implantation of tissue and/or isolated cells into the donor or ex host maturation followed by in vitro fertilization and embryo implantation.

Disclosed herein are methods of ex host maturing of banked or fresh germline cells, such as germline stem cells, spermatogonial stem cells, ovarian stem cells, testicular tissue or ovarian tissue to allow restoration of reproductive potential to a patient who cannot conceive through natural means.

1. Tissue Collection from Males

Germline cells are retrieved from testes prior to the initiation of a cytotoxic procedure or soon after an injury which can lead to the destruction of the germ cell tissue. At least one gram of seminiferous tubule tissue is removed under surgical aseptic conditions and anesthesia. Physical and enzymatic digestion of the tissue to form a single cell suspension can be performed either prior to or after shipment of the tissue to the central banking facility.

In one embodiment, testicular seminiferous tubule tissue is cut into approximate 10×10 mm pieces and up to 5 pieces are placed in a sterile tube containing sterile shipping media. In another embodiment, the tissue is maintained in a single piece and placed in a sterile container containing sterile shipping media.

Shipping media includes any media which can support the viability of testicular seminiferous tubule tissue and/or dissociated cells for up to 24 hr. Non-limiting examples of tissue maintenance media include PBS, FRS, DMEM supplemented with HEPES and antibiotics (penicillin and streptomycin) as well as proprietary media disclosed in U.S. Patent Application Publication No. 2007-0020759, which is incorporated by reference herein for all it contains regarding tissue culture media.

2. Tissue Collection from Females

Germline cells are retrieved from ovaries prior to the initiation of a cytotoxic procedure, soon after an injury which can lead to the destruction of the germ cell tissue or at the time of ovariectomy or hysterectomy. At least one gram of ovarian tissue is removed under surgical aseptic conditions and general anesthesia. Physical and enzymatic digestion of the tissue to form a single cell suspension can be performed either prior to or after shipment of the tissue to the central banking facility.

In one embodiment, ovarian tissue is cut into approximate 10×10 mm pieces and up to five pieces are placed in a sterile tube containing sterile shipping media. In another embodiment, the tissue is maintained in a single piece and placed in a sterile tube containing sterile shipping media.

Shipping media includes any media which can support the viability of ovarian tissue and/or dissociated cells for up to 24 hr. Non-limiting examples of tissue maintenance media include PBS, FRS, DMEM supplemented with HEPES and antibiotics (penicillin and streptomycin) as well as proprietary media disclosed in U.S. Patent Application Publication No. 2007/0020759.

3. Transport of Tissue

The harvested testicular or ovarian tissue is kept at approximately 4° C. and transported to the central banking facility such that it arrives at the central banking facility within 24-72 hr of tissue harvesting.

4. Processing of Tissue

Harvested ovarian and testicular tissue is enzymatically dissociated, assessed for viability and cell markers prior to cryopreservation. In one embodiment, germline stem cells are enriched from the tissue prior to cryopreservation. In another embodiment, total testicular or ovarian cells, without enrichment for germline stem cells, are cryopreserved.

In another embodiment, enrichment for germline stem cells is conducted by flow cytometric sorting using antibodies specific for male and/or female germline stem cells.

5. Cryopreservation

A variety of media and procedures can be used for cryopreserving gonadal tissue and/or germline stem cells.

In one embodiment, germline stem cells are cryopreserved in a solution comprising at least one cryoprotectant including, but not limited to, dimethyl sulfoxide (DMSO), ethylene glycol, glycerol, and propanediol; at least one culture medium including but not limited to, DMEM, MEM and proprietary media disclosed above; at least one additional agent including, but not limited to, sucrose, dextran, a serum substitute and HEPES buffer. In one embodiment the solution comprises CryoStor™ CS-10 media (BioLife Solutions Inc., Bothell, Wash.). In another embodiment, the serum substitute is Knockout Serum Replacement (Invitrogen 10828-028).

The cells are then frozen at a controlled rate or by a "manual" process. The cells are then frozen at a controlled rate or by a "manual" process. The controlled-rate freezing procedure begins by turning the controlled-rate freezer on and setting up the freezing program for tissue or cell freezing. The controlled-rate freezer will use liquid nitrogen to decrease the temperature in an internal chamber (and thus decrease the temperature of any contents of that chamber). The freezing program for cells begins by cooling the internal chamber to 4° C. and holding it there until prompted to continue the procedure. While the controlled-rate freezer is cooling, cells are suspended in a cryopreservation media cooled to 4° C. That cell suspension is aliquoted into cryovials, 1 mL per cryovial. The cryovials are then labeled and placed in the controlled-rate freezer chamber and the program is prompted to continue. First, the chamber is temperature is held at 4° C. for an additional 10 minutes. Next, the chamber is cooled at a rate of −1° C./minute until the temperature reaches −80° C. The chamber then cooled at a rate of −50° C./minute until it reaches a temperature of −120° C. After 5 minutes at −120° C. the temperature of the frozen cells will equilibrate to −120° C. The cryovials of frozen cells are then transferred to a liquid nitrogen Dewar for long-term storage.

The manual freezing procedure begins by preparing a "Mr. Frosty" freezing container (Nalgene) which is used to slowly freeze the cells. The "Mr. Frosty" container is a polycarbonate unit that provides the critical, repeatable −1° C./minute cooling rate required for successful cell cryopreservation and recovery. The base of the "Mr. Frosty" is filled with 250 mL of 100% isopropanol. The tube rack is placed on top, the lid is screwed down over the tube rack and the "Mr. Frosty" is placed at 4° C. for at least 1 hour before being used. The cells are suspended in a cryopreservation media cooled to 4° C. That cell suspension is aliquoted into cryovials, 1 mL per cryovial. The cryovials are then labeled and placed in the pre-cooled "Mr. Frosty". The "Mr. Frosty" is placed back at 4° C. for 10 minutes. The "Mr. Frosty" is then placed in a −80° C. freezer overnight. After the overnight stay in the −80° C. freezer, the cryovials are transferred to a liquid nitrogen Dewar for long-term storage.

6. Quality Assurance and Release of Ovary- and Testes-Derived Germline Tissue and/or Cells Potency, purity, identity, viability and stability assays are performed on the samples prior to cryopreservation, or at specific time points (for stability), and upon release to ensure that the tissue or cells are in proper condition for transplantation. These assays quantify specific relevant markers in the tissue/cells sample that provide information on the amount of germline stem cells present (to extrapolate the "potency" potential to repopulate testes if transplanted), viability of cells, and optionally DNA analysis to confirm identity of the cells. Stability assays consist of small samples of tissue or cells being thawed at regular intervals to check quality of cryopreservation.

7. Re-Implantation of Testes-Derived Germline Tissue and/or Cells

Transplanting the isolated substantially pure population of germline stem cells into the recipient is accomplished by direct injection using standard injection means known to persons of ordinary skill in the art. In another embodiment, support cells, such as Leydig or Sertoli cells that provide hormonal stimulus to spermatogonial differentiation, are transferred to a recipient testis along with the germline stem cells. These transferred support cells are unmodified, or, alternatively, are genetically modified. These transferred support cells can be autologous or heterologous to either the donor or recipient testis. An example concentration of cells in the transfer fluid can easily be established by simple experimentation, but will likely be within the range of about $10^3$-$10^{10}$ cells per ml. The cells are be introduced into the vas deferens, the rete testis or the seminiferous is performed be done manually. A suitable dyestuff or bubbles (less than 2 μm in diameter) can optionally be incorporated into the carrier fluid for easy identification of satisfactory delivery of the transplanted germline stem cells to testes. An ultrasound equipped with appropriate transducer may be helpful for placing the needle in the injection site.

Suitable cell transplant vehicles are known to persons of ordinary skill in the art and include molecules such as serum albumin, cholesterol and/or lecithin, selenium and inorganic salts as well as serum components and/or growth factors and/or cytokines. Typically the cell transplant vehicle has a pH which is roughly physiologic, i.e. 7.0 to 7.6.

The instant cellular compositions may to be administered alone or in combination with one or more pharmaceutically acceptable carriers, in either single or multiple doses. Suitable pharmaceutical carriers may include inert biodelivery gels or biodegradable semi-solid matrices, as well as diluents or fillers, sterile aqueous solutions and various nontoxic solvents. The pharmaceutically acceptable carriers generally perform three functions: (1) to maintain and preserve the cells in the instant cellular composition; (2) to retain the cells at a tissue site in need of regeneration, restoration or rejuvenation; and (3) to improve the ease of handling of the instant composition by a practitioner, such as, but not limited to, improving the properties of an injectable composition or the handling of a surgical implant. The pharmaceutical compositions formed by combining an instant cellular composition with a pharmaceutically acceptable carrier may be administered in a variety of dosage forms such as injectable solutions, and the like. The pharmaceutical carriers can, if desired, contain additional ingredients such as binders, excipients, and the like. The aqueous solution is preferably suitably buffered if necessary and the liquid diluent first rendered isotonic with sufficient saline or glucose. Such aqueous solutions are suitable for intravenous, intramuscular, subcutaneous, and intraperitoneal injection. The subject sterile aqueous media employed are obtainable by standard techniques well known to those skilled in the art.

8. Re-Implantation of Ovary-Derived Germline Tissue and/or Cells

Ovarian germline stem cells could be isolated from patients prior to chemo or radiation therapy, expanded in number in vitro and kept frozen until the patient requires them to regain their fertility. Cells isolated from human ovary are transplanted directly into the ovarian surface epithelium using a fine needle or alternatively cells could be aggregated in a fibrin clot. Fibrin clots are prepared from patients own blood and support the viability and survival of cells during the implantation process. Fibrin clots could be transplanted back to the patient and grafted under the ovarian bursa.

In one embodiment, for transplantation of ovarian cells in patients with malignancies, germ cells are separated from the malignant cells using positive-negative selection procedures. In non-malignant patients however, transplantation of ovarian surface epithelium (OSE) may be more practical. Upon tissue collection, OSE is dissected from the rest of the ovarian tissue using scalpels to a 0.5 cm×0.5 cm pieces with the diameter of 1 mm. These pieces are frozen using a vitrification procedure and kept frozen until patients need them for fertility restoration. When needed, the OSE pieces are thawed and sutured together to make a larger piece and grafted to the surface of the infertile ovary.

Additionally, ovarian follicles at different developmental stages can be frozen and either re-implanted into the patient or be used for in vitro culture into mature follicles. Oocytes from these follicles could then be fertilized by ICSI (intracytoplasmic sperm injection) or other assisted reproductive techniques. Transplantation of ovarian germline stem cells is a permanent fertility restoration.

9. Ex Host Maturation of Ovary-Derived Germline Stem Cells

Female germline stem cells isolated from human ovaries can be differentiated into primordial follicles using an aggregation without growth factors and β-mercaptoethanol in ultra-low adhesive culture dishes following by 3D culture in sodium alginate or fibrin clot in the presence of growth hormone. To further support development of germ cells to mature egg, these cells are aggregated with immature granulosa cells from prepubertal age donors. This method allows development of primary oocytes to fertilizable metaphase-II oocytes. For isolation of granulosa cells, ovaries from prepubertal human ovaries are dissected and granulosa cells are separated from germ cells by a two step differential adhesion procedure. This method is applied for patients with malignancies, and engineered follicles devoid of malignant cells are then transplanted back into patient ovary allowing further maturation and follicular development. Alternatively these follicles are matured in vitro. Ovarian follicles isolated from patients can be frozen and subsequently subjected to this protocol. In either case the MII oocytes derived from these follicles are used for in vitro fertilization or ICSI for fertilization and subsequent embryo development.

10. Ex Host Maturation of Testes-Derived Germline Stem Cells

In the case that reimplantation of germline stem cells into the patient testes is not feasible (i.e. in malignancies, testes torsion, cryptorchidism) or in case germ cell development is impaired due to failure of testicular supporting cells (i.e. maturation arrest) the testicular germline stem cells are differentiated in a surrogate animal or in vitro to further developed stages and be used for ICSI or other assisted reproductive technologies. In one embodiment, spermatogonial stem cells (SSCs) are mixed with appropriate supporting cells and seminiferous tubule extracellular matrix (ECM) to create an environment that can support further development of germ cells.

In the case where spermatogenesis has already been started in prepubescent patients but not completed, partially mature germ cells that already entered meiosis (primary and secondary spermatocytes) can be stored and used for further differentiation to round or elongated spermatids. Spermatids then could be used for ICSI allowing fertilization and subsequent embryo development.

Described herein are methods for maturing immature germline cells into haploid gametes ex host by culturing immature germline cells in vitro under conditions which mimic the conditions by which the cells mature in vivo, wherein the culturing causes maturation of the immature germline cells into functional sperm or eggs.

The immature germline cells are obtained from prepubertal mammals or mammals having a condition which prevents normal maturation of germline cells. The disclosed methods are suitable for use in any mammals including, but not limited to, human, mice, domesticated animals such as cattle, swine, sheep and goats, dogs, cats, etc.

For ex host maturation of testicular germline cells, the artificial seminiferous tubules disclosed herein can be made of any biocompatible tubing that can be sterilized. In one embodiment, the tubing is a flexible, plastic or silicon material. In another embodiment, the inner diameter of the tubing is from approximately 150 µm to approximately 400 µm, alternatively from approximately 200 µm to approximately 350 µm, or alternatively from approximately 250 µm to approximately 300 µm. The inner surfaces of the tubing are coated with an extracellular matrix material to mimic the environment of the seminiferous tubules. In one embodiment, the extracellular matrix is testicular extracellular matrix. The extracellular matrix can be isolated from the germline stem cell donor or from another individual.

The testicular germline cells are cultured in the artificial seminiferous tubules in a culture media. The culture media, for example is PM-1™ medium (see US 2007/0020759). Alternative media include DMEM, F12, etc. or combinations thereof. The media is supplemented with growth and maturation factors including, but not limited to, including glial cell line-derived growth factor, fibroblast growth factor, leukemia inhibitor factor, epidermal growth factor, growth hormone, follicle stimulating hormone, stem cell factor, retinoic acid, and combinations thereof.

The testicular germline cells are cultured until mature sperm are observed morphologically in the artificial seminiferous tubules and are then harvested and either used to fertilize eggs through in vitro fertilization, intracytoplasmic sperm injection, or intravaginal or intrauterine insemination. Additionally, less mature cells, such as spermatids, can be transplanted back into the donor testis.

For ex host maturation of ovarian germline cells, ovarian germline cells are cultured in the presence of granulose cells in any culture medium disclosed herein. The matured cells can then be used for in vitro fertilization, intracytoplasmic sperm injection, or can be transplanted back into the donor ovary.

EXAMPLES

The following examples are meant to illustrate one or more embodiments are not limited to that which is described below.

Example 1

Isolation of Distinct Populations of Murine Male Germline Stem Cells

Pure populations of germline stem cells were isolated by sorting the Oct-4-GFP germ cells. Oct-4+ germ cells were then subdivided based on the expression of c-Kit receptor molecule. C-Kit, a tyrosine kinase receptor, and its ligand stem cell factor (SCF; also known as Kit ligand or Steel factor), are key regulators of PGC growth and survival.

C-Kit is expressed in PGCs from their initial segregation to their arrival at the genital ridge. In postnatal mouse testes, it has been reported that c-Kit can be used as a marker for differentiation of undifferentiated and differentiating type A spermatogonia. Combinations of Oct-4 and c-Kit allow the isolation of two distinct populations in germline stem cells: one containing more primitive germ cells or germline progenitors (Oct-4+/Kit+) and other contains germline stem cells destined to be SSCs (Oct-4+/c-Kit−) and with the ability to regenerate a sterile testis. The molecular and phenotypic characteristics of these cells were analyzed both before and after culture and compared their ability to generate multipotent cell lines under a defined culture condition with a mixture of growth factors. In addition, the functionality of these subpopulations and their descendent mGC lines to repopulate recipient testes was evaluated using spermatogonial stem cell transplantation technique.

Male germline stem cells (GSC) maintain spermatogenesis by self renewal of SSC and generation of spermatogonia committed to differentiation. Under certain in vitro conditions, GSC from both neonatal and adult mouse testis can reportedly generate multipotent germ cell (mGC) lines that have characteristics and differentiation potential similar to ESC. However, mGCs generated in different laboratories showed different germ cell characteristics; for example, some retain their SSC properties and some have lost it completely. Thus, the possibility remains that the derivative multipotent germ cell lines may have been derived from different subpopulations of germline stem cells resident within the mouse testes. To investigate this question, a transgenic mouse model expressing GFP under control of a germ cell-specific Oct-4 promoter was used. Two distinct populations were found among the germline stem cells with regard to their expression of transcription factor Oct-4 and c-Kit receptor. Only the Oct-4+/c-Kit+ subset of mouse germline stem cells, when isolated from either neonatal or adult testes and cultured in a complex mixture of growth factors, generate cell lines that express pluripotent ES markers i.e. Oct-4, Nanog, Sox2, Rex-1, Dppa5, SSEA-1, alkaline phosphatase, exhibited high telomerase activity and differentiated into multiple lineages including beating cardiomyocytes, neural cells and chondrocytes following induced differentiation protocols. This data clearly show the existence of distinct populations within germline stem cells from which only the germline progenitors can generate multipotent cell lines with some pluripotent characteristics.

Figure 1B:
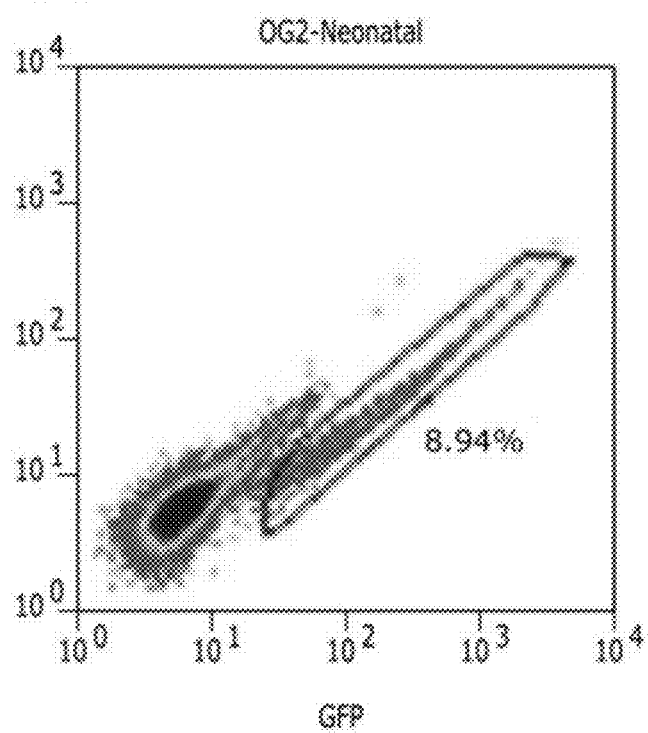
Figure 1C:
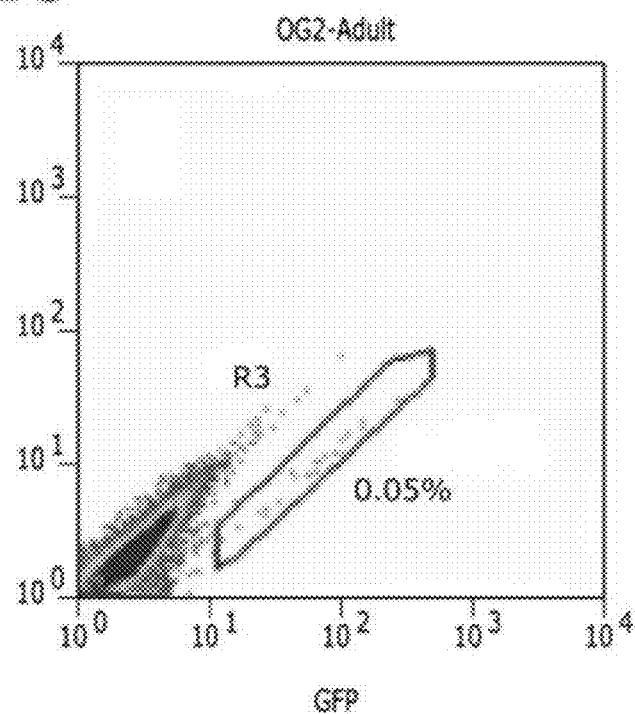
Figure 1D:
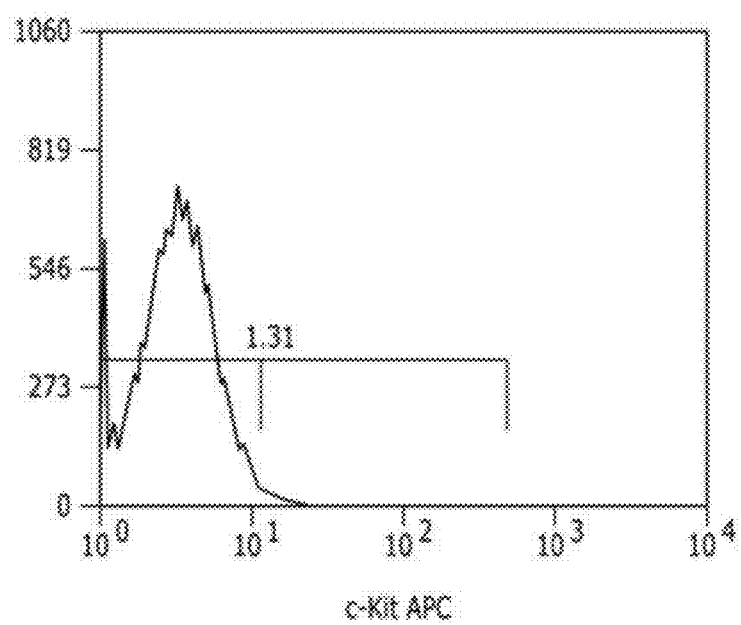
Figure 1E:
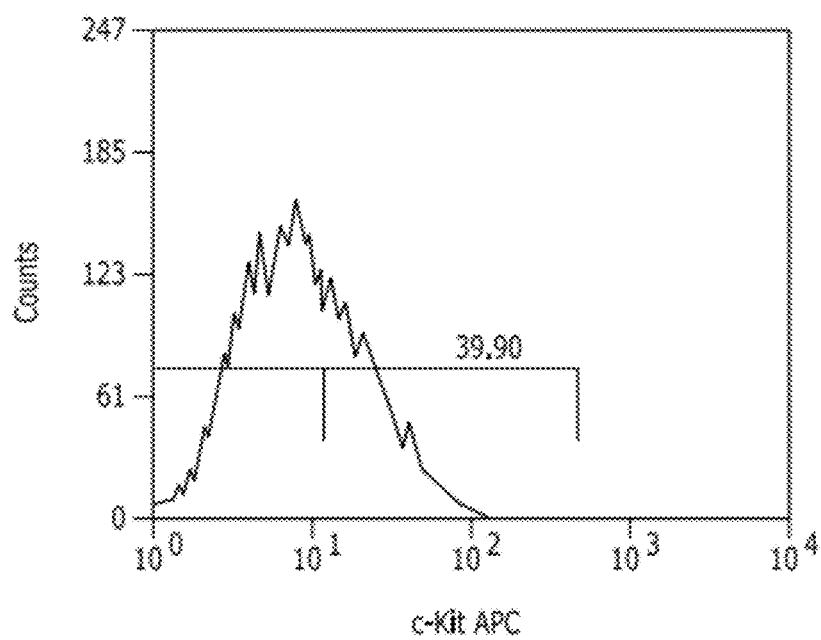
Figure 1F:
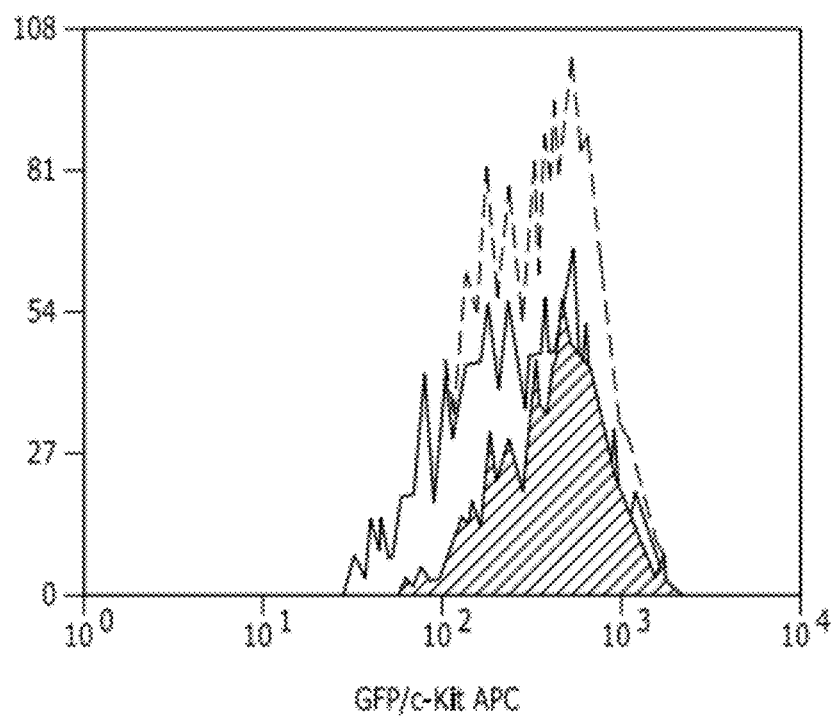
Figure 1G:
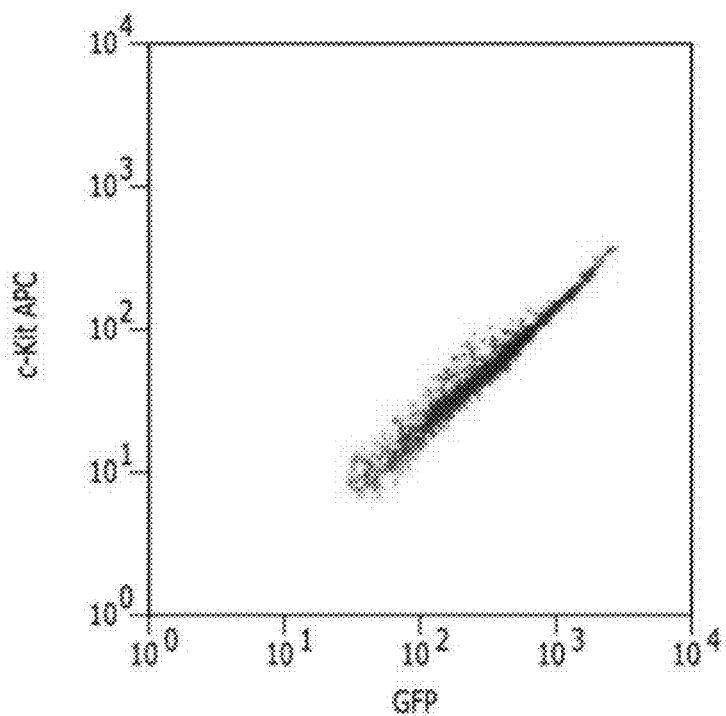
Figure 1H:
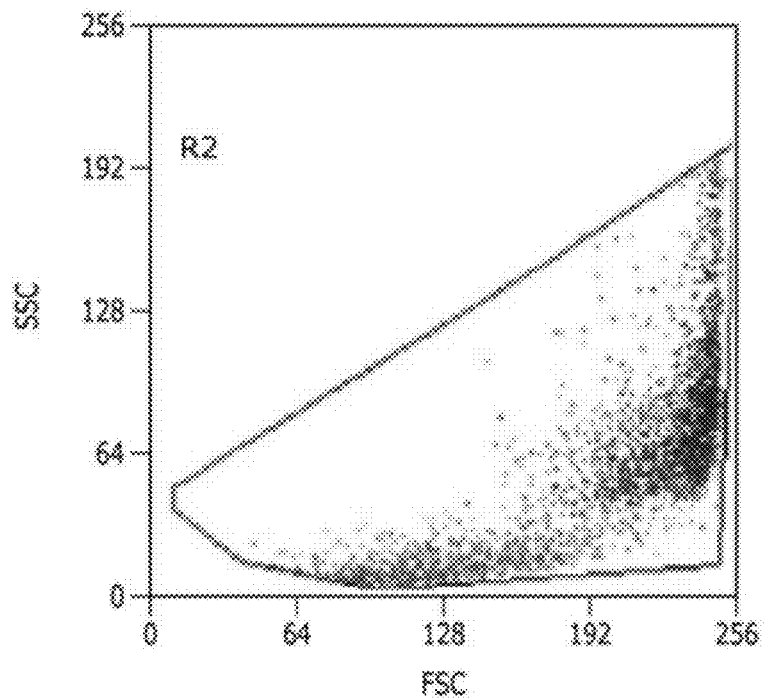

For enrichment of germline stem cells, both neonatal and adult testicular tissues were cultured on gelatin-coated culture dishes for 2 hr for differential adhesion to remove somatic cells but not germ cells. After differential adhesion, cell suspensions containing GFP positive cells (4-10% in the neonates; 0.01-0.05% in the adults) could be retrieved (FIG. 1A-C). There is correlation between expression of GFP and c-Kit (FIGS. 1F-1H).

Figure 2:
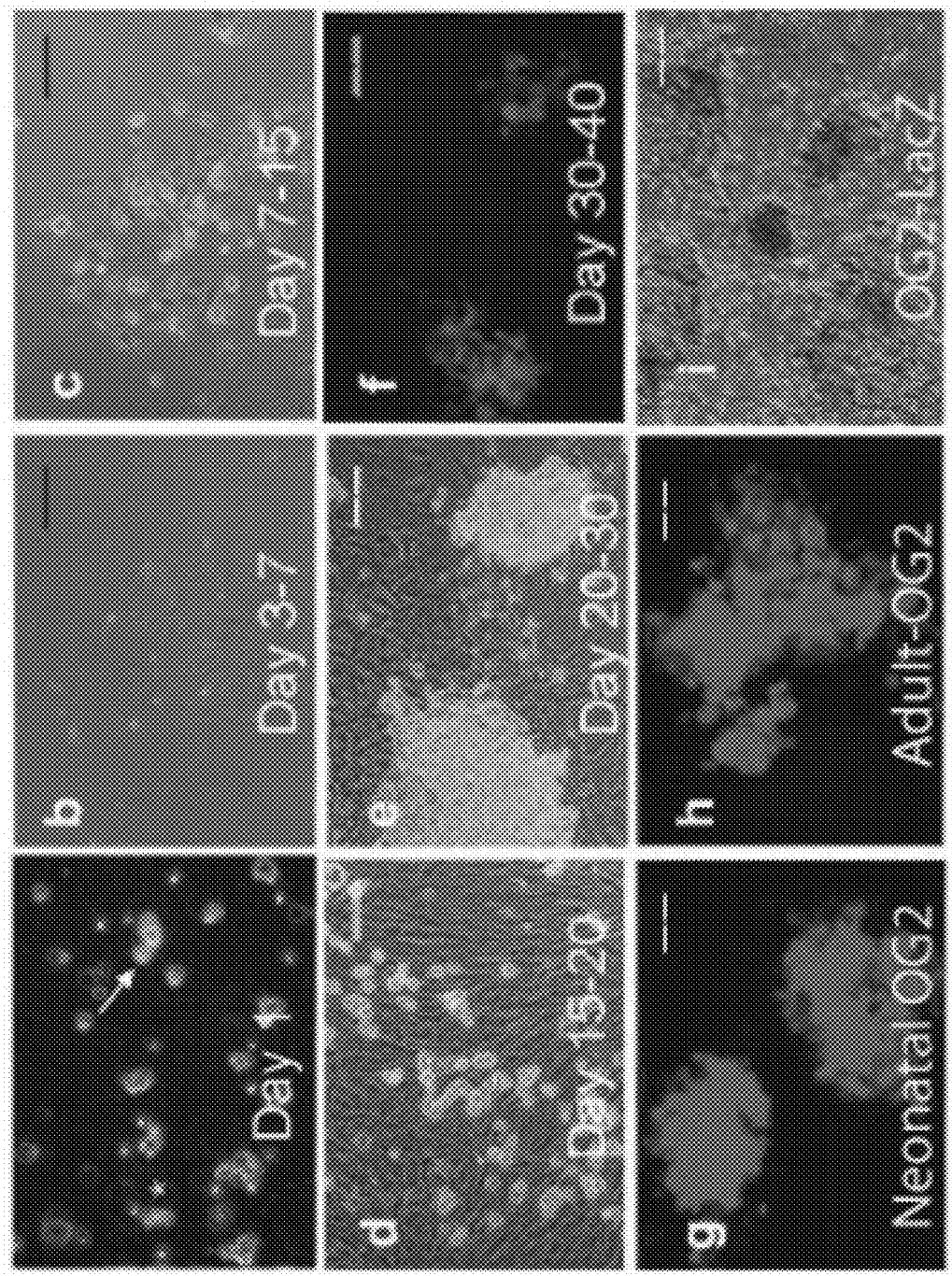
FIG. 2 depicts morphological changes during the development of multipotent germ cell (mGC) lines in culture. Mouse Oct-4+/GFP+ cells were observed in cell preparations before culture (FIG. 2A; arrows; Day 1-3). Shortly after culture, down regulation of Oct-4 was observed FIG. 2B; Day 3-7). After the attachment of the cells in the second week of culture obvious morphological changes occurred (FIG. 2C Day 7-15.

Harvested neonatal germ cells were cultured in a stem cell culture medium with a mixture of growth factors as described on culture dishes. Initial GFP signals (FIG. 2A) disappeared after a few days in culture (FIG. 2B). Thereafter, cells underwent distinct morphological changes, forming chain-like colonies that continued to grow without GFP signal (FIGS. 2C-2D). Up-regulation of Oct-4, indicated by the occurrence of GFP positive cells within colonies appeared after 3-4 weeks of culture (FIG. 2F). After 2-4 weeks in culture, GFP positive colonies were mechanically transferred into culture dishes with mitomycin C-treated murine embryonic fibroblast feeder layers (MEF) in the same culture medium supplemented with 15% FBS. After passing 3-4 times, via mechanical transfer to new MEF cultures, the colonies were established and could be removed from the culture plate enzymatically (collagenase 1 mg/ml, 5-10 min) for further expansion and/or storage in liquid nitrogen. For derivation of cell lines from adult mice, GFP+ cells harvested after differential adhesion were sorted using flow cytometry and were directly cultured on MEF. Using OG2 or OG2-lacZ mice, in total 19 cell lines (10 neonatal and 9 adult) have been generated. All cell lines expressed either GFP (14 lines) or GFP-LacZ (5 lines) (FIGS. 2G-2I).

Figure 3A:
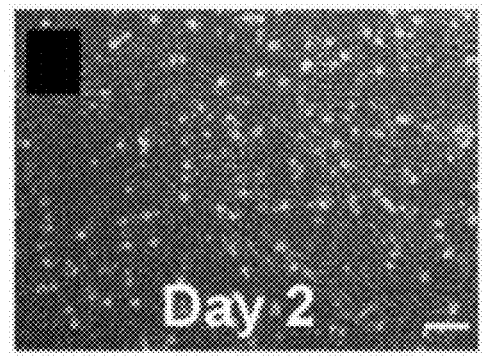
FIG. 3 depicts multipotent germline precursor cells cultured on mouse embryonic fibroblast (MEF) feeder layers in PM-1™ medium supplemented with 15% fetal bovine serum (FBS). At different time points during culture, the number of GFP+ cells was determined using fluorescence-assisted cell sorting (FACS) (FIG. 3A-3D).
FIG. 3E depicts a graph of cell numbers vs. time. Scale bars are equivalent to 60 µm.
Figure 3B:
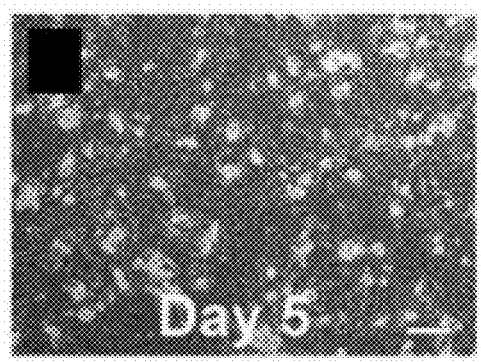
Figure 3C:
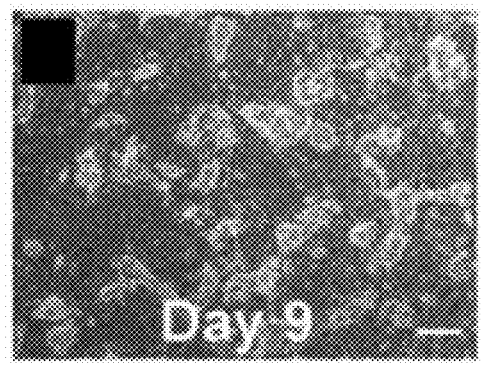
Figure 3D:
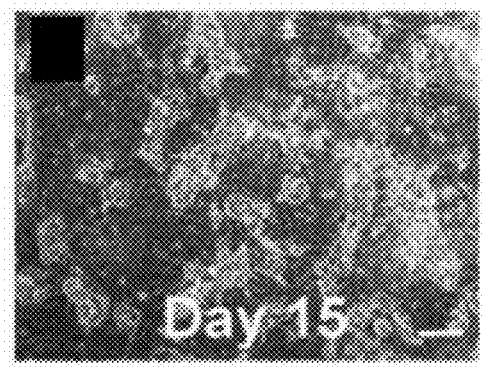
Figure 3E:
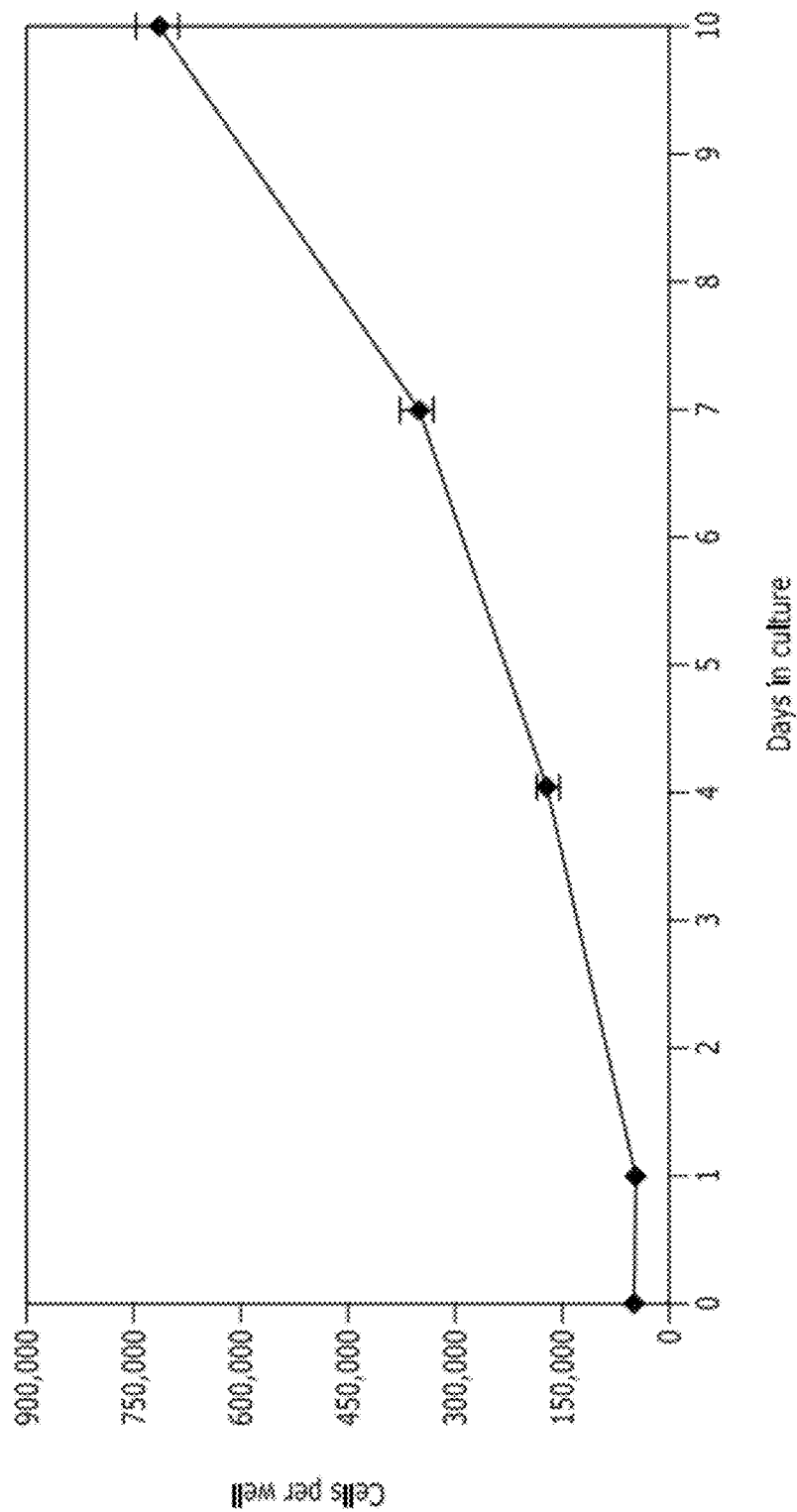

In addition, a mGC line was generated from neonatal wild type CD-1 mice indicating that the method is not limited to transgenic OG2 mice. Selected cell lines were frozen/thawed and propagated for more than 40 passages with an estimated cell doubling time of 72 hr (using both manual cell count and GFP sorting (FIG. 3). At different time points during culture (day 2, FIG. 3A; day 5, FIG. 3B; day 9, FIG. 3C; day 15, FIG. 3D), the number of GFP+ cells were analyzed by FACS (FIG. 3E).

C-Kit+/GFP+ cells were separated from the c-Kit−/GFP+ cells by flow cytometry (FIG. 1D-E) and cultured on MEF feeders. Only c-Kit+ populations generated mGC colonies and no cell line could be generated from the c-Kit− pool. Among the growth factors used in this study, removal of GDNF resulted to smaller colonies indicating the role of GDNF in self renewal of the mGCs. In contrast, removal of FGF2 resulted in differentiation of the colonies, indicating possible role of FGF2 in maintenance of the mGCs in their undifferentiated stage. Removal of LIF or EGF did not affect either the expansion or differentiation of the mGCs.

Figure 4:
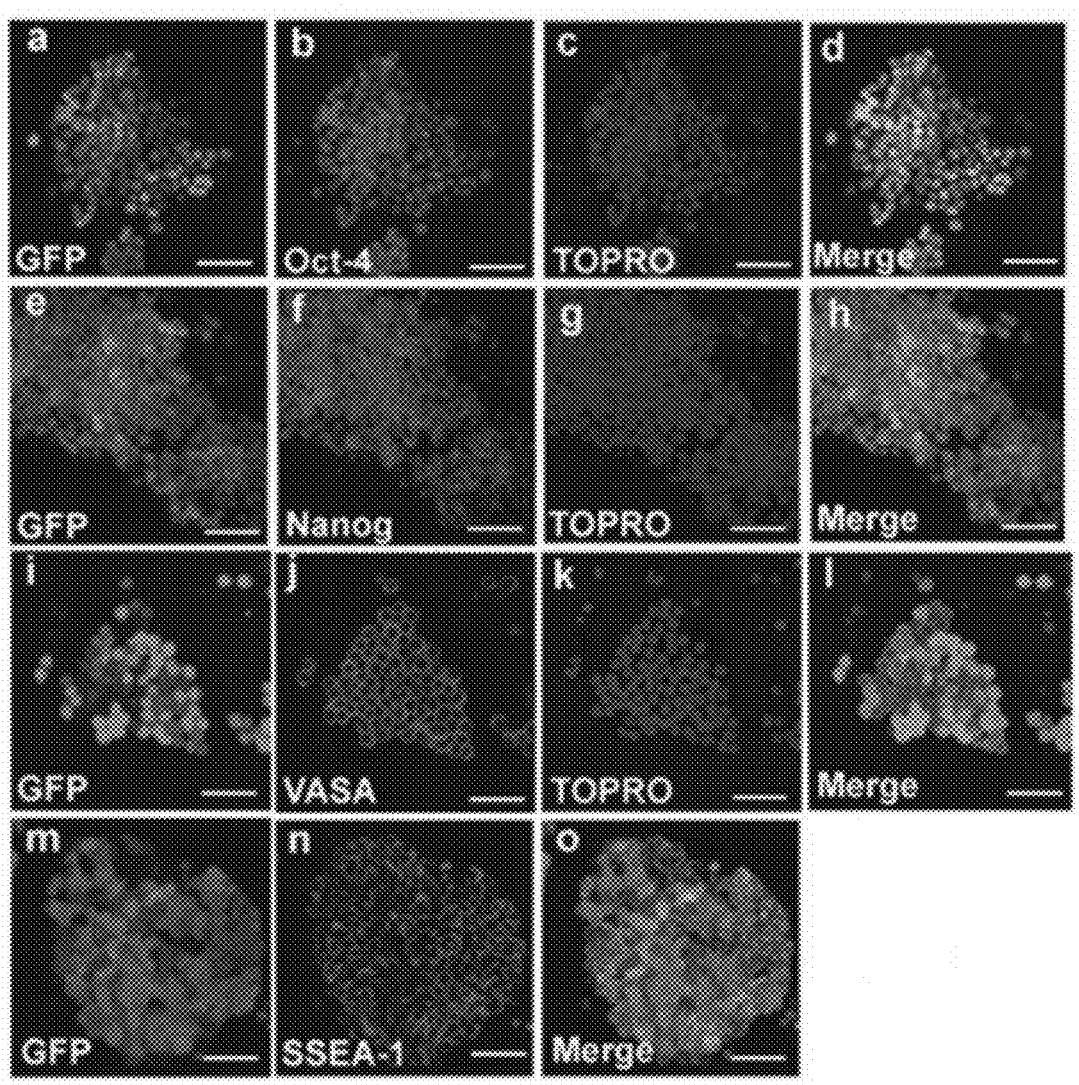
FIG. 4 depicts phenotypic and molecular characterization of mGCs. Immunolocalization of pluripotent and germ cell markers are depicted in FIGS. 4A-4D for Oct-4, FIGS. 4E-4H for Nanog, FIGS. 4M-4O for SSEA-1 and FIGS. 4I-4L for the germ cell marker, VASA. Scale bars.
Figure 4P:
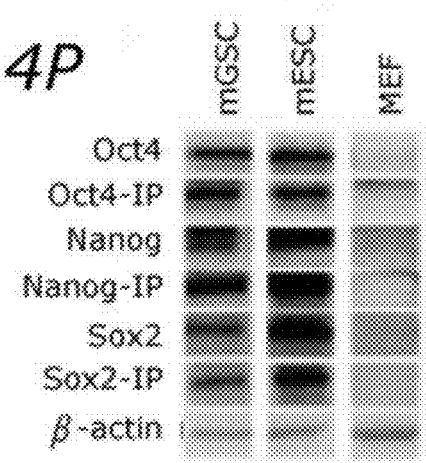
FIGS. 4A-4H: 25 µm.
FIG. 4I-4O: 20 µm. Expression of pluripotent and germ-specific markers determined by RT-PCR is shown in FIG. 4Q. The Western blot analysis of protein contents of Oct-4, Nanog and Sox2 in mGC cells before and after immunoprecipitation (IP) is presented in FIG. 4P.
Figure 4Q:
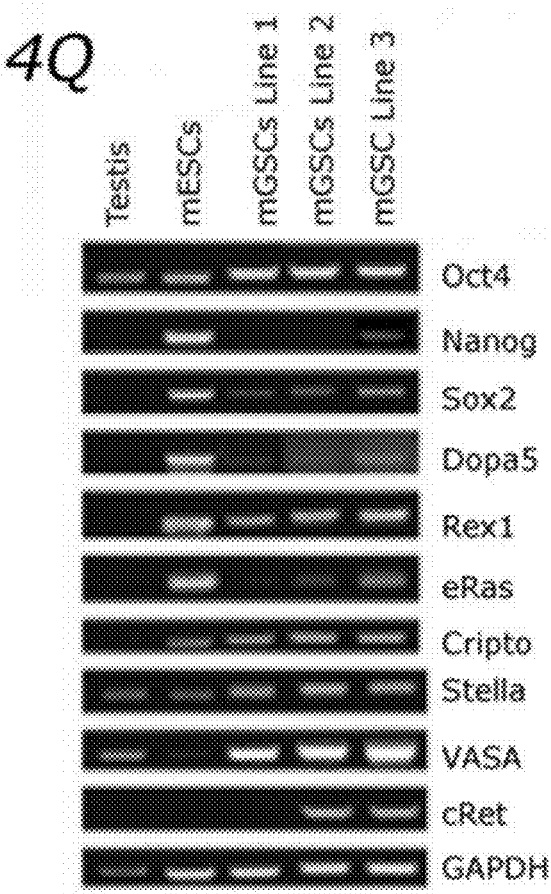

The majority of cells in the mGC colonies expressed Oct-4 (FIGS. 4A-4D), Nanog (FIGS. 4E-4H), VASA (FIG. 4I-4L), and SSEA-1 (FIGS. 4M-4O). They also expressed pluripotent genes Sox2, DPPa5, Rex-1, eRas, and Cripto along with germline specific markers, including Stella, Dazl, Vasa and cRet (FIG. 4Q). In addition, the expression of Oct-4, Nanog and Sox2 was confirmed by Western blot analysis (FIG. 4P).

Figure 5A:
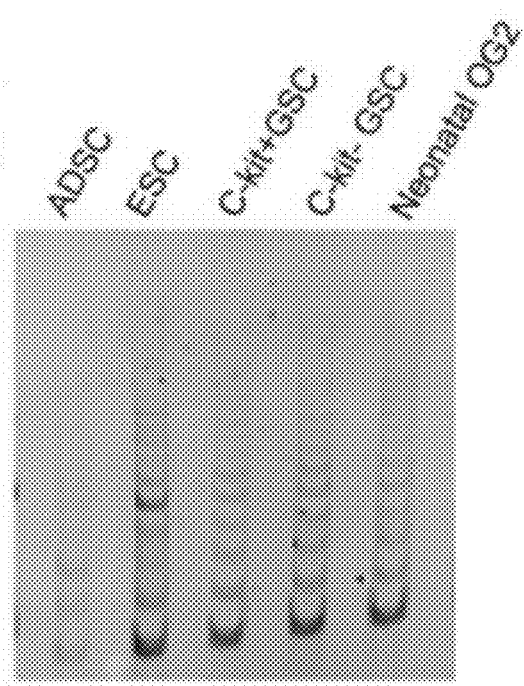
FIG. 5 depicts telomerase activity and karyotype analysis in adult adipose-derived stem cells (ADSC), mouse ES cells, freshly isolated germline stem cells after c-Kit sorting and multipotent germline stem cells at passage 10 (neonatal OG2). The telomerase activity in the germline stem cells is comparable to mouse ES cells and higher than the ADSC cells (FIG. 5A).
FIG. 5B depicts the karyotype of the same neonatal OG2 cell line. The picture is representative of the 80 metaphase spreads that were analyzed. After 15 passages the cells exhibit a normal karyotype.
Figure 5B:
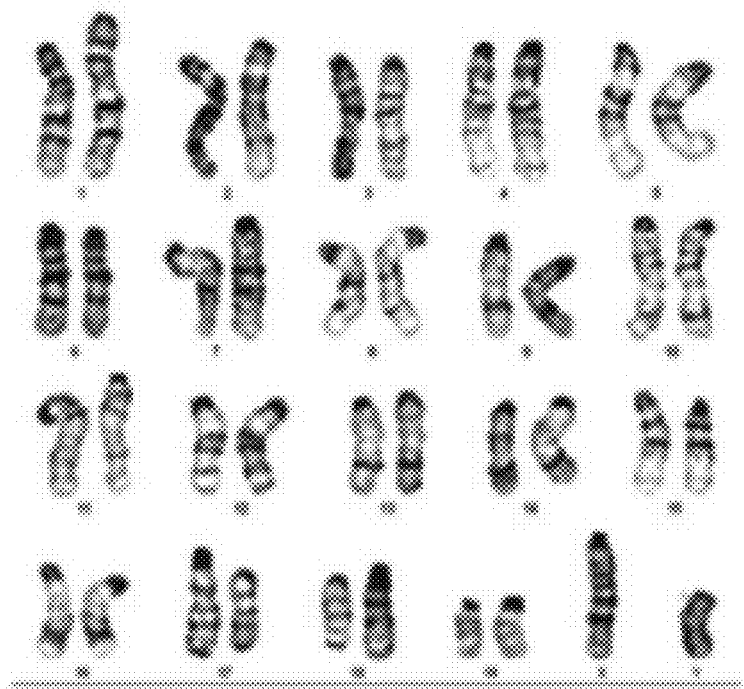

The mouse cell line at passage 20 showed high telomerase activity (FIG. 5A, similar to ESC) and normal karyotype (40, XY) (FIG. 5B).

Figure 6:
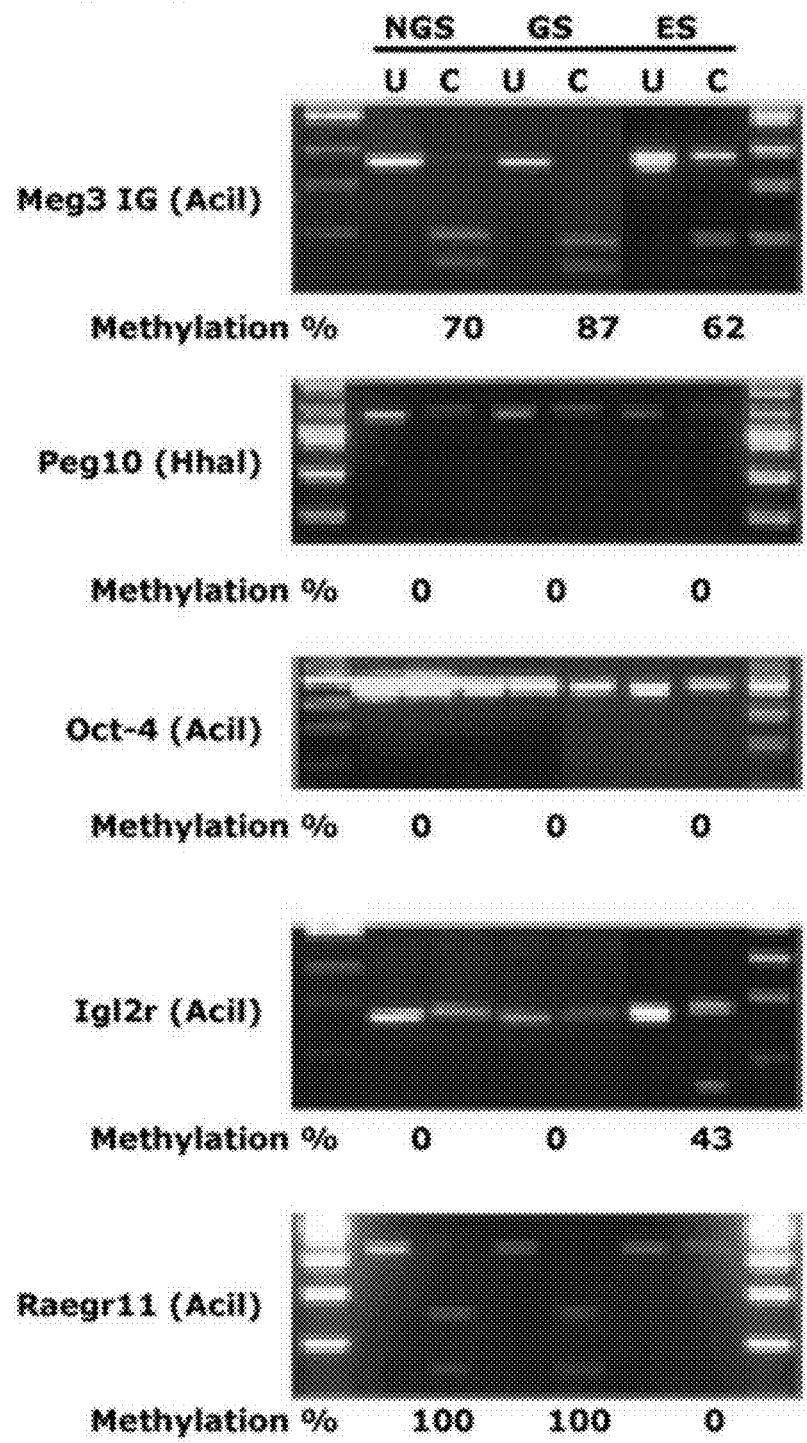
FIG. 6 depicts imprinting analysis of multipotent germline precursor cells before (NGC) and after (GC) culture and compared with mouse ES cells for differentially methylated regions Meg3, Peg10, Oct-4, Igf2r and Rasgrf1.

The global gene expression and imprinting patterns of the mGCs were also analyzed before and after culture and compared with that of ESC. Interestingly, culture conditions did not change the imprinting pattern of the mGCs in all the DMR (differentially methylated region) sites tested. In contrast to mouse ESC that showed only a partial androgenetic imprinting, the mGCs clearly exhibited a 100% androgenetic imprinting pattern (FIG. 6). Somewhat surprisingly, microarray analysis showed that the global gene expression pattern of the mGCs had 87% similarity before and after culture.

Figure 7A:
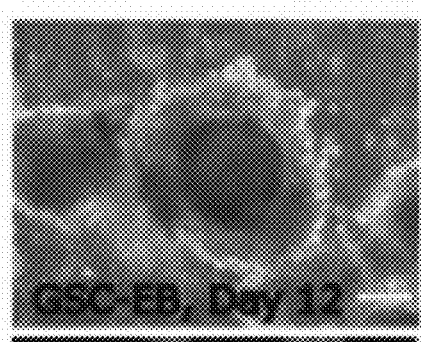
FIG. 7A) and the expression of markers indicative of polarized epithelium (E-cadherin and laminin1.
Figure 7B:
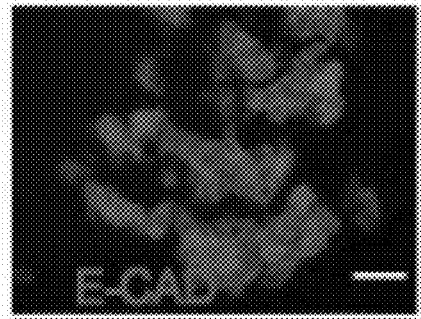
FIGS. 7B-7C) and early development of the three germ layers, i.e., ectoderm (ZIC1, PAX6, SOX1), endoderm (GATA4, FOXA2) and mesoderm (BRACHYURY, BMP4 and COL2A1) are shown in FIG. 7D-7F. During culture reprogramming mGCs also differentiated spontaneously into cardiomyocytes (FIG. 7G-7J), adipocytes (FIG. 7K) and neural cells (FIGS. 7L and 7M). Scale bars.
Figure 7C:
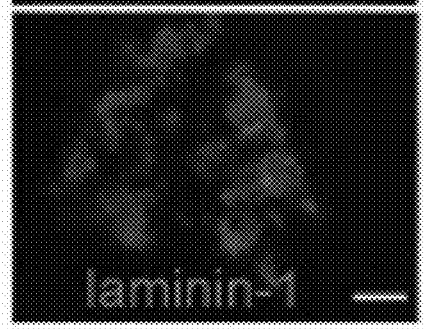
Figure 7D:
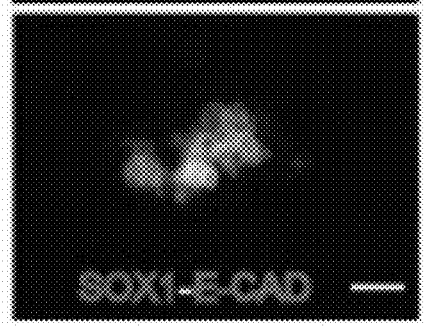
Figure 7E:
Figure 7F:
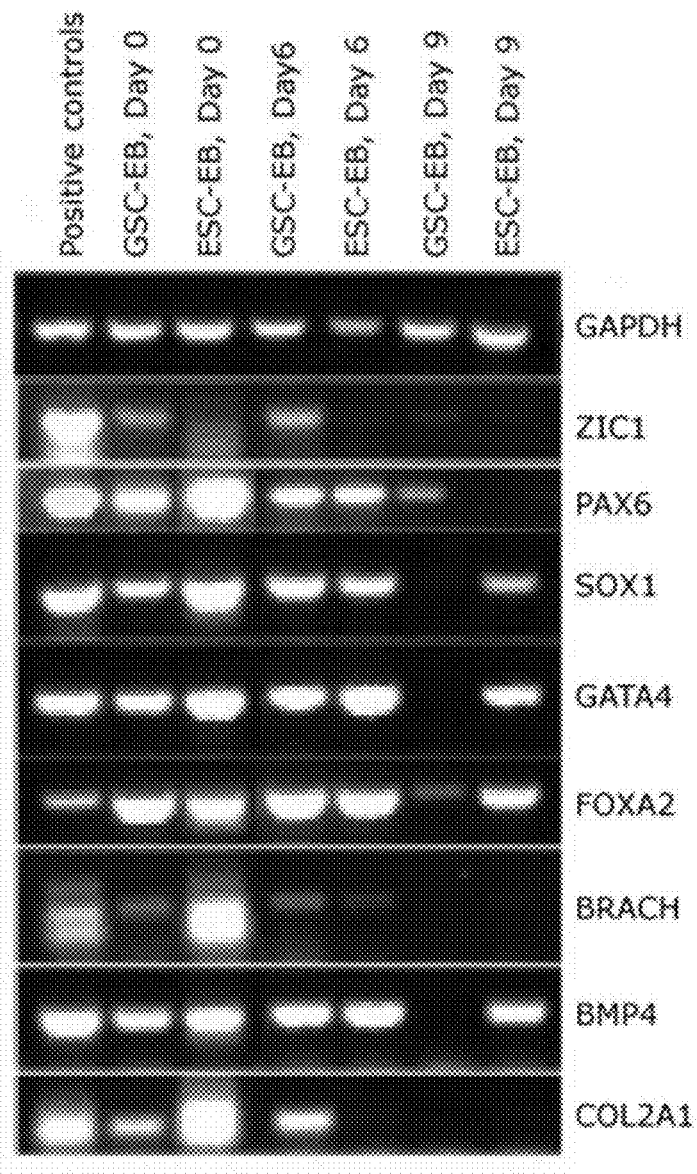
Figure 7G:
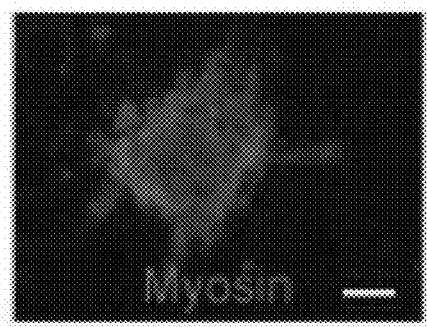
FIGS. 7G, 7H and 7L: 45 µm.
Figure 7H:
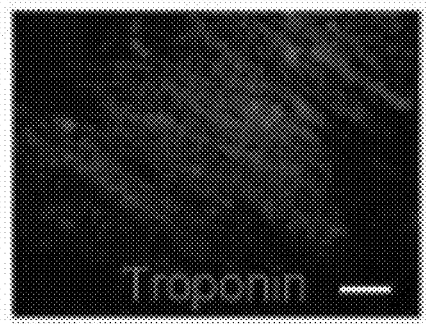
Figure 7I:
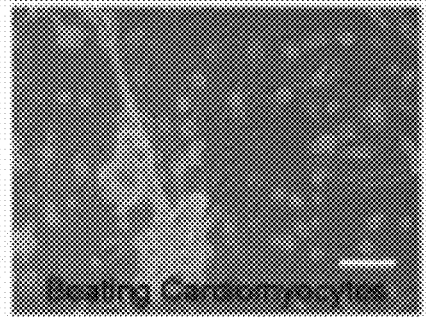
Figure 7K:
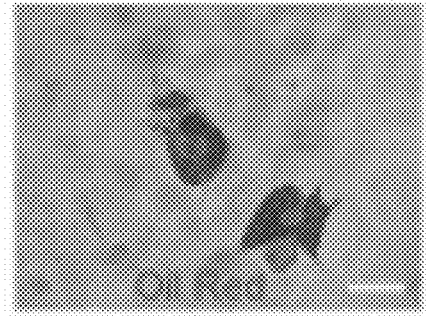
FIG. 7K: 12 µm.
Figure 7L:
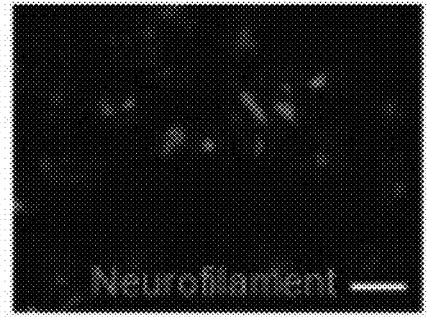
Figure 7J:
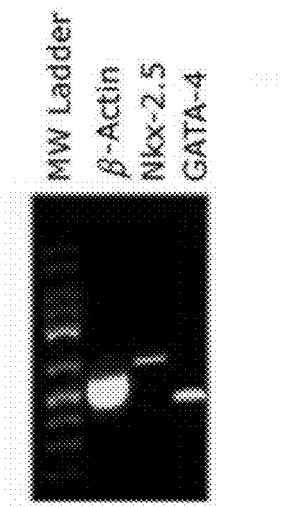
Figure 7M:
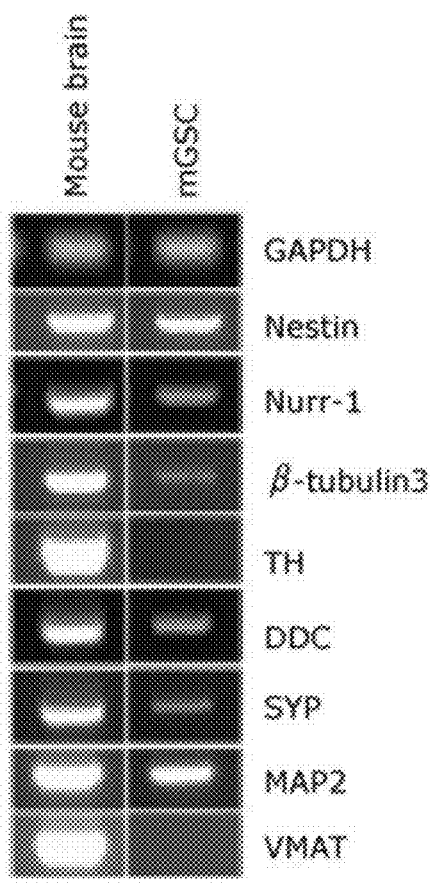

When mGCs were aggregated to form embryoid bodies (EBs), gastrulation was observed within 9-15 days (FIG. 7A). Cells in the EBs expressed early developmental markers including E-cadherin and laminin1 (markers of polarized epithelium (FIG. 7B-7C), Zic1, PAX6 and Sox1 (early ectoderm markers, FIGS. 7D and 7F), GATA4 and FoxA2 (early endoderm markers, FIG. 7E-7F), and Brachyury, BMP4 and COL2A1 (early mesoderm markers, FIG. 7F). In culture, mGC colonies spontaneously differentiated into phenotypes expressing markers of cardiomyocytes (FIG. 7G-7J), adipocytes (FIG. 7K) and neural cells (FIGS. 7L and 7M). Some of the cells that spontaneously differentiated to cardiomyocytes exhibited rhythmic contractions for up to 3 days. Using directed differentiation protocols, mGC lines could be induced to differentiate into neural cells representing neural progenitors (nestin, neuroD1), neurons (MAP2, NF-68, GAD67) and glial cells (GFAP, MBP, A2B5, O4, NG2) as shown in FIGS. 8A-8G and 8J. They could also be induced to form cardiomyocytes (troponin1, cardiac myosin, desmin, Nkx2.5, GATA4, FIGS. 8I and 8L) or chondrocytes (collagen Xa1, and staining by alcian blue, FIGS. 8H and 8K).

In a separate differentiation study with mGCs, the number of cells (nuclei) were counted with and without staining of neural markers in seven colonies within a culture and the average percentage was estimated as 17.6% for GFAP$^+$ cells, 2.5% for Tuj-1$^+$ cells and 2.3% for MAP-2$^+$ cells. In general, the efficiency of induced differentiation by these protocols was much higher in ES cells compared to the mGCs.

Figure 9:
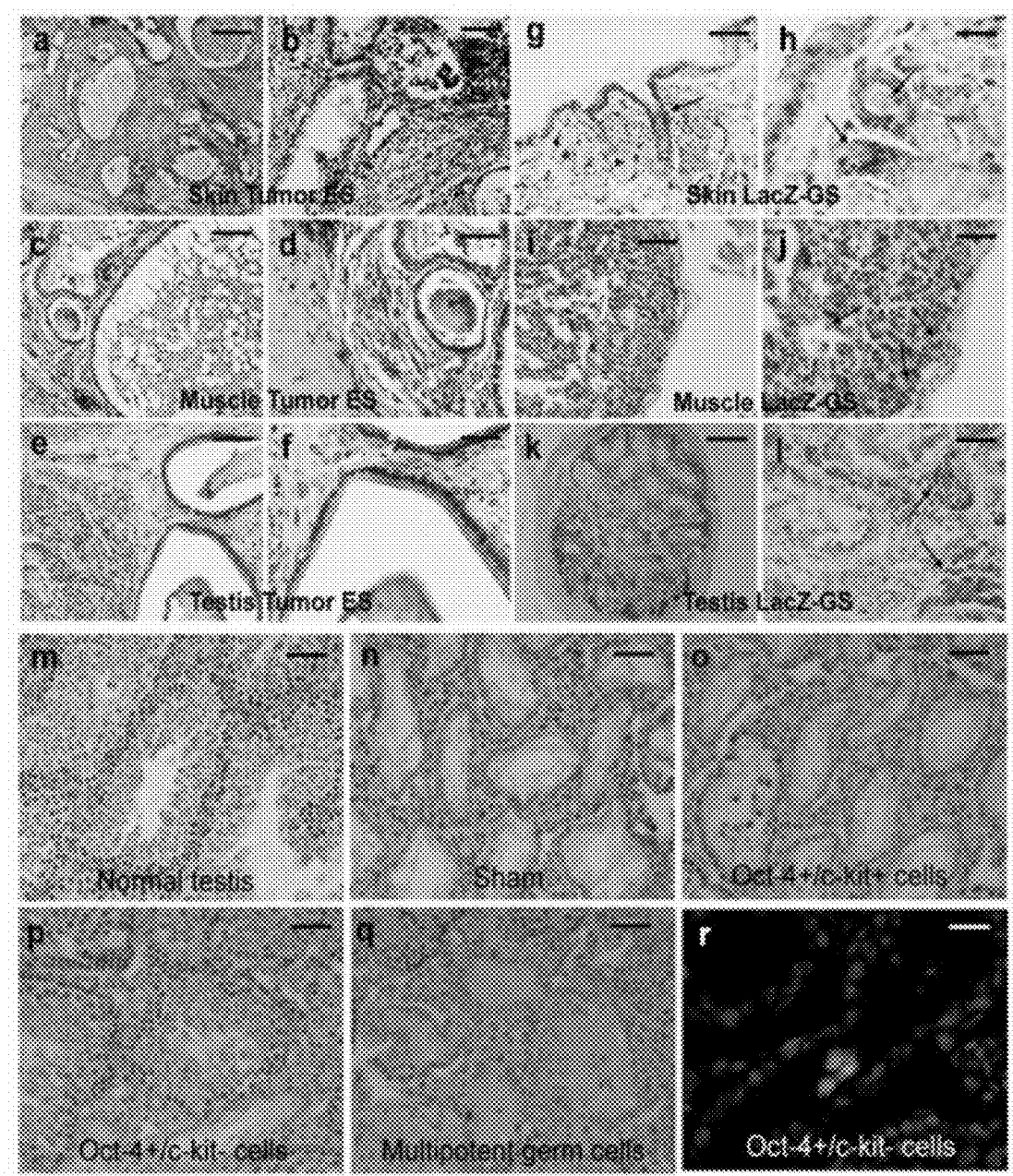
FIG. 9 depicts the formation of teratomas after transplantation of mouse ES cells (FIG. 9A-9F) but not multipotent LacZ-GFP mGCs (FIG. 9G-9L) into the skin, muscle and testis. The morphology of ESC-derived teratomas was identified by H&E staining on thin paraffin sections, whereas the fate of transplanted multipotent germ cells (mGCs) was identified by LacZ staining shown in blue. Six weeks after transplantation, GFP-LacZ$^+$ mGCs were found in the skin (in the bulge area of hair follicles and adjacent sebaceous glands, arrow head.

Four weeks after transplantation, testes of the control animals as well as those which received Oct-4+/c-Kit+ cells showed no spermatogenesis in the majority of the seminiferous tubules. However, 80% of the mice which received freshly isolated Oct-4+/c-Kit-testicular cells showed some degrees of spermatogenesis throughout the testes, indicating the presence of functional SSCs in the cell suspension. Only the c-Kit– subpopulation of germline stem cells colonized the recipient testes. Testes regeneration following transplantation of germline stem cells before and after culture in presented in FIGS. 9M-9R and Table 1. Cross section of the normal testis of an immune-deficient mouse is depicted in FIG. 9M. One month after busulfan treatment, the majority of the seminiferous tubules were depleted from endogenous spermatogenesis (FIG. 9N). While 73% of seminiferous tubules of mice transplanted with Oct-4+/c-Kit– cells showed some degree of spermatogenesis (FIG. 9O), the majority of tubule cross-sections of the mice receiving Oct-4+/c-Kit– cells were empty (FIG. 9P). A CSFE-tagged positive colony shortly after transplantation of Oct-4+/c-Kit– cells is depicted in FIG. 9R. No spermatogenesis was found in the majority of seminiferous tubules of the recipient mice testes transplanted with the mGCs, indicating these cells do not have SSC properties (FIG. 9Q).

TABLE 1

Restoration of spermatogenesis following transplantation of subpopulations of germline stem cells and multipotent germ cell lines in recipient mouse testes

| Transplanted cells | Total No. of tubule cross sections analyzed | Total No. of tubules with spermatogenesis (%) | Total No. of empty tubules (%) |
|---|---|---|---|
| Oct-4+ | 580 | 328 (56.5)$^b$ | 252 (43.5) |
| Oct-4+/c-Kit+ | 440 | 68 (15.5)$^a$ | 372 (84.5) |
| Oct-4+/c-Kit– | 580 | 448 (77.2)$^c$ | 132 (22.8) |
| mGC | 420 | 100 (23.8)$^a$ | 320 (76.2) |
| Sham | 480 | 80 (16.6)$^a$ | 400 (83.4) |

For teratoma formation, equal numbers of mouse ESC (as positive control) or Oct-4-GFP/LacZ mGCs were injected into the skin, muscle and testes of different groups of nude mice (1×10$^6$ cells/site). All recipient mice (6/6) receiving ESC developed teratomas in all three tissue types. In contrast, none of the mice (0/20) receiving mGCs gave rise to teratomas (FIGS. 9A-9F). Six weeks after transplantation, Oct-4-GFP/LacZ cells, were found in skin, muscle and testicular tissues (FIGS. 9G-9I). These data show that mGCs, unlike ESC, are non-tumorigenic.

Figure 10:
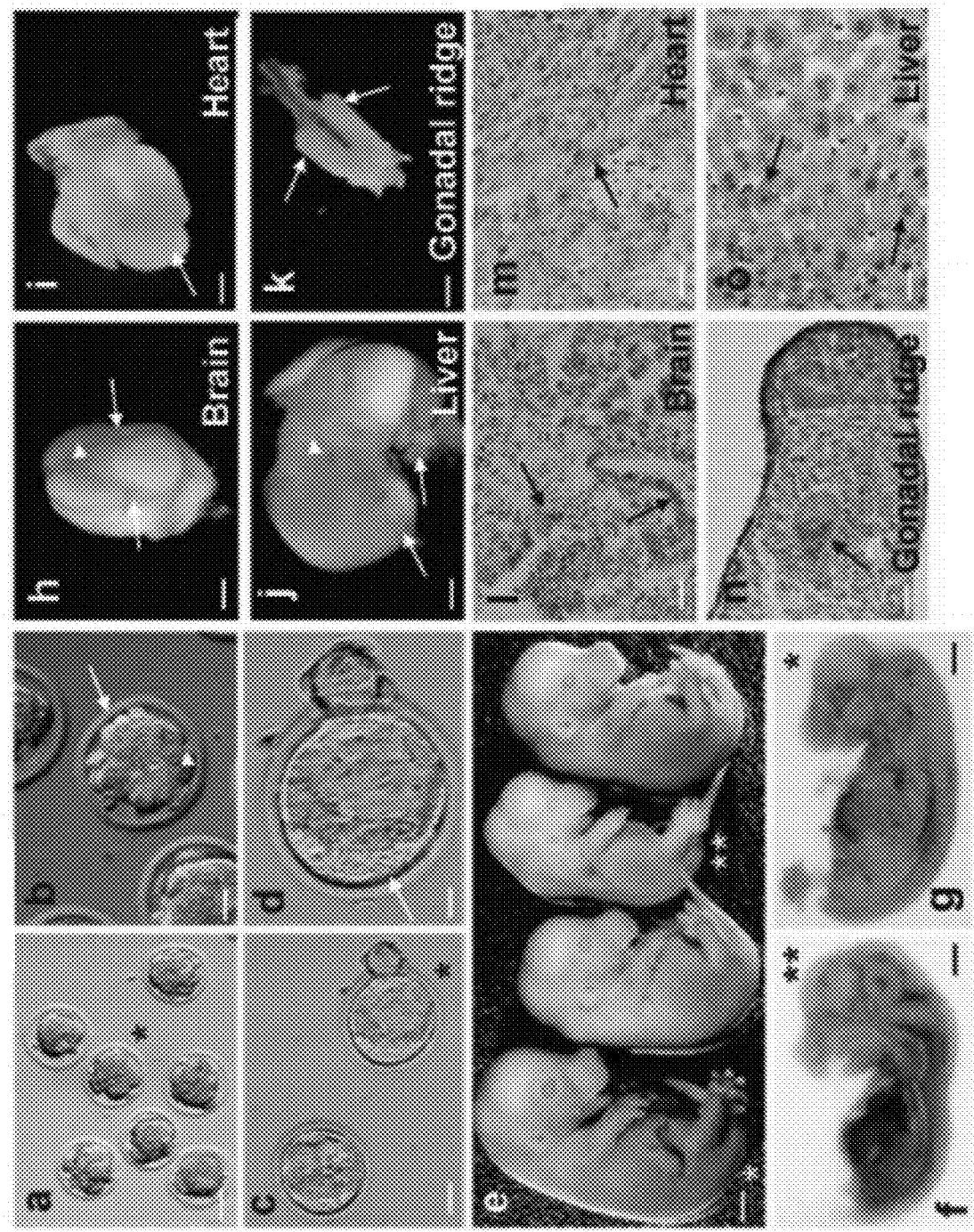
FIG. 10 depicts chimera formation after incorporation of mGCs into blastocysts and host embryos. The incorporation of LacZ-GFP$^+$ mGC cells during early embryonic development and blastocyst formation is presented in FIG. 10A-10D. The majority of the GFP-lacZ cells injected at 8-cell stage have been incorporated at day two of the embryonic development (arrow head) and some cells have not been incorporated yet (arrows). GFP+ cells were further found at day 3.5 incorporated in inner cell mass (arrow) of the blastocyst. An example of four chimeric embryos showing different degree of chimerism is shown in FIG. 10E as whole embryo staining. To visualize the internal organs, sagital sections of two of the embryos (indicated by asterisks) are also shown (FIGS. 10F and 10G).
Figures 10P, 10Q:
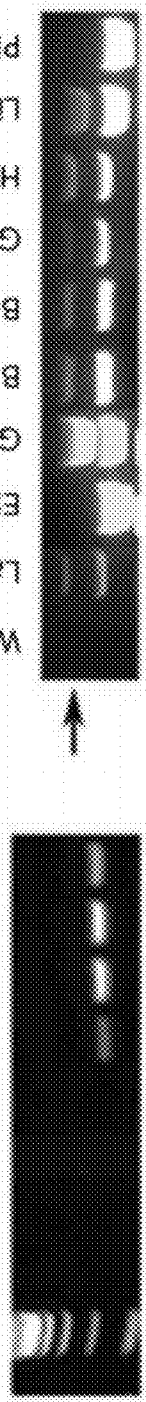

Chimera formation was measured by injecting cultured Oct-4-GFP/LacZ cells into 8-cell embryos and blastocysts of CD-1 mice. As shown in FIG. 10A-10D, Oct-4-GFP/LacZ cells incorporated into the inner cell mass of the mouse blastocysts. The embryos were transferred into the uterus of pseudo pregnant mice (a total of 45 fetuses from 119 transferred embryos). At 12.5 dpc (days post coitus) staining of whole embryos for LacZ (β-galactocidase activity) showed distinctive patterns in the eye, brain, and limbs (FIG. 10E). The intensity of LacZ staining was much higher in chimeric embryos received mouse ES cells than those injected with multipotent germ cell lines. The distribution of chimeric cells is also demonstrated in histological sections of the brain, heart, gonadal ridge and liver (FIG. 10L-10O). The intensity and number of LacZ+ cells was much higher in chimeric embryos injected with LacZ-ES cells than those injected with LacZ-GS cells. Confirmation of Oct-4-GFP/LacZ chimeric tissues was supported by the presence of GFP DNA sequence in the ectodermal (brain), mesodermal (heart), endodermal (liver) and testis of the chimeric pups (FIG. 10P), as well as the presence of LacZ DNA (FIG. 10Q) in all 4 tissues. These combined results clearly demonstrate that cultured mGCs are non-teratogenic stem cells with some pluripotent characteristics.

Multipotent germ cell lines can be generated from adult mouse testes without reprogramming growth factors; indicating the possible presence of a subpopulation of cells with pluripotent characteristics in the adult testes.

Independently, as described supra, germline sex cell lines and germline precursor cells from post-natal mouse germline stem cells were derived with some, but not all, of the pluripotent characteristics of ESC. Both of these cell line types are distinctively different from the multipotent germ cell lines obtained by the other laboratories, most notably, with regard to the extent of pluripotentiality and teratoma formation.

Based on microarray analysis, mouse Oct-4+/c-Kit+ germline cell lines expressed pluripotent genes Nanog and crypto but at 1000-fold and 5000-fold lower levels than in ESC. Similarly, the germ cell lines expressed oncogenes including, but not limited to, p53, Eras, Bak, Int-2 and c-myc, but the expression levels were several fold lower than with ES cells. Remarkably, the germ cell lines did not form teratomas upon transplantation in vivo, but they did form limited chimeric cell populations in mouse embryos.

Several lines of evidence support the notion that the Oct-4+/c-Kit+ germline precursor cells retain their germ cell properties and thereby differ from ESC and other previously reported testicular cells: namely, 1) the derived germline precursor cell lines have a cell cycle time that doubles their cell numbers in about 72 hr (determined by both GFP sorting and manual counting), and this cell cycle time is more similar to that of germline stem cells and is about three times longer than that of the ESC; 2) based on global gene expression analysis in arrays, the instant germline precursor cells seem to have molecular characteristics different from those in ESC or other multipotent germ cell lines. Among the genes tested, the instant germline precursor cell lines showed significantly higher expression level of germline specific genes (Vasa, Plzf, GFR-α1, Dazl) and lower expression level of pluripotent genes (Oct-4, Nanog, Dppa-5, Sox2, Crypto); 3) these cell lines are more dependent on GDNF for their self renewal than LIF or FGF2. GDNF has been proposed to be the key regulator of the self renewal of male germline stem cells, while LIF and FGF2 play crucial role in self renewal of ESC; 4), the expression level of SSEA-1 in these cell lines was lower than the level found either in mouse ES cells or other multipotent germ cell line as reported. It has been shown that SSEA-1 may be involved in tumor invasion and metastasis in certain animal model systems suggesting that higher expression may reflect higher potential for tumorigenesis; and 5) multipotent GCs exhibited an androgenic imprinting pattern that is different from mouse ESC or other mGC lines reported by other laboratories.

Despite of all the similarities to their germline ancestors, the instant germline precursor cell lines did not regenerate testes following transplantation demonstrating that they were not germline sex cells.

The transgenic mouse model allowed the isolation germline stem cells from both neonatal and adult testes based on their Oct-4 expression. The germline stem cells were further fractionated into two subpopulations according to their expression of c-Kit with the following observations: 1) only the Oct-4–/GFP+ cells that possess the c-Kit receptor molecule responded to culture and generated multipotent germ cell lines; and, 2) only the c-Kit– subpopulations repopulated the testis after spermatogonial stem cell transplantation. The results clearly indicate the presence of at least two distinct subset of germline stem cells within reproductive tissues: (1) a c-Kit+ pool with the ability to become multipotent germline stem cells, i.e. germline precursor cells, as well as, (2) a subset of germline stem cells that have lost their c-Kit expression and acquired the ability to colonize the testis, i.e., germline sex cells. Apparently, in adult tissues the germline stem cells in the reproductive organs are either present in different developmental stages, or alternatively, they possess differing abilities to respond to growth factor signaling and/or transcription factors.

Materials and Methods

Isolation of Testicular Cells.

The testes of either neonatal mouse pups (2-5 days after birth) or adult mice were sterilely removed from the body. The capsule of the testes was removed and the seminiferous tubules were suspended in an enzyme solution consisting of 1 mg/mL collagenase 1A and 10 units/mL DNase in PBS. The testes were digested at 37° C. in a water bath until all tubules were digested. The reaction was stopped with Fetal Bovine Serum (FBS).

Preparation of Mouse Embryonic Fibroblast (MEF) Feeders:

MEFs were made by standard procedures using 12.5 dpc CD-1 mouse embryos. The embryos were eviscerated before trypsinization, and the dissociated cells were plated onto 150-mm plates with plating density at approximately 1.5 embryos per plate. After the initial plating, MEFs were split 1:5 and then frozen (passage 1). Thawed MEFs (P1) were passed only once for expansion purposes prior to mitomycin C treatment. MEF feeders were plated in a density of $50\text{-}60\times10^3$ per $cm^2$. New MEF feeders were used for pluripotent germ cell culture every 7-10 days. All the animal experiments followed the guide lines for the care and use of laboratory animals (National Research Council).

Evaluation of Telomerase Activity and Karyotyping:

For determination of telomerase activity, cell extracts were isolated from germ cell lines (passage 10 and higher), freshly isolated Oct-4+/cKit+ sorted cells and Oct-4+/c-Kit– sorted cells using CHAPS lysis buffer containing 150 U/ml RNase. Cell lysates were centrifuged for 20 min at 12,000× g, 4° C. and the supernatants were stored at –80° C. Protein concentration was assayed with Bradford reagent using BSA as a standard. Telomerase activity was detected by PCR-based assay using TRAPEZE Detection Kit (Chemicon). Two microliters of cell extract at 750 µg/µl was added to a total volume of 50 µl PCR reaction mix containing TRAP Reaction Buffer, dNTPs, substrate oligonucleotide, telomerase primer, internal standard primer, and Taq polymerase. As positive control, 2 µl of mESC cell extract was added to the reaction mix, and CHAPS lysis buffer alone and heat inactivated telomerase were used as negative control for each experimental sample. Each sample was incubated at 30° C. for 30 min for telomerase extension, followed by PCR amplification. For karyotyping, proliferating cells were incubated in culture with 0.1 µg/ml KaryoMAX Colcemid (Invitrogen) for 3-4 hr before they were re-suspended in hypotonic solution (0.075M KCL) and incubated at room temperature for 10 min. Cells were then resuspended in cold fixative (3:1 methanol:acetic acid) and stored at 4° C. for at least 30 min. Following washing with fixative, cells were applied to clean glass slides and air dried. Metaphase chromosomes were prepared and karyotypes created using an Applied Spectral Imaging Band View digital imaging system.

In Vitro Differentiation:

For generating embryoid bodies (EBs), mGSC colonies were dissociated with collagenase and plated in non-adhesive culture plates in PM™ medium (disclosed in co-pending U.S. patent application Ser. No. 11/488,362 filed Jul. 17, 2006 and incorporated by referenced herein for all it contains regarding tissue culture media) containing 15% FBS. In some experiments EBs were formed in hanging drops. EBs, for differentiation into cells representing the three germ layers, were cultured for 15 days with samples taken out every three days for marker determination. For induced differentiation, the EBs were cultured in PM medium for four days before they were cultured in the serum-free N1 medium for lineage selection: i.e., DMEM/F12 (Invitrogen) supplemented with ITS (insulin, 10 mg/l; transferrin, 5.5 mg/l; selenium, 0.67 mg/l) and fibronectin (50 µg/ml). After 5-7 days, N1-treated cell aggregates were transferred to gelatin-coated culture plates in N2 medium for expansion of neural progenitor cells (N1 medium with ITS, without fibronectin and supplemented with 10 ng/ml bFGF). For differentiation into cardiomyocytes, EBs were cultured for two weeks in the presence of different cardiogenic compounds including 0.06 M DMSO, 5 mM 5'-aza-2'-deoxy-cytidine (AZA) and 25-50 µM cardiogenol-C. During the differentiation process, the morphology of cells was analyzed and samples were taken both for gene expression analysis by RT-PCR and immunohistochemical staining. Chondrocyte differentiation of mGSCs was induced by adding a chondrogenic induction medium (Chondrogenic SingleQuots, Cambrex) supplemented with 10 ng/ml TGF-3β and 20% FBS.

Immunocytochemical (ICC) and Immunohistochemical (IHC) Staining:

Cultured cells were fixed in 4% paraformaldehyde for 10-30 min at room temperature and stored in PBS at 4° C. For fluorescent immunocytochemistry, cells were permeablized with 1× Cytoperm (BD Biosciences) or 0.2% Triton X-100 for 15 min and subsequently incubated in 2% (w/v) bovine serum albumin (BSA), 2% (v/v) normal goat serum (GS)/1× Cytoperm-PBS for 30-60 min both at room temperature. Primary antibody was either diluted at the optimal concentration in 2% BSA 2% GS/1× Cytoperm-PBS and incubated for 3 hr at 4° C., or diluted in blocking buffer overnight at 4° C. After two washes, fluorescent secondary antibody was diluted accordingly in 2% BSA/2% goat serum/1× Cytoperm-PBS and incubated for 1 hr at 4° C. in the dark. Cells were washed twice in PBS, wrapped in foil and stored at 4° C. until microscopic analysis. Images were recorded using an Olympus IX71 microscope or Ziess LSM510 confocal microscope equipped with digital image hardware and software.

For brightfield immunocytochemistry, cells were washed once in 1×PBS. Endogenous peroxidase activity was blocked with 3% (v/v) $H_2O_2$ for 15 min followed by permeabilization, blocking with 2% BSA/2% GS/1× Cytoperm-PBS for 30 min. Primary antibody was diluted accordingly in 2% BSA/2% GS/1× Cytoperm-PBS and incubated for 3 hr at 4° C. The remainder of the staining was accomplished using ABC staining kits according to the manufacturer's instructions. Visualization was with enhanced diaminobenzidine (DAB) substrate tablet dissolved in purified water and incubated for 5-10 min. For negative controls, the primary antibody was omitted.

Flow Cytometry:

Specific antibodies, including SSEA-1 and c-Kit were optimized for flow cytometric analysis with an Influx Cell Sorter (Cytopeia, Inc). For c-Kit sorting, freshly isolated testicular cells containing the Oct-4-GFP construct were stained with anti-CD117 APC (BD Biosciences). For some experiments, fresh germ cell colonies were dissociated and cells were stained with anti-SSEA-1 antibody following by goat anti-mouse IgM conjugated with PE-Cy7.

Gene Expression, Imprinting Analysis and GFP Amplification:

Total RNA was isolated using RNeasy Mini Kit (Qiagen) and RNA was used for RT-PCR, Quantitative PCR or Microarray analysis. For RT-PCR, cDNA was synthesized with the Sensiscript RT Kit, and PCR was performed with HotStarTaq DNA Polymerase. All PCR reactions began with an initial incubation at 95° C. for 15 min to activate the enzyme. This was followed by 35 cycles of 95° C. for 15 sec, the appropriate annealing temperature for 1 min and 72° C. for 1 min, which was then followed by 1 cycle of 72° C. for 10 min for final extension. Reactions were carried out using an iCycler™ Thermal Cycler (Bio-Rad). The procedure for RT-PCR was carried out using specific primers including, Oct-4, Nanog, Rex-1, DPPa5, Dazl, β actin, Nkx2.5, Nestin, Mab2, and GFAP. For internal controls, GADPH was used as a house keeping gene for cellular samples and β-actin or interleukin-2 (IL-2) was used in mouse embryos.

Imprinting patterns in mGSCs and mESCs were determined by a PCR-based analysis. PCR amplification of each dimethylated region (DMR) from bisulfite-treated DNAs was carried out by specific primers. For analysis of the imprinted genes the UVP image software was used to quantify the band intensity. For GFP and LacZ amplification, individual tissue from chimeric embryos were carefully collected by dissection, minced into small pieces, and placed in DNA extraction buffer (DNeasy kit) for DNA isolation and purification according to the manufacturer's protocol.

Spermatogonial Stem Cell Transplantation:

To test the functionality of mGCs for regeneration of spermatogenesis, spermatogonial stem cell transplantation was used. Twenty 6-8 weeks immune deficient nude male mice (Harlan) were treated with busulfan (40 mg/kg) and used as recipients. One month after busulfan treatment, $2 \times 10^5$ cells were transplanted into the seminiferous tubules via rete testis injection. Four mice received mGCs (GFP sorted cells). Four other mice were injected with freshly isolated GFP+ sorted cells. Four mice were transplanted with freshly isolated GFP+/c-Kit+ sorted cells, and four mice were injected with freshly isolated GFP+/c-Kit− sorted cells. The remaining four mice served as sham control and were not injected. One month after transplantation, the animals were sacrificed and testes were harvested and used for histological evaluations. To evaluate the efficiency of transplantation, total number of tubular cross sections with spermatogenesis was counted.

Tests for Teratoma and Chimera Formation:

To test the ability of the mGCs to form teratomas or chimeras, OG2 mice (Jackson laboratories) were bred with Rosa 26 mice (Jackson laboratories) and a new strain (OG2-R26) was generated. These mice have both GFP and LacZ constructs in their germ cells. Culture was performed as described and new Oct-4-GFP/LacZ germ cell lines were produced for testing teratoma and chimera formation. Mouse Oct-4-GFP/LacZ mGSCs were examined for their ability to form teratomas in vivo by subcutaneous, intra muscular or injection into the seminiferous tubules of nude mice. As positive controls for teratoma formation, ES cells were injected in some mice. For subcutaneous, intramuscular or testicular injections, approximately $1 \times 10^6$ cells were injected. Mice were sacrificed six weeks later, and tissues were harvested for morphological and histological analysis.

The ability of mouse Oct-4+/GFP+/LacZ GSCs to form chimeric cell populations was determined after injection into host blastocysts, or by their aggregation with morula-stage embryos or eight-cell stage embryos. Blastocyst injections of 15-20 cells were carried out using day-3.5 blastocysts collected from CD-1 mice. After injection, blastocysts were transferred (7-8 blastocysts in each horn of the uterus) into 2.5-day pseudopregnant CD-1 females, previously mated with vasectomized males. Incorporation of lacZ cells was examined in different areas of the chimeric 12.5 dpc embryos by the β-galactocidase staining kit (Sigma). In addition, lacZ and GFP PCR were performed in DNAs isolated from the brain, heart, liver and gonadal ridges of the chimeric embryos formed from Oct-4-GFP/LacZ cells.

Example 2

Isolation, Identification, and Characterization of Primate Germline Stem Cells

Since quiescent and actively dividing germline stem cells exist as two discrete cell populations in mouse testes (Example 1), the possibility that these two cell populations might also be present in adult primate testes was investigated.

Spermatogenesis is a highly regulated process in which undifferentiated germ cells classified as spermatogonial stem cells (SSC) divide and mature to produce spermatozoa. In rodents, $A_s$ ($A_{single}$) spermatogonia are considered to be the resident stem cells responsible for spermatogenesis as they are capable of both self-renewal and differentiation. Unlike in rodents, histological studies of primate and human cells demonstrate two different distinct types of nuclear staining resident on the basement membrane of the testicular seminiferous tubular epithelium, i.e., designated as $A_{dark}$ and $A_{pale}$ spermatogonia.

Below are described markers and isolation methods for substantial purification of primate testicular germline stem cells.

Rhesus monkey testes were used for characterization of primate germline stem cells. Immunohistochemical examination, surface markers and fluorescence activated cell sorting were used to identify, characterize and substantially purify germline stem cells from adult Rhesus monkey testes. The presence of germline stem cells in each cell population was confirmed using telomerase, RT-PCR and immunohistochemical staining with the germ specific marker VASA and SSC-specific marker GFR-α1. Spermatogonial transplantation was used to define the functional capacities of cell populations before and after enrichment.

Immunohistochemical methods were used to identify, characterize and localize germline stem cells in primate testes. For these studies antibodies specific for extracellular matrix component (ECM) α6-integrin, SSEA-4 and GFR-α1 were used to visibly stain histologic sections of primate testes.

Figure 19:
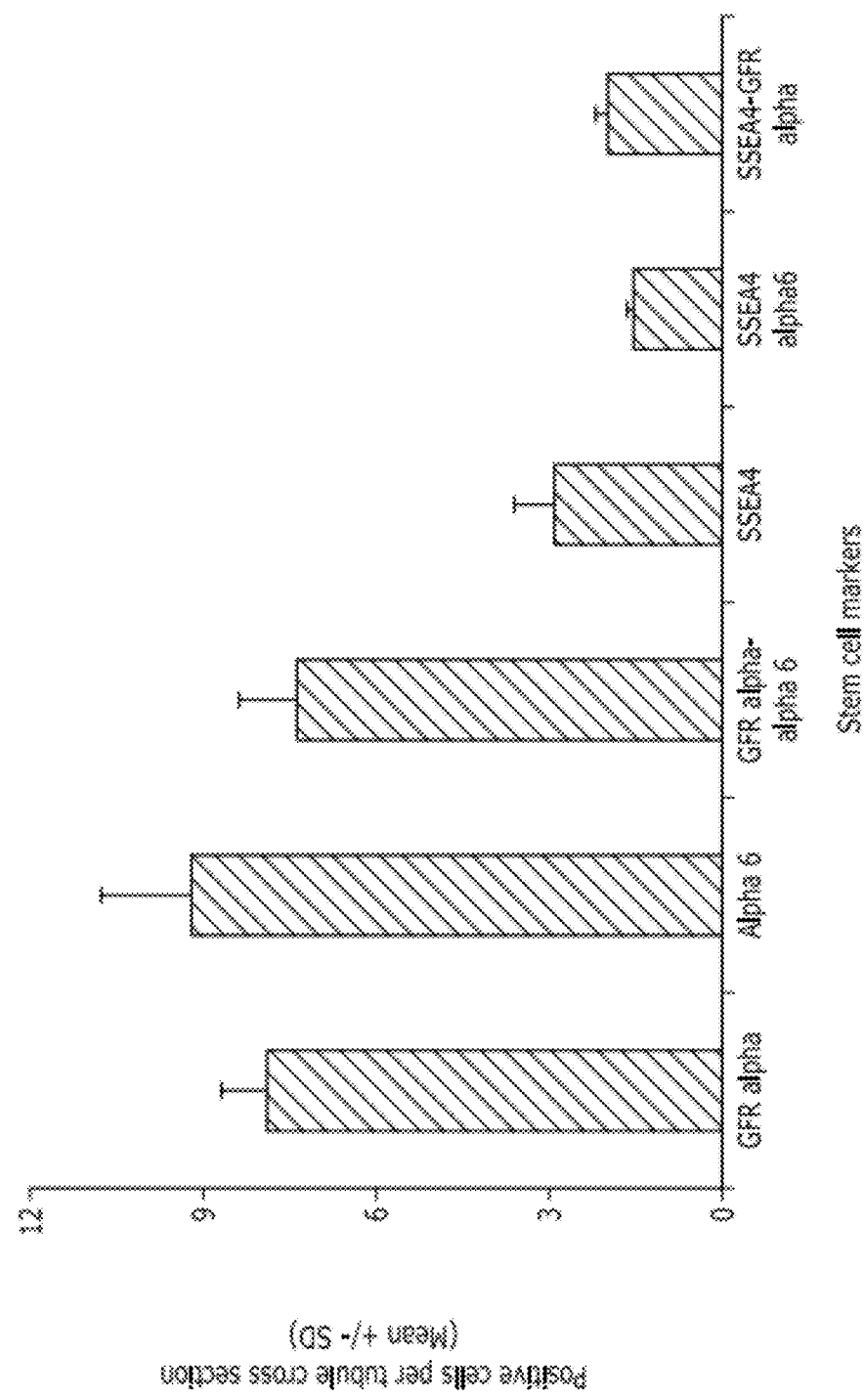
FIG. 19 depicts the distribution of cells positively stained with stem cell markers at the basement membrane of seminiferous tubules of primate testes.

Antibodies specific for α6-integrin stained cells located adjacent to the basement membrane in the seminiferous tubules, as well as the seminiferous tubular basement membrane (FIG. 18). An average of thirteen α6-integrin+ cells was found in each seminiferous tubule histologic cross section. Within seminiferous tubular sections the majority of α6-integrin+ cells were also VASA+, confirming their germline stem cell status. Quantitatively, there were more α6-integrin+ cells per tubular cross section than GFR-α1 and co-localization studies showed that about 60% of α6-integrin+ cells were also GFR-α1+. These combined immunohistochemical studies of primate testis revealed cells adjacent to the basement membrane of the seminiferous tubules which had co-localization of α6-integrin and SSEA-4 cell surface markers and with germ cell specific marker VASA and SSC specific marker GFR-α1, i.e., markers specifically expressed in male germline stem cells (FIG. 19).

The GFR-α-1 cell surface marker was specifically expressed in cells located at the basement membrane of the seminiferous tubules. All of the GFR-α-1+ cells were also positive for germ cell specific marker VASA.

All SSEA-4+ cells were located at the basement membrane of adult primate seminiferous tubules and these cells also were positive for VASA staining. The majority of SSEA-4+ cells were also α6-integrin+. There was also significant co-localization between SSEA-4 and GFR-α1 showing that SSEA-4 is an important cell surface marker for germline stem cells. About 40% of spermatogonial cells at the basement membrane of the seminiferous tubule in primate testes histologic cross-sections expressed SSEA-4.

Very few c-Kit+ cells were found in primate testes. Within tubular cross sections, c-Kit staining was only found in the cells located at the lumen of seminiferous tubules. All c-Kit+ cells were also VASA+ showing that they were differentiated germ cells. No c-Kit staining was found in cells located at the basement membrane of the seminiferous tubular cross sections. These findings indicate that in the primate germline stem cell are c-Kit−.

Nanog was expressed in abundant in primate testes. Nanog appeared as a nuclear staining and was colocalized with VASA in almost all germ cells in seminiferous tubules. Nanog expression was stronger in advanced germ cells located at the lumen of seminiferous tubules compared to undifferentiated germ cells located at the basement membrane. Co-localization study of Nanog and GFR-α1 showed that all the germline stem cells showed a low level of Nanog expression.

CD90 antibodies stained only the basement membrane and did not stain any cellular structure in the testes.

The immunohistochemical characterization of primate testicular samples showed that germline stem cells in the adult primate testes are positive for α6-integrin, SSEA-4 and GFR-α1 and are negative for c-Kit.

Testes from euthanized Rhesus monkeys, age 3-7, were surgically removed; placed in PBS supplemented with penicillin/streptomycin (Cellgro and Invitrogen, respectively) and transported overnight on ice. After surgical removal of the testicular capsule, a biopsy samples were removed for histology and molecular analysis. The remaining seminiferous tubular tissues were finely minced and digested with collagenase A (1 mg/mL) (Roche) and DNase (10 U/mL) (Invitrogen) in a reciprocating 37° C. water bath for 15 min. After collagenase digestion, the undigested tissue was sedimented at unit gravity and cells in the supernatant were removed. The undigested tissue was further digested in an enzyme cocktail consisting of 1.5 mg/mL collagenase A, 1.5 mg/mL hyaluronidase Type V (Sigma), 0.5 mg/mL trypsin (Worthington Biochemical Corporation), and 10 units/mL DNAse in DMEM in a reciprocating 37° C. water bath for 20 min. Digested and undigested tissue were passed through a 70 μm strainer into FBS (fetal bovine serum; Hyclone) to inactivate enzymes. After centrifugation at 400×g for 10 min, the cell pellets were resuspended in DMEM+10% FBS and placed in tissue culture coated 15 cm dishes in a 5% $CO_2$/95% air humidified incubator.

Figure 20:
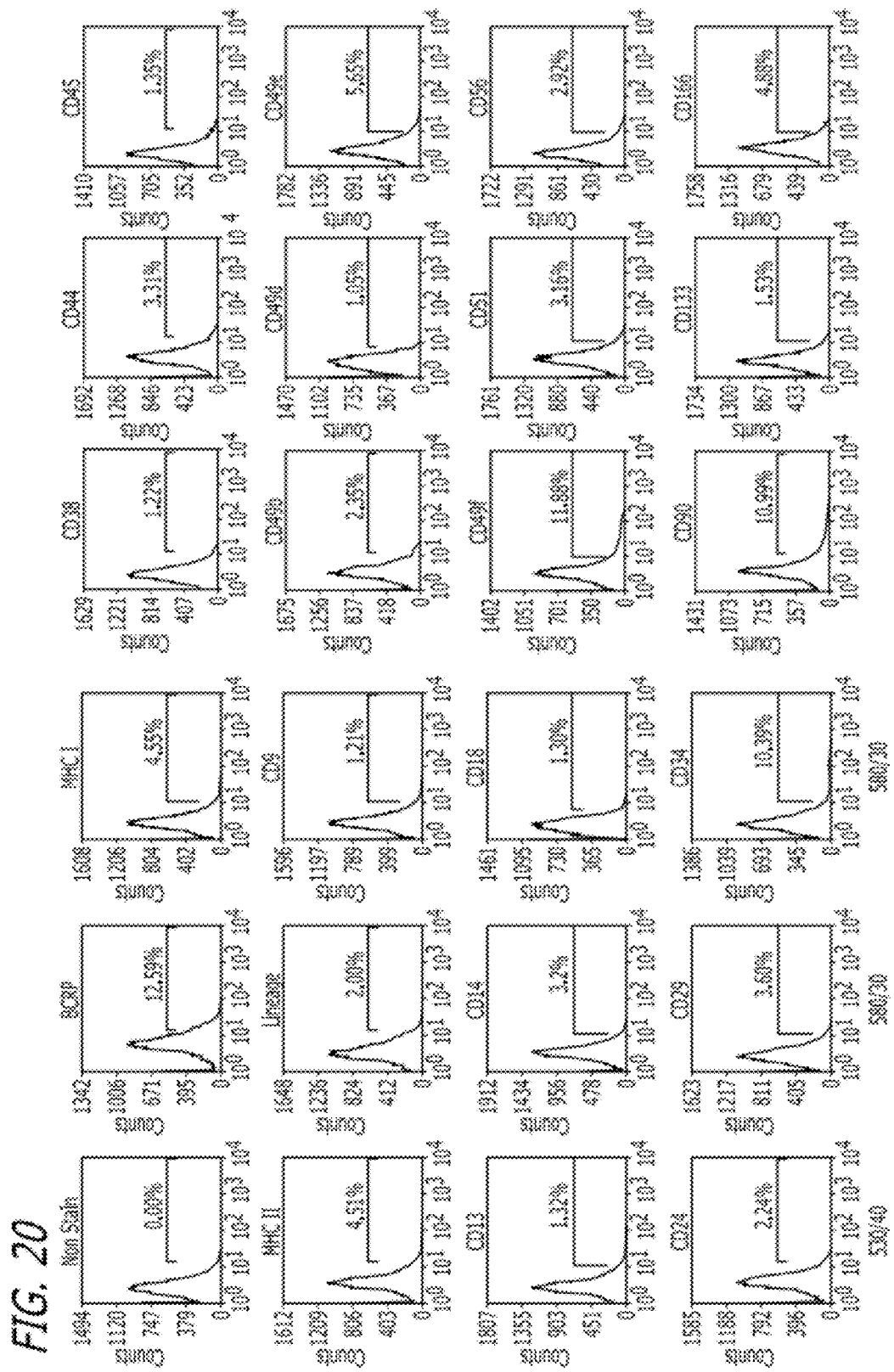
FIG. 20 depicts phenotypic characterization of primate germline stem cells using flow cytometry.
Figure 21A:
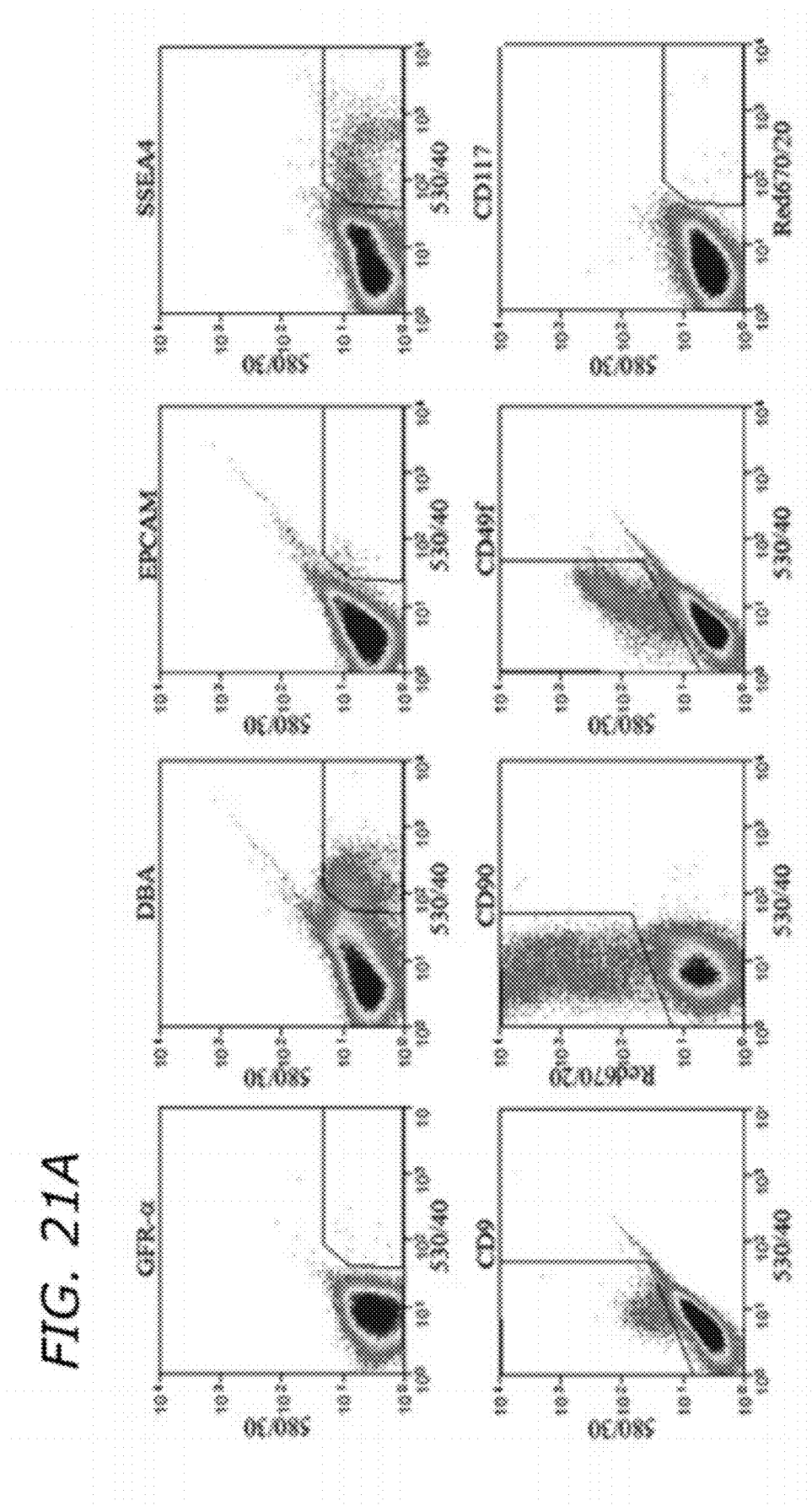
FIG. 21 depicts flow cytometric analysis of primate germline stem cells.
Figure 21B:
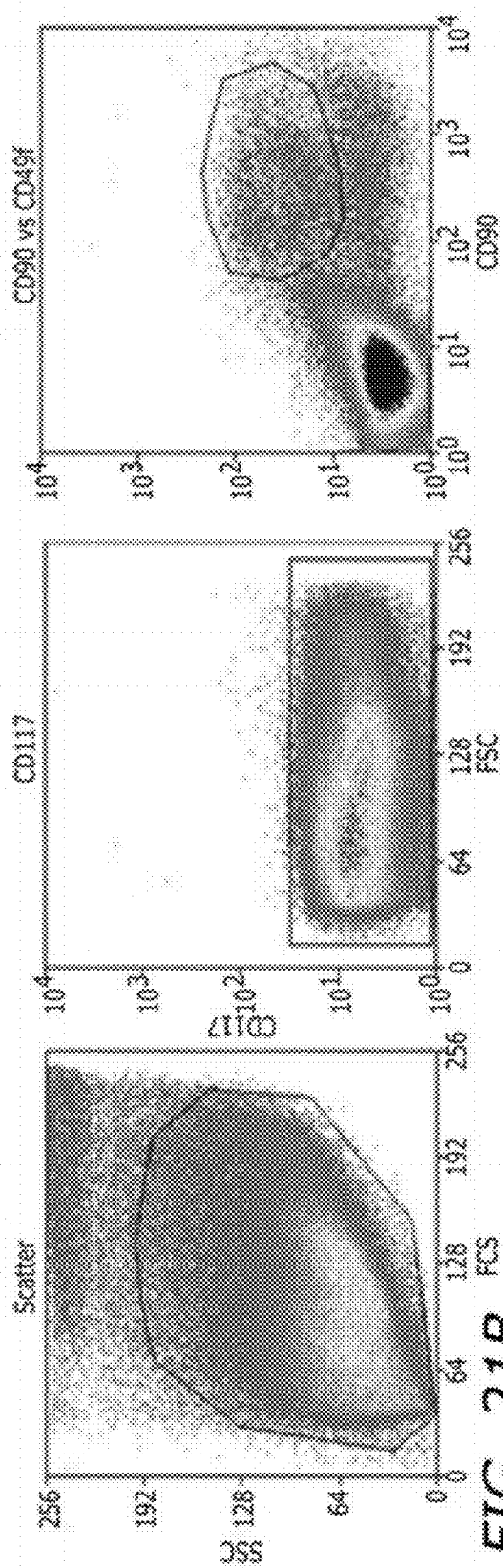
Figure 21C:
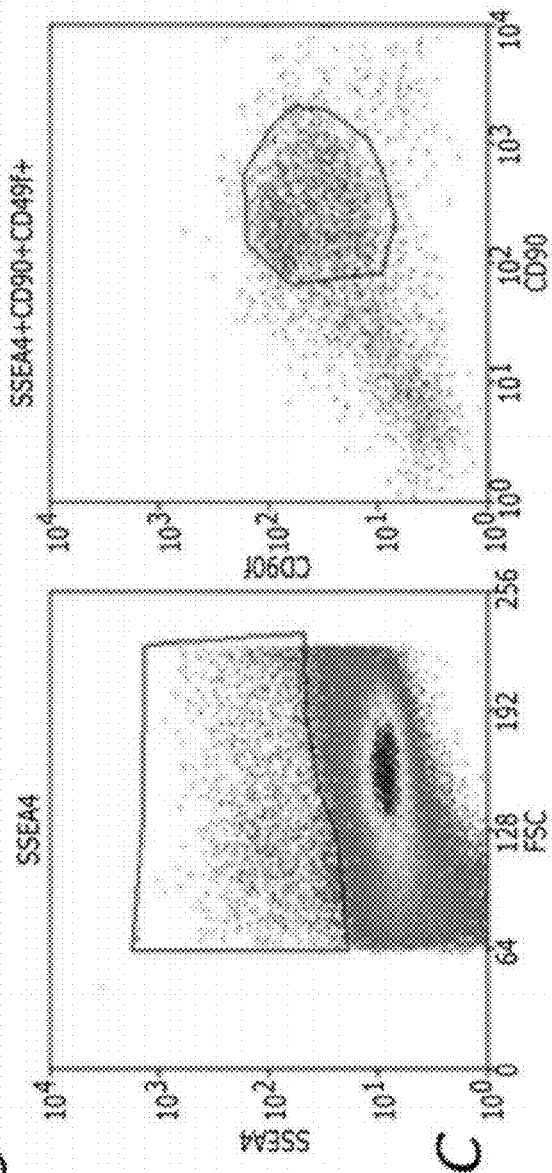

Flow cytometry was used to identify cell surface markers specific for adult primate testicular germline stem cells (FIG. 20). Contrary to reports from other investigators with non-primate SSCs, freshly isolated adult primate testicular cells did not express epithelial cell adhesion/activating molecule (EpCAM). However, germline stem cells were identified as a very small portion of the total adult primate testicular cell population, less than 1% of the total testicular cell isolate, by virtue of expression on their cell surface of the GDNF receptor GFR-α1. Similarly, contrary to experience with murine testicular germline stem cells (Example 1) freshly isolated adult primate germline stem cells did not express c-Kit. However, adult primate germline stem cells, (about 2% of the isolated testicular cell population), expressed cell surface carbohydrate determinants bound by *Dolichos biflourus* agglutinin (DBA), a lectin. In addition, the adult primate germline stem cells expressed the CD9, CD90 and CD49f cell surface markers (FIG. 21).

For isolation of primate germline stem cells, c-Kit was gated as the negative/parent sorting window against which were plotted both CD90+ and CD49f+ to identify the double positive CD90+/CD49f+ cells. Sorting for double positive cells resulted in isolation of germline stem cells, present as about 5.77% of total cells in the adult primate testicular isolates. The latter CD90+/CD49f+ double positive cells were collected for further use. Additional purification was achieved by selecting for c-Kit− cells that were positive for SSEA4, resulting in isolation of a second substantially purified cell population that constituted about 2% of the total adult primate testicular cells. A yet additional purification was achieved by selecting for c-Kit− cells that were positive for all of CD90, CD49f and SSEA4, resulting in isolation of a third substantially purified cell population that constituted about 1.47% of the total adult primate testicular cells.

These combined flow cytometric analysis resulted in isolation and substantial purification of two discrete germline stem cell populations from adult primate testis with the following properties: namely, (a) Thy-1+ and α6-integrin+ cells and (b) SSEA-4+ cells expressing both GFR-α1 and VASA cell surface markers and high telomerase activity, cell populations where more than 50% of the cells were positive for both GFR-α1 and VASA cells.

Figure 22:
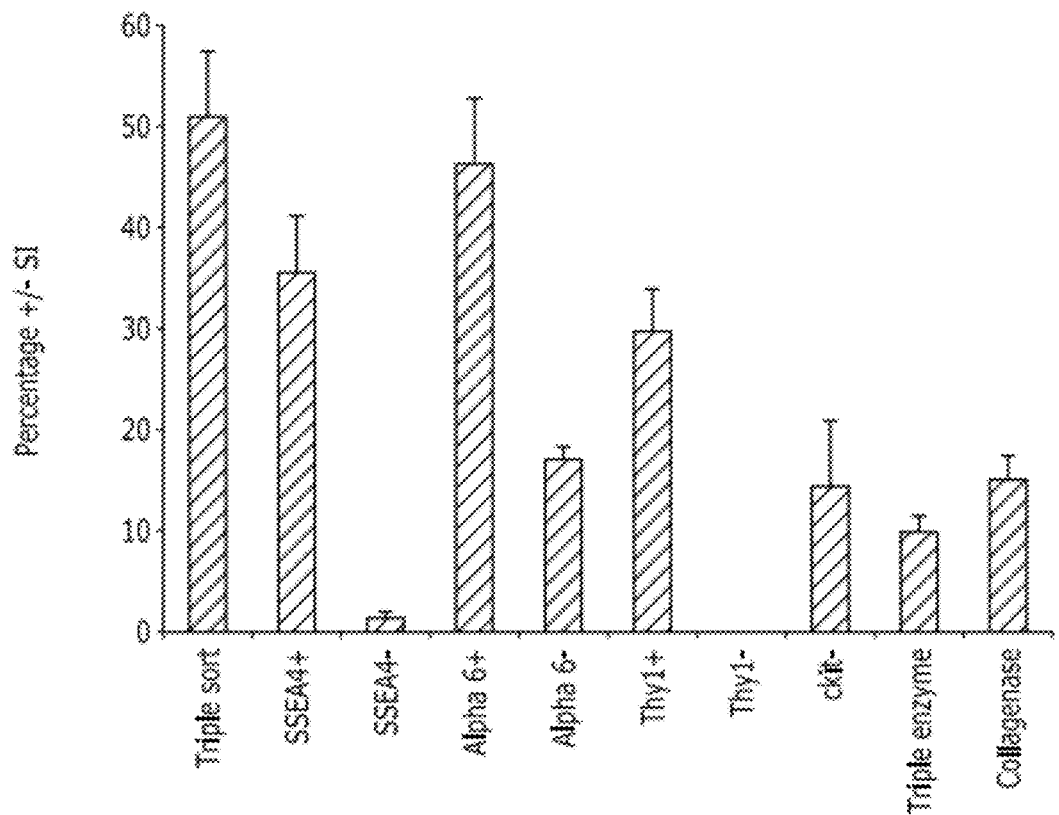
FIG. 22 depicts GFRα+/VASA+ cells in different enriched primate germline cell populations.

To further extend the flow cytometric analysis and immunohistochemical staining freshly isolated adult primate testicular cells were sorted as follows: (i) α6-integrin+; (ii) CD-90+; (iii) CD-90+/α6-integrin+/c-Kit− (triple sort); and (iv) SSEA-4+ cells. The different isolated and purified testicular cell populations were tested for the presence of germ cell marker VASA and SSC marker GFR-α1 (FIG. 22). Non-sorted cells contained about 70% VASA+ cells, but only 10% of these cells stained positive for GFR-α1. Sorting for just α6-integrin resulted in a significant increase in cells with both germline and SSC markers, i.e., populations with 42.6% VASA+ and GFR-α1+ cells. Sorting for CD-90 alone or in combination with c-Kit− (triple sort) also significantly increased the proportion of VASA+/GFR-α1+ cells to 30% and 46.4% respectively. Sorting for SSEA4+ alone, also resulted in an enrichment for cells expressing germline and SSC markers, i.e., sorted cell populations in which 37.5% of the cells were VASA+ and GFRα-1+.

The functional properties of different primate testicular cell populations were determined before and after substantial purification by testing for their ability to repopulate the basement membrane of seminiferous tubules in the testes of immunodefficient nude mice treated with the chemotherapeutic drug busulfan. For these studies nine 6 to 8 week old athymic nude male mice were treated with busulfan (40 mg/kg). One month after busulfan treatment, $2 \times 10^5$ adult primate testicular cells were transplanted into the seminiferous tubules via rete testis injection. For these studies, three mice received a transplant consisting of freshly isolated non-sorted cells; three mice received a transplant consisting of freshly isolated c-Kit−/SSEA-4+ sorted cells; and, three mice received a transplant consisting of freshly isolated c-Kit−/SSEA-4− sorted cells.

To better identify transplanted primate cells in the recipient mouse testes, the vital dye carboxyfluorescein diacetate succinimidyl ester (CSFE) was used as a fluorescent marker. CSFE is a colorless and non-fluorescent compound until the acetate groups are cleaved by intracellular esterases, yielding a highly fluorescent product. The latter fluorescent product was well retained and was fixed with aldehyde fixative, however, the fluorescent intensity diminished exponentially with each cell division. For this vital staining, cells were collected and washed once in 1×PBS containing 1% BSA; then, once in 1×PBS; followed by incubation in 8 μM CSFE in 1×PBS at 37° C. for 10 min. The resultant vital stained cells were washed with MEMα (Invitrogen) containing 2% FBS; collected by centrifugation at 400×g for 5 min; re-suspended in media, and counted.

Figure 23:
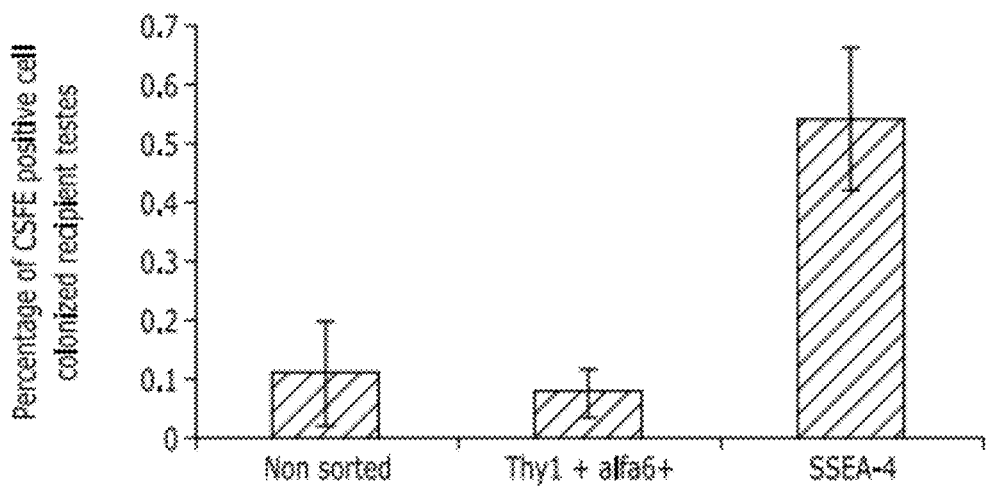
FIG. 23 depicts the carboxyfluorescein diacetate succinimidyl ester (CSFE) activity of subpopulations of primate germline stem cells.

Two weeks after transplantation, mice were sacrificed and the number of CSFE+ cell colonies was determined microscopically in histologic sections of the mouse testes (FIG. 23). Theoretically, if germline stem cells have a cell cycle time of about 72 hr, at two weeks post-transplantation the cells should have undergone 2-3 cell doublings, resulting in colonies of about 4-8 cells. For statistical analysis the ANOVA test was applied and p<0.05 was considered significant.

Figure 24:
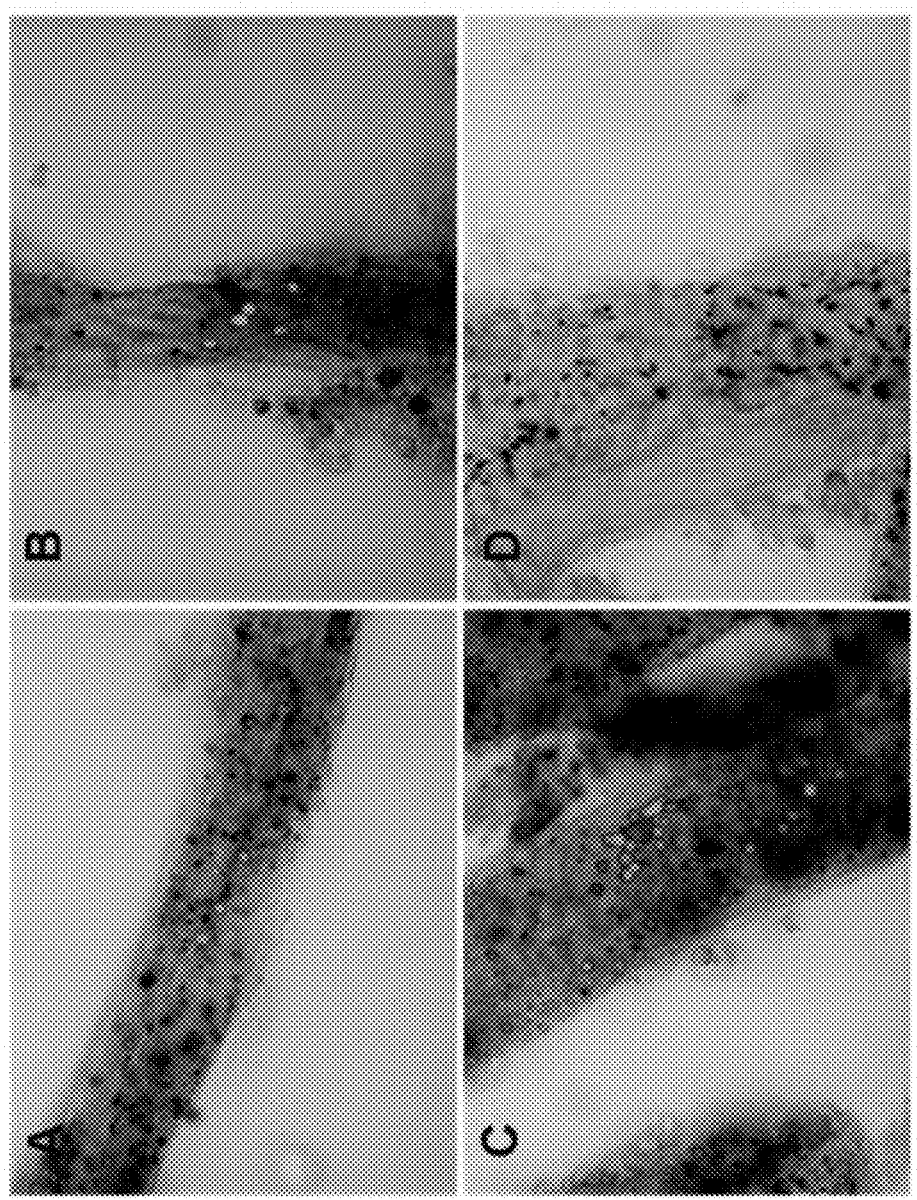
FIG. 24 depicts repopulation of busulfan-treated primate testes with primate germline stem cells: seminiferous tubules of recipient mice transplanted by non sorted cells (FIG. 24A); cells sorted by triple markers (FIG. 24B); SSEA-4+ sorted cells (FIG. 24C); and sham transplanted control testes (FIG. 24D).

These combined transplantation studies showed that only the SSEA-4+ cell population, containing cells expressing GFR-α1 and VASA markers, had the ability to repopulate the busulfan-treated mouse testes (FIG. 24). These findings show that these cells are primordial germline stem cells.

Figure 25:
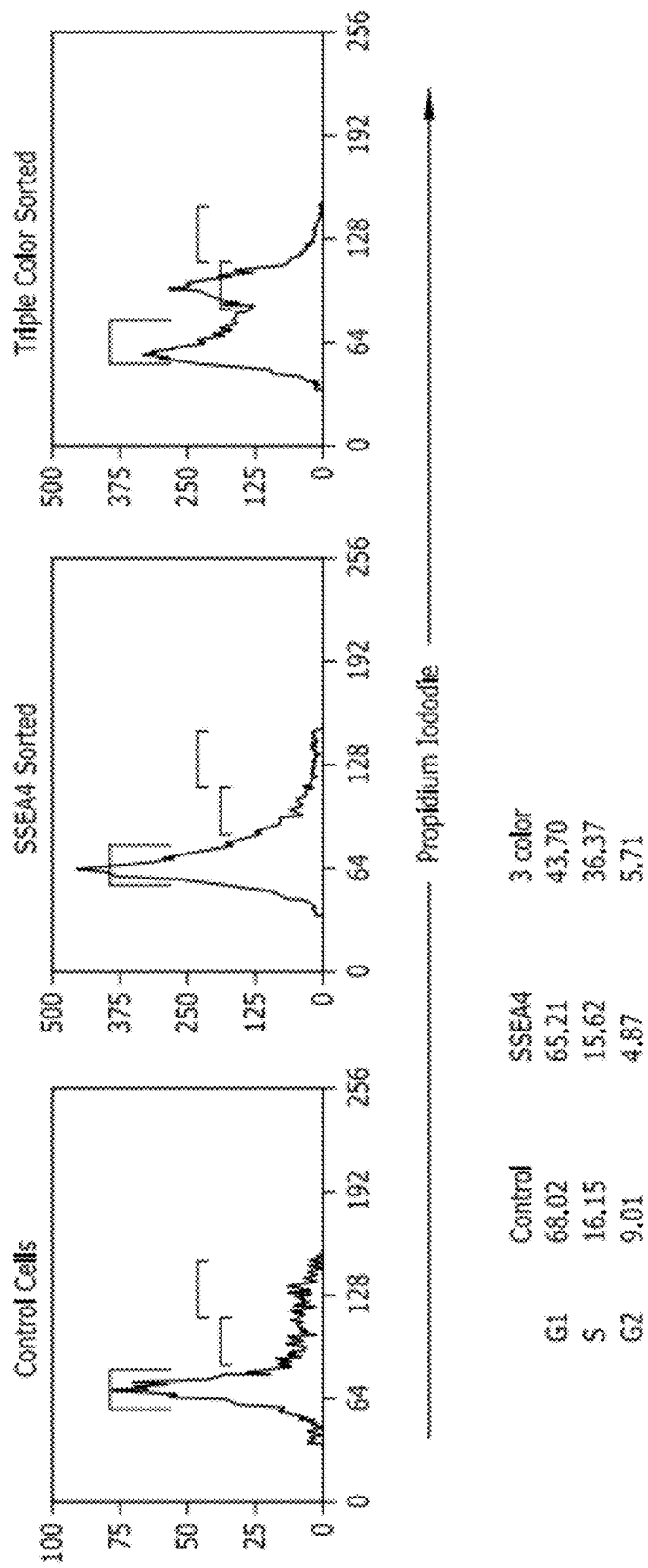
FIG. 25 depicts the DNA content determined by flow cytometry of propidium iodine stained populations of primate germline stem cells.
Figure 27:
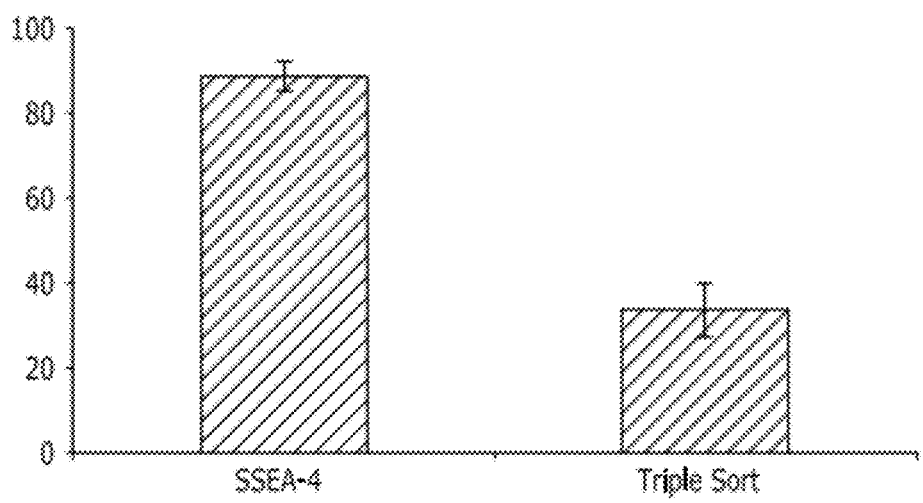
FIG. 27 depicts the percentages of proliferating primate germline stem cells determined by proliferating cell nuclear antigen (PCNA).

To investigate the cell division status of the respective cell populations, the DNA content of the two populations was investigated using flow cytometry (FIG. 25). This analysis showed that the SSEA-4+ cell population had a cellular DNA content resembling that of cells in G0-G1 stage of the cell cycle. In contrast, cells having the Thy-1 and α6-integrin cell surface markers had two discrete and different DNA contents, resembling either the G0-G1 stage of the cell cycle or the S phase. The data show that SSEA-4+ cell population with SSC cell surface markers represents a quiescent population of progenitor germline stem cells, while the Thy-1+ and α6-integrin+ population of cells represents an actively dividing population of SSCs (FIG. 27).

The results show clearly that germline spermatogonial stem cells in the adult primate testis possess molecular and phenotypic characteristics similar but distinct from SSC in rodents. Immunohistological examination using a variety of stem cell, germ cell and spermatogonial stem cell specific markers revealed that in the primate GFR-α1 is specifically expressed at the surface of spermatogonial stem cells along the basement membrane of the semniferous tubules. GFR-α1 is the receptor for GDNF which is an important regulator of self renewal of SSC. GFR-α1+ cells were VASA+ indicating that they are germ cells. Colocalization of α6-integrin with GFR-α1 was 80% in cells located within adult primate seminiferous tubules. Cell populations enriched by selecting α6-integrin+ cells showed a very high level of co-localization with GFR-α1, confirming the findings using immunohistochemical methods to identify germline stem cells in testes sections. Expression of α6-integrin on primate SSC indicates that this marker is conserved among the species as mouse, marmoset and human SSC also possess this marker on their cell surface. Localization of some α6-integrin+ cells within interstitial cells outside the tubules indicates that this marker alone can not be used for isolation of highly pure populations of SSC from adult primate testes.

Figure 26A:
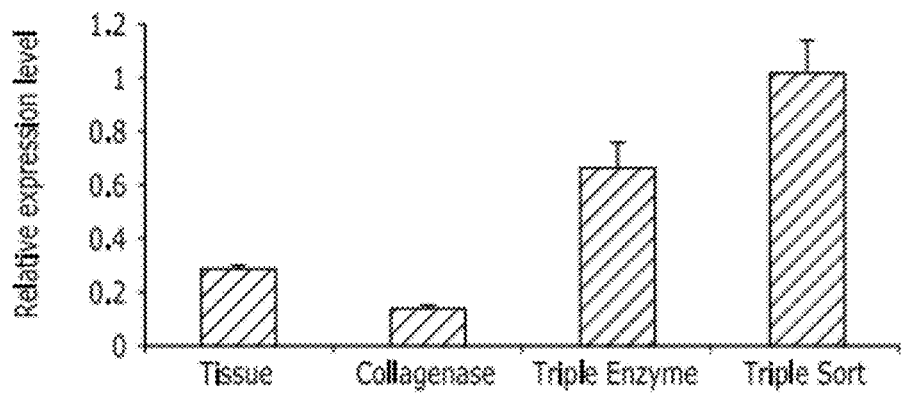
FIG. 26 depicts the quantitative PCR analysis of PLZF expression (FIG. 26A) and telomerase activity (FIG. 26B) in primate germline stem cells.
Figure 26B:
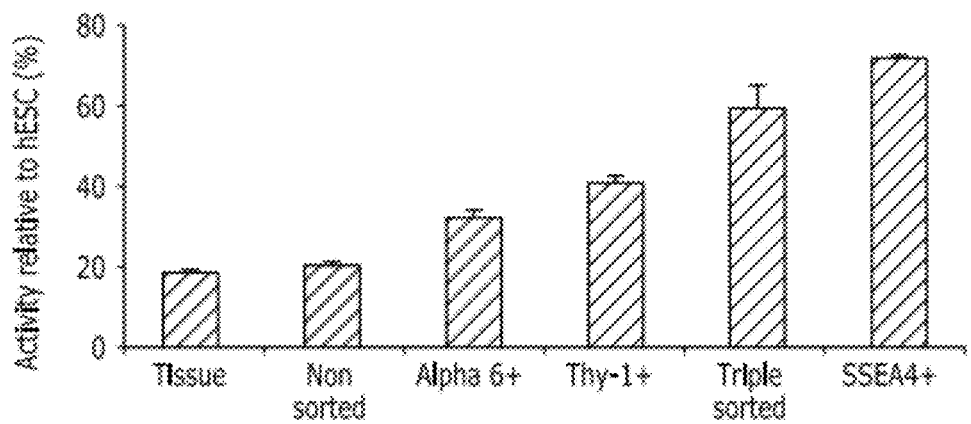
Figure 28:
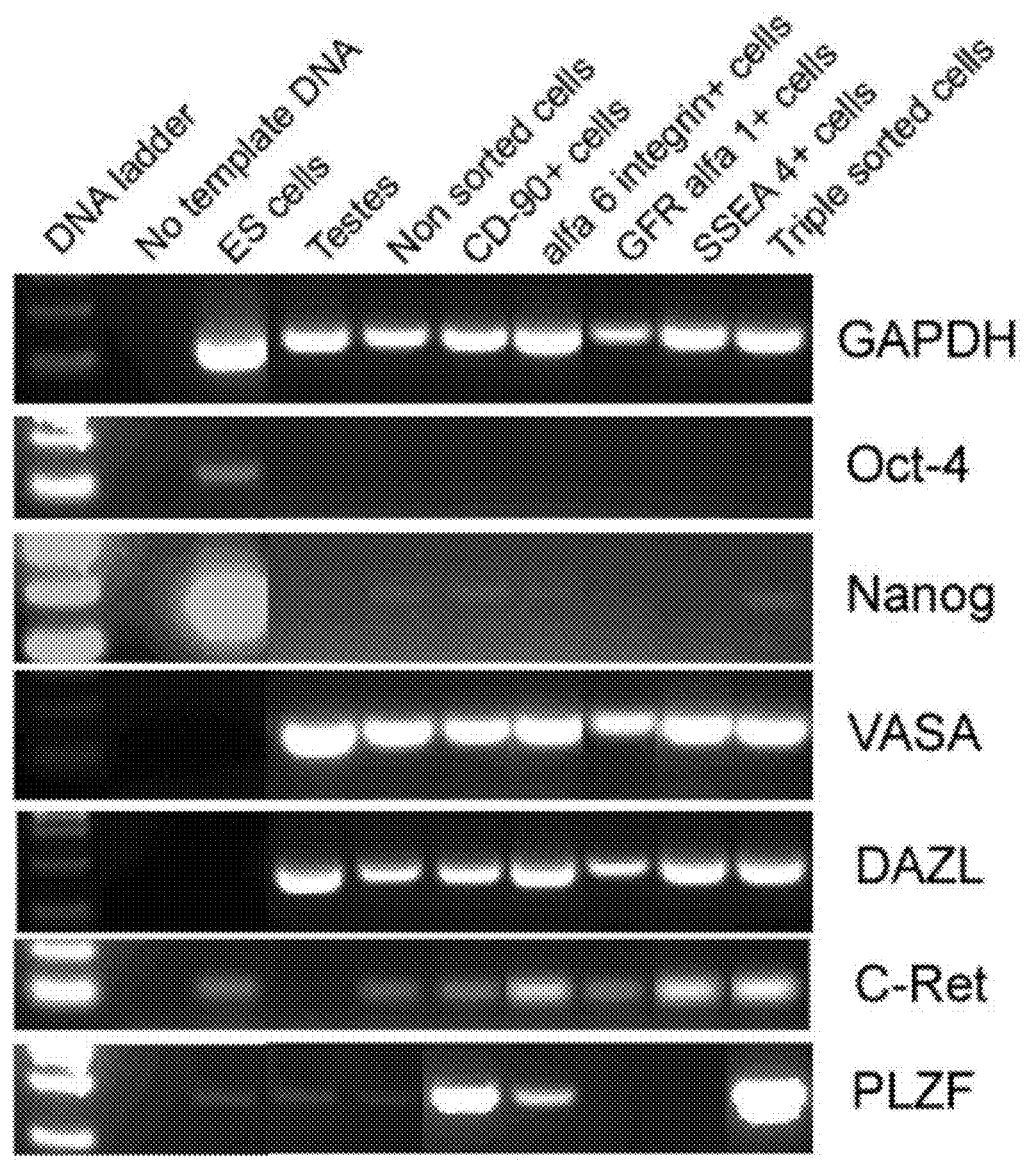
FIG. 28 depicts the gene expression profile of subpopulations of primate germline stem cells.

SSCs share some but not all phenotypic and molecular characteristics with other stem cells, in particular hematopoetic stem cells. The flow cytometry analysis, using a variety of cell surface markers, revealed that in the adult Rhesus monkey testes, there are distinct cell populations expressing α6-integrin and Thy-1 and the majority of cells in primate testes were c-Kit−. Immunohistochemical staining of primate testes also showed that all the cells along the basement membrane of seminiferous tubule were c-Kit− indicating that α6-integrin+ cells are c-Kit−. Sorting for α-6 integrin or Thy-1 alone resulted in enrichment of SSC markers as shown by immunohistochemical staining, RT-PCR and telomerase assay. Interestingly, sorting the α6-integrin+, Thy-1+ and c-Kit− cells resulted to the highest expression level of SSC marker PLZF as shown by quantitative RT-PCR (FIG. 26A) and the most elevated telomerase activity (FIG. 26B), indicating that combination of these markers enrich SSC in several folds. In addition, there were also a clear population of SSEA-4+ cells in the primate testes, which also showed a high level of telomerase activity and expressed high level of both germ and SSC markers (FIG. 28).

Immunohistochemical staining showed that SSEA-4+ cells also located at the basement membrane of seminiferous tubules and are highly co-localized with α6-integrin and GFR-α1. Flow cytometric analysis showed that there are about 5-7% of α6-integrin+, Thy-1+, c-Kit− sorted cells in adult primate testes while only 2-3% SSEA-4+ cells are present. This is also consistent with immunohistochemical data on testes sections showing that there are significantly less SSEA-4+ cells found per tubule cross section than the α6-integrin+ cells. This also indicates that SSC in primate testis have a phenotypic characteristics of α6-integrin+, Thy-1+ and c-Kit− with SSEA4+. SSEA-4 is stage specific embryonic antigen and is predominantly found in pluripotent cells like embryonic stem cells. Interestingly all the SSEA-4− cells co-expressed germ cell marker VASA, however only a fraction of these cells co-localize with GFR-α1 indicating that this marker expresses only on subpopulations of spermatogonial stem cells in monkey testis.

Morphological analysis of primate testes based on the density of the nuclear staining revealed that there are two types of undifferentiated spermatogonia in this species, $A_{dark}$ and $A_{pale}$. $A_{dark}$ spermatogonia are thought to be the reserve stem cells and not actively dividing and A$_{pale}$ spermatogonia are shown to be the active SSC in primate testes.

Using DNA dye propidium Iodide (PI) in combination with flow cytometry, it was determined that the SSEA-4+ population of germline stem cells have different DNA contents from the Thy-1+, α6-integrin+ cells. While SSEA-4+ cells had DNA profile similar to the actively dividing cells, Thy-1+, α6-integrin+ cells showed an accumulated number of cells arrested in the S phase of the cell cycle. Moreover, SSEA-4+ cells showed significantly higher proliferation activity as shown by PCNA staining than the Thy-1+, α6-integrin+ cells.

Pluripotent marker Nanog which has an essential role in maintaining ES cells in their undifferentiated stage was abundantly expressed in primate testes. Nanog expression in all germ cells and not only in SSC indicates a different role for this transcription factor in germline stem cells compared to ES cells. It has been shown that deletion of Nanog in germ cells induces apoptosis rather than differentiation indicating that Nanog is a survival factor for germ cells.

It is shown that 1 in 3000 cells in the adult mouse testes are SSC. The percentage of SSC in the adult monkey testes based on immunohistochemical staining with SSC specific markers GFRα1 and PLZF is very similar to what is described for rodents. The spermatogonial transplantation study also showed that in the adult monkey testes there are about 0.3% SSCs.

Demonstrated herein is that triple stained (CD90+, CD49f+, c-Kit−) cells and SSEA-4+ cells show molecular and phenotypic characteristics of SSCs, however only the SSEA-4+ cells repopulated recipient testes after spermatogonial transplantation. This indicates that SSEA-4+ cells might represent the actively dividing SSC and triple stained cells might resemble quiescent stem cells. Interestingly both SSEA-4 and triple stained cells expressed C-ret, the receptor of GDNF, while only triple sorted cells showed PLZF expression. Both GDNF and PLZF are known to be major regulators of spermatogonial stem cell self renewal. While GDNF regulates SSC self renewal through up regulation of BCL6b transcription factor, PLZF maintains SSC self renewal with a yet unknown mechanism. Promyelocytic leukemia zinc factor (PLZF) is shown to inhibit cell growth at the G1/S transition and transit through S-phase by suppression of cyclin A which is available in a variety of cell types. PLZF is also shown to inhibit P21 another regulator of G1/S transition. Thus a high level of PLZF results in blockage of cell cycle and quiescence. Retinoic acid receptor alfa (RAR-α) is shown to reverse the cell cycle inhibition induced by PLZF by enhancing the expression of cyclin A.

Materials and Methods

Primate Germ Cell Substantial Purification by Flow Cytometry:

Flow cytometry sorting was accomplished using an InFlux Cell Sorter. For surface characterization and sorting, cells were stained with antibody reagents specific for stem cell surface markers and spermatogonial stem cell markers in non-primate species including anti-CD90-FITC, anti-CD49f-PE, and anti-CD 117-APC. For these marker analyses, cells were stained for 30 min in complete medium on ice, washed once in cold staining buffer, resuspended in complete culture medium and kept on ice until cytofluorimetric analysis.

Primate Germ Cell Magnetic Sorting:

The population of primate germ cells was enriched by tagging with magnetic microbeads and passing the cells through a magnetic column. Freshly isolated primate testicular cells were labeled with biotinylated antibodies for SSEA-4 or for α6-integrin and Thy-1 (Ebioscience, Abcam, BD Pharrmigen, respectively). Once biotinylated, the cells were labelled with streptavidin magnetic microbeads (Miltenyi Biotec). Magnetically labeled cells were selected for by passing the cells through a column in the presence of a magnet. Magnetically labeled cells were removed from the column by removing the column from the magnet, freeing the cells to be washed off of the column. This process was successful in enriching the population of cells positive for each of the markers up to 22× the original percentage in freshly isolated cells. In addition, magnetic sorting could provide a population as high as 90% purely labeled cells. This enrichment process was used in conjugation with fluorescent flow cytometry. By magnetically sorting the cell isolation before performing fluorescent flow cytometry the amount of time needed to sort out fluorescently labeled cells was greatly reduced and the number of fluorescently labeled cells that could be sorted out was greatly increased.

Primate Germ Cell Immunohistochemical Staining:

Tissues were fixed overnight in 4% paraformaldehyde (PF; Electron Microscopy Science); transferred into 20% sucrose (Sigma) and frozen in OCT (VWR). Cryosections were prepared at 8 μm thickness and stored at −80° C. Sorted cells were fixed in 4% PF, re-suspended in 100 mM sucrose at approximately 25,000 cells/10 μl; 10 μl aliquots were transferred onto ornithine/lysine-coated glass slides; and, the slides were placed on a 37° C. hot plate until dry. Slides were stored at −80° C. until analysis.

For immunohistochemical staining, the cells in testicular sections and in FACS sorted samples were permeabilized using 0.1% Triton-X100 and blocked in either a solution containing 2% BSA and 5% sheep serum, or alternatively, in a solution containing 2% BSA, 5% goat serum and 0.1% Triton-X100. DAPI (Invitrogen) was used for nuclear visualization. Following multiple washes in 1×PBS+2% BSA, cells were preserved using Permafluor (Beckman Coulter). Distribution of surface markers in tissue sections and sorted cells was evaluated using an Olympus BX-61 microscope fitted with SlideBook™ imaging software. For localization of primate testicular cells in mouse or primate tissues, 50 different seminiferous tubules were analyzed. For each different marker staining procedure, 3 to 4 different sections were analyzed and, for FACS cell samples, at least 200 different cells were analyzed in at least three different aliquots.

Primate Germ Cell RNA Extraction, RT-PCR Analysis and QRT-PCR Analysis:

Total cellular RNA was isolated using RNeasy mini kit (Qiagen) according to the manufacturer's recommendations. The isolated RNA was then transcribed to cDNA using the Quantitect RT kit (Qiagen) and purified with the QIAquick PCR purification kit. For each RT-PCR reaction, 20 ng of cDNA template was used in a 25 μL reaction volume with HotStar Taq Plus and with the different respective primers. All target cDNAs were amplified for 30 cycles. Amplification products were identified by size on a 2% agarose gel. For QRT-PCR, 5 ng of cDNA template was used in a 25 μL reaction volume with Quantitect Sybr Green PCR master mix (Qiagen) and the samples were amplified using a BioRad iCycler. Each sample was assayed in triplicate and normalized to a GAPDH control.

Primate Germ Cell Telomerase Assay:

The SYBR Green real time quantitative telomeric repeat amplification protocol (RQ-TRAP) was employed. Tissue or cells pellets were washed once in PBS, resuspended and homogenized in 1× Chaps lysis buffer containing RNaseOut Inhibitor (Invitrogen), at a final concentration of 1000 cells/

µL and 400 units/mL of the RNaseOut Inhibitor. After 25 min of incubation on ice, the cell lysates were centrifuged at 4° C. in a microfuge at 16,000 rpm for 10 min. The supernatant was transferred to a fresh microcentrifuge tube and the protein concentrations determined by measuring absorbance at 280 nm using an ND-1000 spectrophotometer (Nanodrop). Telomerase reaction volumes were 25 µL in a solution containing 500 ng protein lysate, Quantitect SYBR Green PCR mix, 1 µg TS primer, 0.5 µg ACX primer and nuclease-free distilled water. Each sample was tested in triplicate along with a no template control (lysis buffer), a positive control (ESC cells), and a standard curve prepared from aliquots of human ESC lysate that contained 1000 ng, 200 ng, 40 ng, 8 ng or 1.6 ng of protein. Using the iCycler iQ5 (Bio-Rad), the reactions were incubated for 20 min at 25° C., for 15 min at 95° C., and amplified in 40 PCR cycles under the following cycle conditions: 30 sec at 95° C. and 90 sec at 60° C. The threshold cycle values (Ct) were determined from semi-log amplification plots (log increase in fluorescence versus cycle number) and compared with standard curve. The software default setting for the threshold was 10 times the mean of the standard deviation of the fluorescence reading of each well over the first 10 cycles, excluding cycle 1. Telomerase activities for different primate testicular cell samples were read from the standard curve and/or expressed as a percentage of the values recorded with human ESC lysate standards.

TABLE 2

MEM-X Primate Media Composition

| Component | Final Concentration |
|---|---|
| DMEM/F12 | N/A |
| Testosterone | 50 ng/mL |
| Estradiol | 50 ng/mL |
| Bovine Serum Albumin | 5 µg/mL |
| Sodium Pyruvate | 30 µg/mL |
| Hydrocortisone | 0.05 mM |
| D/L Lactic Acid | 1 µl/mL |
| Glutamine | 1X |
| MEM Vitamin | 2X |
| MEM NEAA | 1X |
| Insulin-Transferrin-Selenine | 1X |
| Penicillin/Streptomycin | 1X |
| Epidermal Growth Factor | 20 ng/mL |
| basic Fibroblast Growth Factor | 10 ng/mL |
| human Leukemia Inhibitory Factor | 10 ng/mL |
| Glial Derived Neurotrophic Factor | 40 ng/mL |

Example 3

Culture Expansion of Primate Germline Stem Cells

Germline stem cells (Example 2) after isolation were transferred to MEF plates and cultured in different serum free media including Mouse Serum Free Medium (MSFM), Rat Serum Free Medium (RSFM) or MEM-X® media. The morphological changes of the cells and the number of germ cell colonies per well was counted during culture. Half of the medium was changed every other day.

Ten days after culture, flat colonies appeared in all media types (FIG. 29A). Colonies in MEM-X maintained their morphology better than other two culture media. The number of colonies found in non-sorted population was lower than sorted cells. Among the cell surface markers tested, SSEA-4 and triple stained cells resulted in colony formation. Depletion of SSEA-4+ cells from triple sorted cells resulted to very few colonies; however depletion of the triple sort phenotype from SSEA-4+ cells did not change colony formation ability. Cells positive for both SSEA-4 and triple sort formed highest number of colonies in culture and cells depleted from SSEA-4 and triple sort did not form any colony. The colonies were then stained for SSEA-4 (FIG. 29B-C), GFR-α (FIG. 29D) and α6-integrin Example 4

Isolation of Murine Female Germline Stem Cells

Mouse ovaries from 40-60 transgenic OG2 post-natal pups, aged 2-5 days, were dissected under a micro dissection microscope and used for cell isolation. Ovaries were first collected in a culture dish containing cold D-PBS supplemented with 4 mM EDTA. Using a 5 ml pipette, ovaries were then transferred with to a 50 ml conical tube. After centrifugation and washing, the D-PBS wash solution was removed and the ovaries were resuspended in collagenase (1 mg/ml) and DNase-I (20 unit/ml); and, placed in a 37° C. water bath. Every 10 min, the digesting ovarian tissues were physically disrupted by pipette and at the end of the incubation (30 min), 5 ml of FBS was added to neutralize the enzymes. The resultant cell suspension was passed through a 40 µm strainer to remove tissue debris and the isolated cells were collected by centrifugation at 400×G for 10 min. The supernatant enzyme-FBS solution was removed and cells were resuspended in culture medium and kept on ice until use.

Figure 11A:
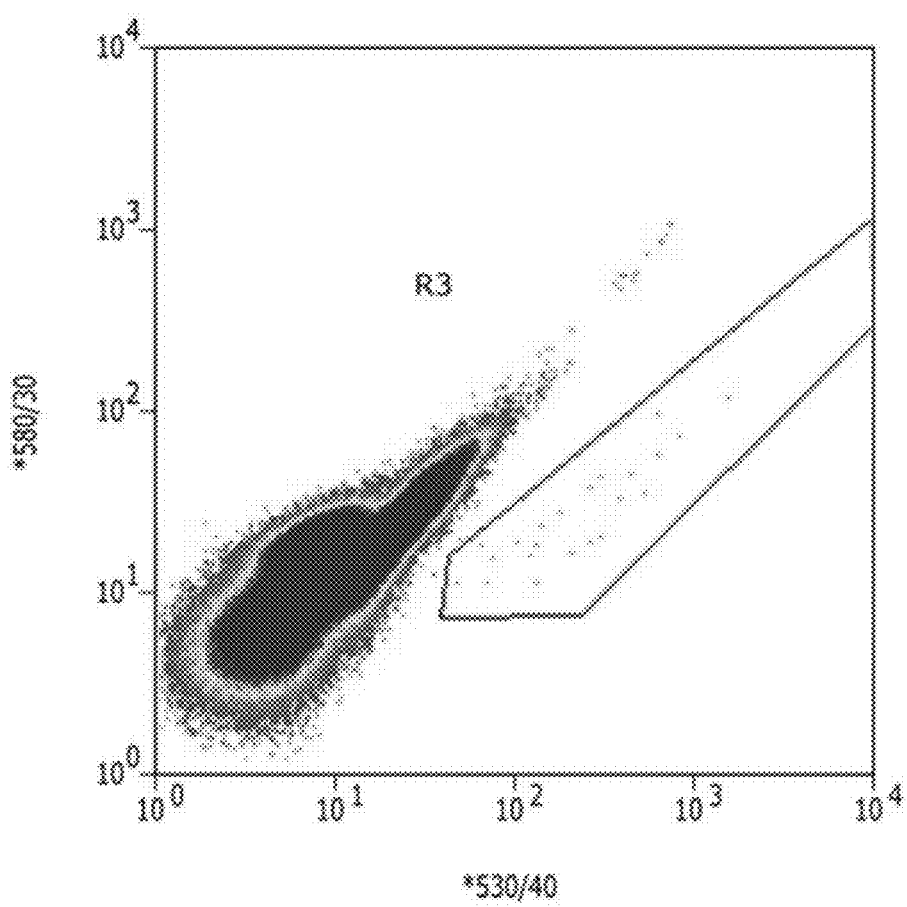
FIG. 11A shows adult ovarian germline stem cells as depicted graphically with the fluorescence intensity of GFP.
Figure 11B:
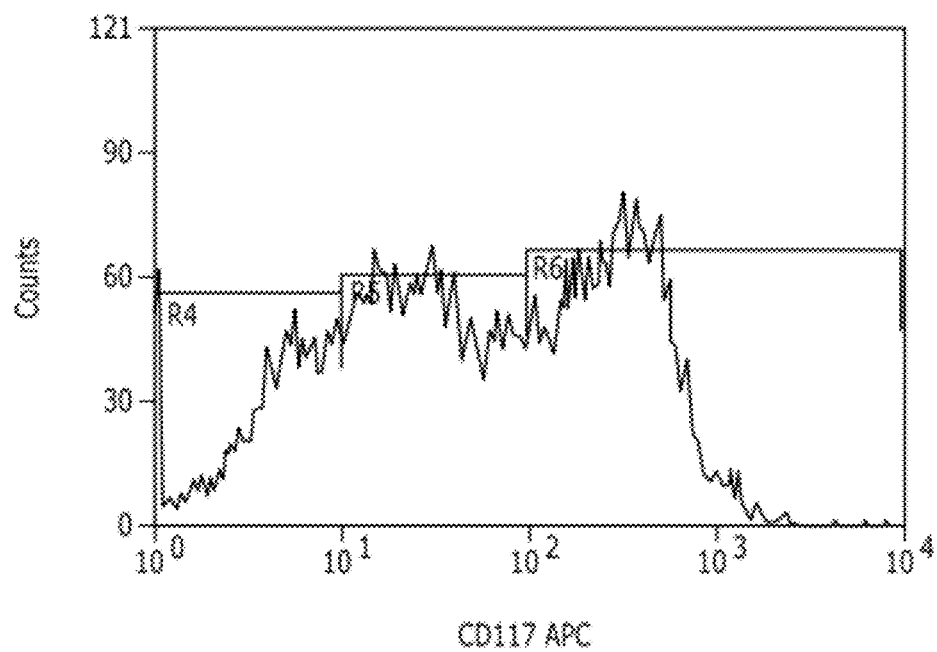
FIG. 11B shows neonatal ovarian germline stem cells as depicted graphically with the fluorescence intensity of GFP (levels of c-Kit on GFP+ cells).
Figure 11C:
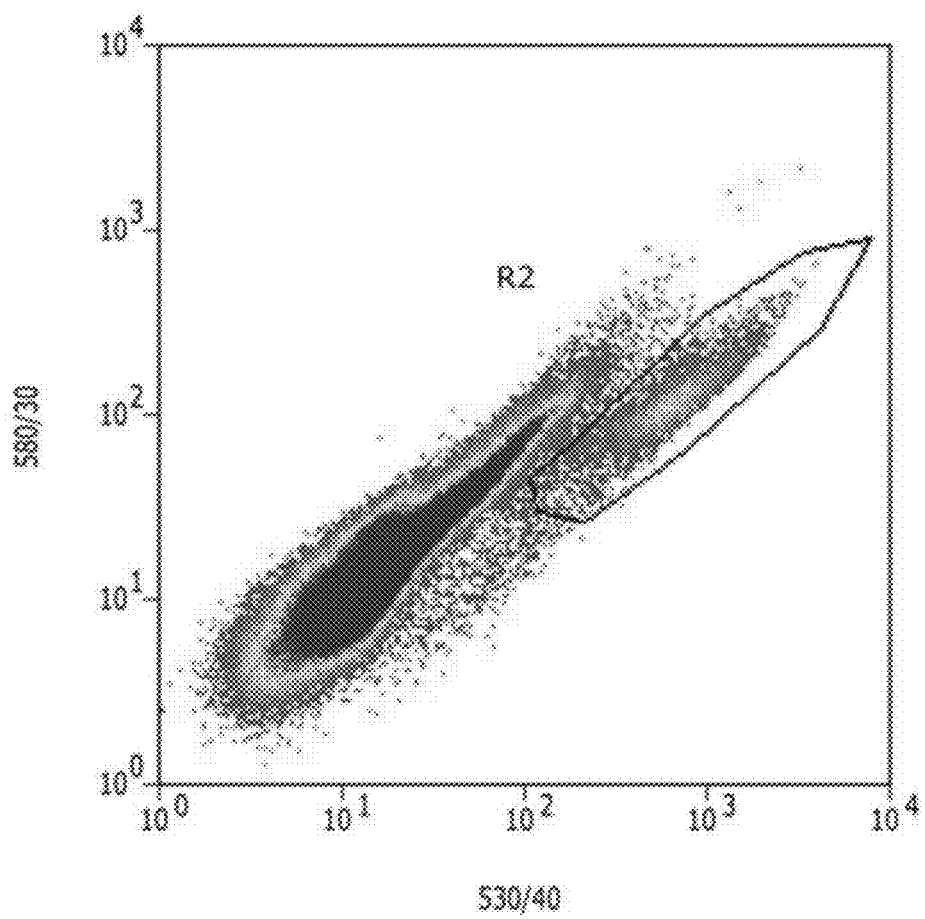
FIG. 11C depicts graphically the fluorescence intensity of neonatal GFP+ cells expressing c-Kit, also known as CD117.

Ovarian germ-line stem cells were substantially purified by collecting GFP-positive cells by flow cytometry identifying green fluorescent intensity (FIG. 11A), gating three channels for c-Kit (R2, R3 and R4) (FIG. 11B); and then sorting R3 for c-Kit intensity (FIG. 11C).

Figure 12A:
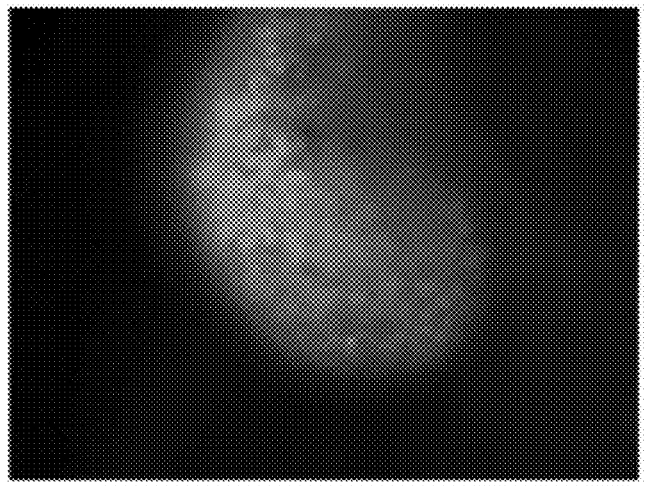
FIGS. 12A and 12B show total fluorescence and FIG. 12C shows a computer enhanced cross sectional image with removal of autofluorescence.
Figure 12B:
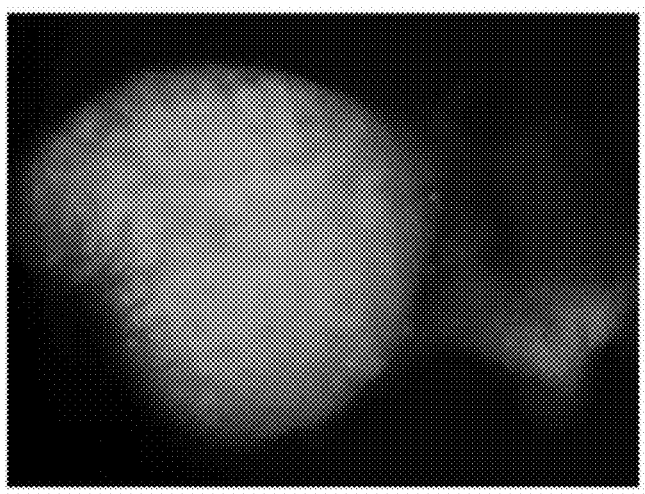
Figure 12C:
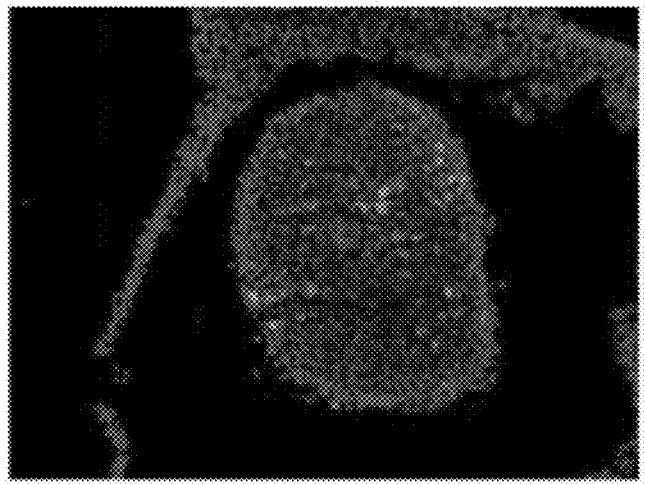
Figure 13:
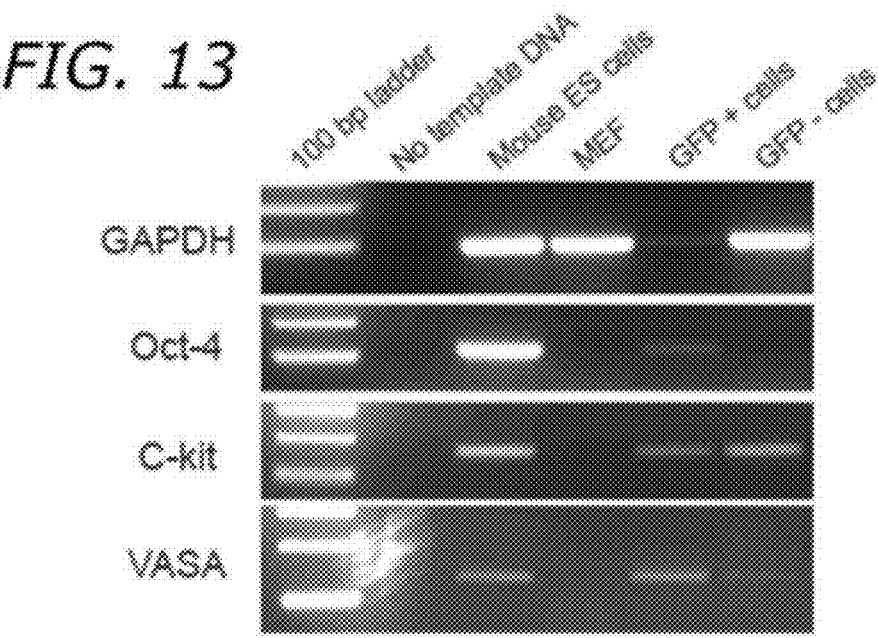
FIG. 13 depicts the results of RT-PCR analysis of mRNA isolated from mouse embryonic stem cells (lane 3), mouse embryonic fibroblasts (MEF, lane 4), GFP+ germline stem cells (lane 5) and GFP– cells (lane 6) isolated from an OG2 transgenic mouse.

Using flow cytometry, GFP/Oct-4+ cells were detected in neonatal (FIG. 11A) and adult (FIG. 11B) mice indicating the presence of germline stem cells in postnatal ovary. The percentage of germline stem cells in the mouse ovary significantly diminished with age. While 1-2% GFP+ cells were found in the ovaries of the neonatal mice, only 0.05% were present in the adult ovary. Among the Oct-4+ cells, 60% were negative or expressed low level of c-Kit and 40% showed high level of c-Kit expression (FIG. 11C), indicating the presence of two populations among germline stem cells. Immunohistochemical analysis revealed that GFP-Oct-4+ cells are present throughout the ovarian epithelium (FIGS. 12A-12C). RT-PCR analysis showed that GFP+ cells isolated from neonatal mouse ovary expressed both pluripotent marker Oct-4 and germ cell markers VASA and c-Kit confirming the presence of germline stem cells in this population, while the GFP– cells showed only the expression of germ cell markers (FIG. 13).

In contrast to expectations, freshly isolated adult or neonatal ovarian cells showed very low telomerase activity. However, RT-PCR analysis confirmed that GFP+ cells at the onset of culture, like ESC, express Oct-4 (FIG. 13). GFP+ cells expressed Oct-4 (FIG. 13, lane 5) while GFP– cells did not (FIG. 13, lane 6). GFP+ cells expressed higher levels of VASA (FIG. 13, lane 5) than GFP– cells. GFP– cells expressed higher levels of c-Kit than GFP+ cells.

The marker c-Kit has been associated with male germline stem cells in certain prior scientific reports. Among the Oct-4+ cells, 60% were negative or expressed low level of c-Kit and 40% showed high level of c-Kit expression. GFP+ cells isolated from neonatal mouse ovary expressed both pluripotent marker Oct-4 and germ cell markers VASA and c-Kit. The combined results confirm the presence of germ-line stem cells in the GFP+ cell population isolated from the ovaries of OG2 mice.

Figure 14A:
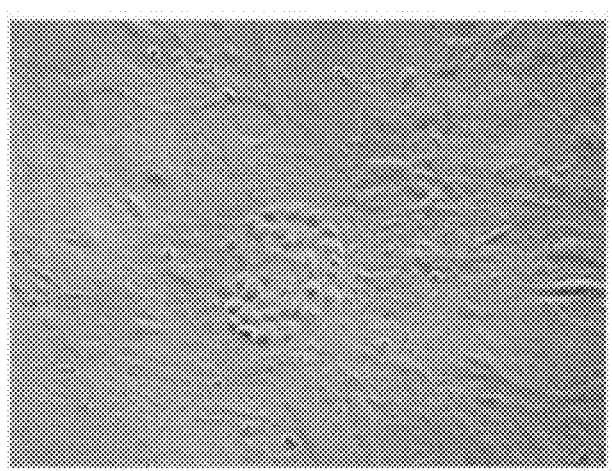
FIG. 14A shows colonies after 4 days in culture.
Figure 14B:
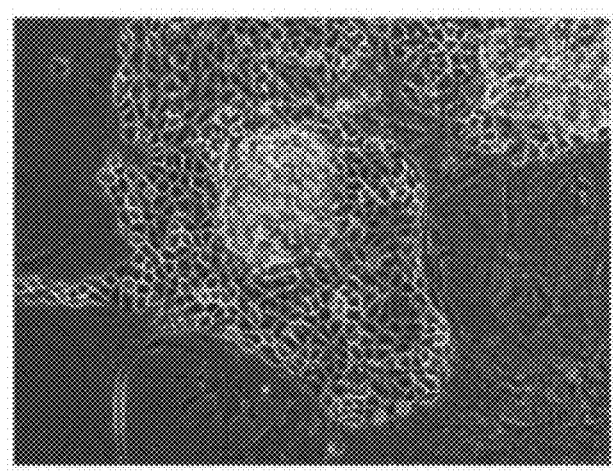
FIG. 14B shows a first type of representative colony morphology.
Figure 14C:
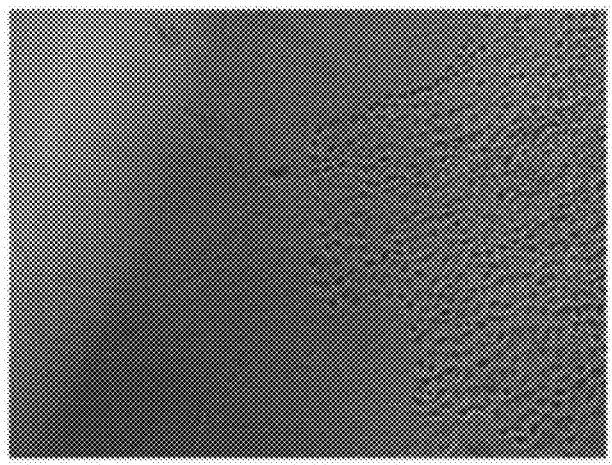
FIG. 14C shows a second type of representative colony morphology.
Figure 14D:
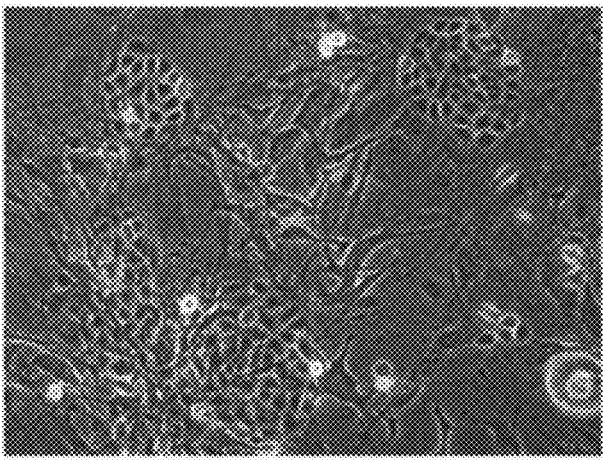
FIG. 14D shows colony morphology after passage with collagenase.
Figure 14E:
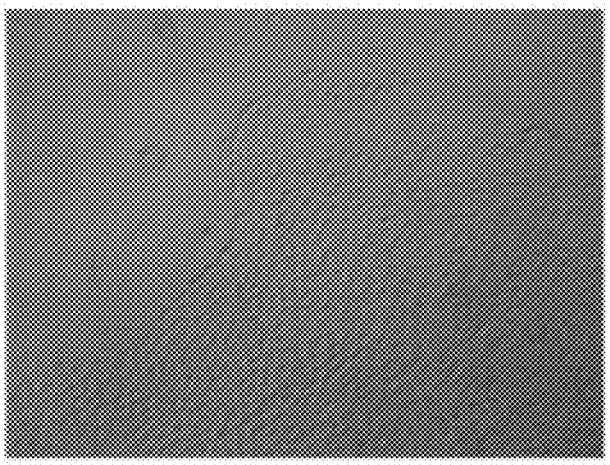
FIG. 14E shows a third type of representative colony morphology after collagenase passage having a clearly defined border.
Figure 14F:
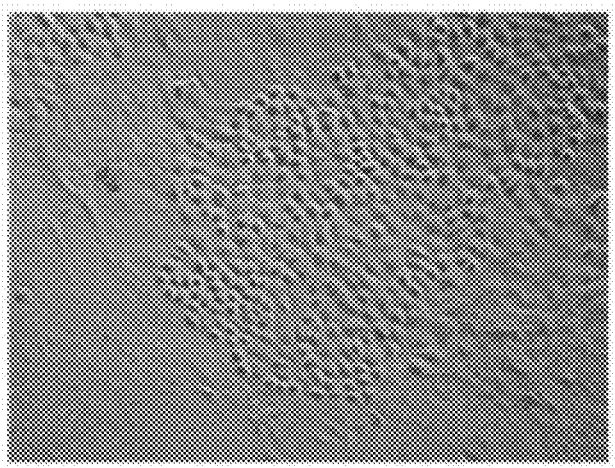
FIG. 14F shows a fourth type of representative colony morphology after collagenase passage having a poorly defined border.
Figure 14G:
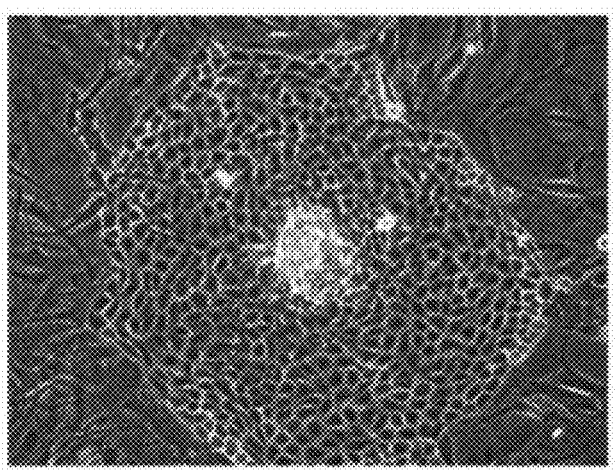
FIG. 14G shows colony morphology after passage #1.
Figure 14H:
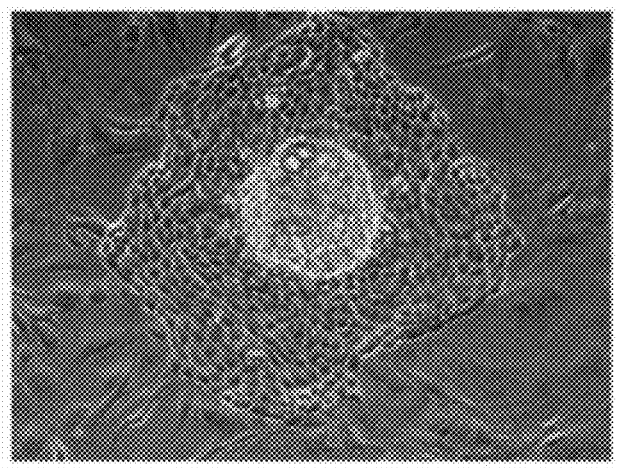
FIG. 14H shows colony morphology after passage #2.
Figure 14I:
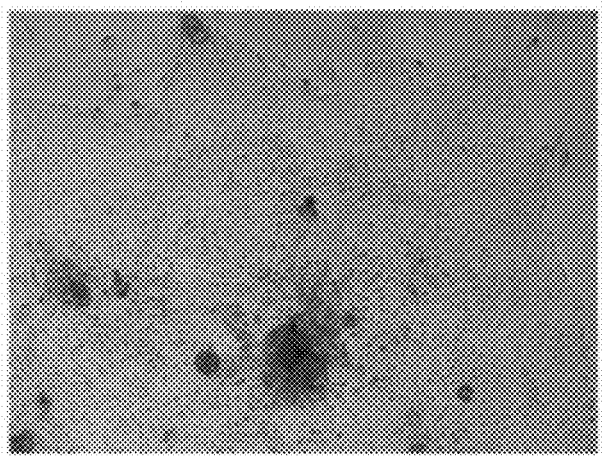
FIG. 14I shows colony morphology after passage #3.
Figure 14J:
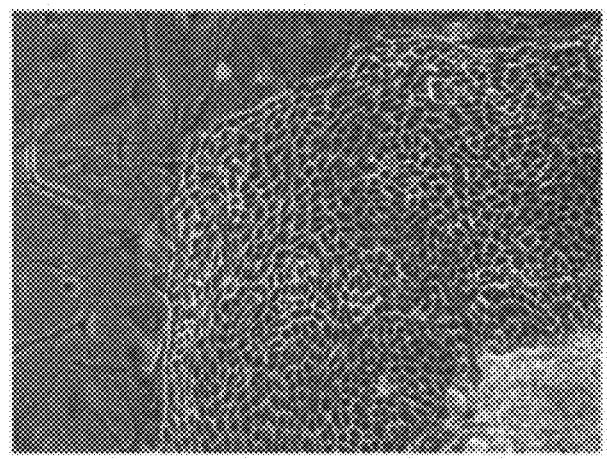
FIGS. 14J and 14K show two different magnifications of ovarian germline stem cell colonies after passage #4.
Figure 14K:
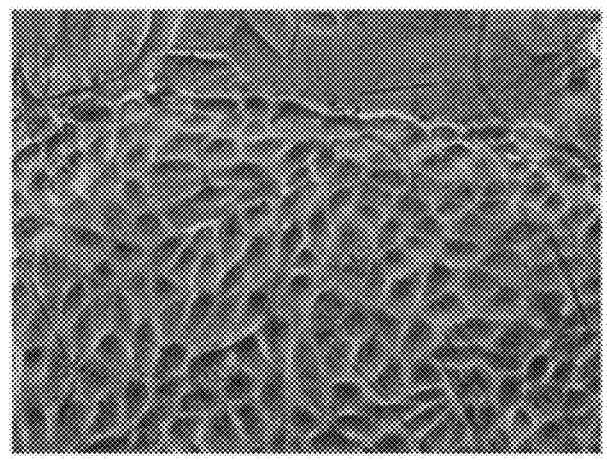

GFP+ cells cultured on feeder layers of MEF formed round and flat colonies some of which had clearly defined boundaries (FIGS. 14A-14C and 14E), but others did not (FIG. 14F). Representative of the clear-border and non-clear border colonies were picked (FIG. 14B) and passaged on MEFs using collagenase (FIG. 14D). After passage, cells assembled into distinctive colonies recognizable by a tight oval central grouping of small round cells surrounded by flat tightly packed cells having a more epithelioid shape (FIG. 14G-14I). This colony appearance was continued beyond passage 4 (FIG. 14J-14K).

Figure 15A:
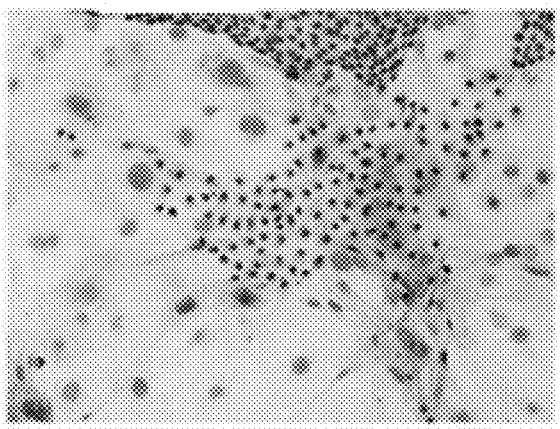
FIG. 15 depicts immunocytochemical staining of isolated and substantially purified ovarian germline stem cells, stained to reveal expression of pluripotent stem cell marker Oct-4 (FIG. 15A); pluripotent stem cell marker Nanog (FIG. 15B); germ cell marker VASA (FIG. 15C); and pluripotent stem cell marker alkaline phosphatase (FIG. 15D).
Figure 15B:
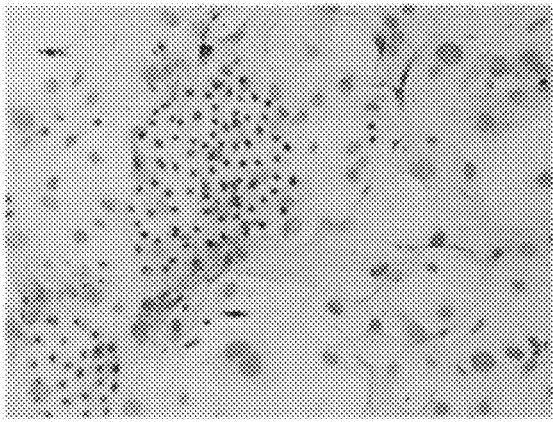
Figure 15C:
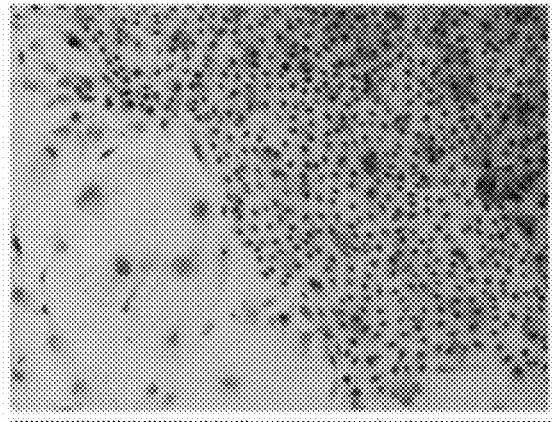
Figure 15D:
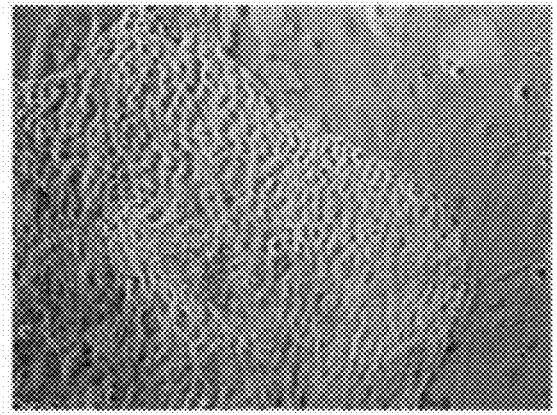

As expected, colonies of GFP+ ovarian cells stained positive for Oct-4 (FIG. 15A). Supportive of their identity as germline cells, the cells in these colonies also stained positive for pluripotent transcription factor Nanog (FIG. 15B). In addition, these cells also expressed germline specific marker VASA (FIG. 15C) and stem cell marker alkaline phosphatase (FIG. 15D). The combined results confirm the isolation, identification, characterization and passage in tissue culture of female germline stem cells.

Figure 16A:
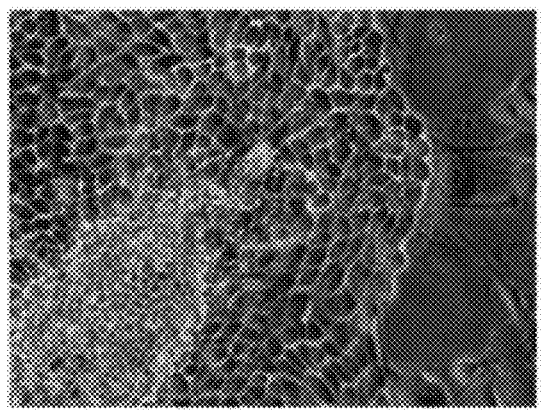
FIG. 16A shows GFP+ cells resembling primary oocytes growing at the center of the female germ cell colony.
Figure 16B:
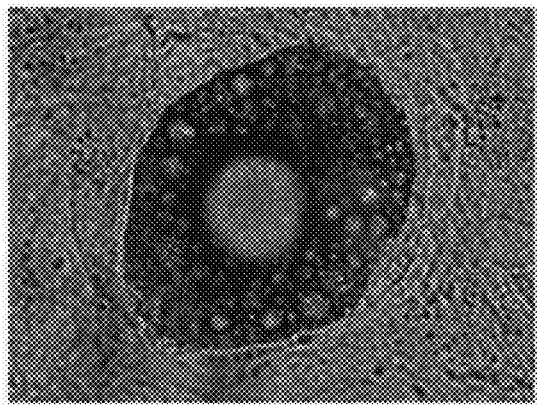
FIG. 16B shows images of follicle-like structures.
Figure 16C:
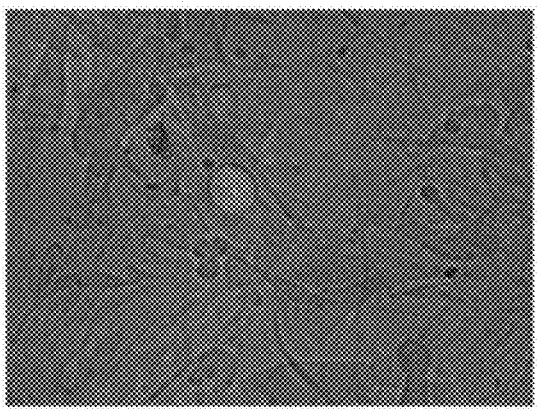
FIG. 16C shows GFP+ cells resembling primary oocytes growing in the vicinity of the female germ cell colony.
Figure 16D:
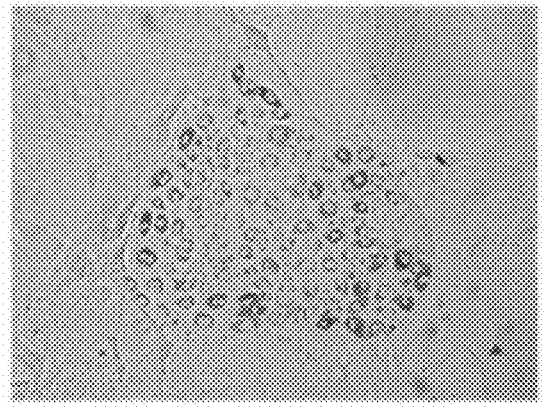
FIG. 16D depicts a pigmented colony.

The GFP+ colonies tolerated enzymatic digestion using collagenase and generated new colonies. However, they did not tolerate trypsinization and the majority of the colonies differentiated after trypsin treatment. GFP− cells showed only the expression of germ cell markers and not stem cell markers. After several passages (for example, passage 15) these differentiated colonies retained their morphology, but most cells no longer expressed GFP, suggesting down-regulation of the Oct-4 promoter and possible differentiation. Only a few cells in each colony, mainly large cells in the center of the colony, showed GFP expression. With time, these GFP+ cells appeared to form very large, up to 40 mm, oval cells that were resident in structures having morphologic similarity to ovarian follicles (FIG. 16A, 16B). Eventually, the oval GFP+ cells separated from the colony, i.e., taking on the appearance of primary oocytes (FIG. 16C). Overall, the results support the notion that isolated and substantially purified ovarian germline stem cells differentiate and mature ex host, giving rise to primary oocytes.

Figure 17A:
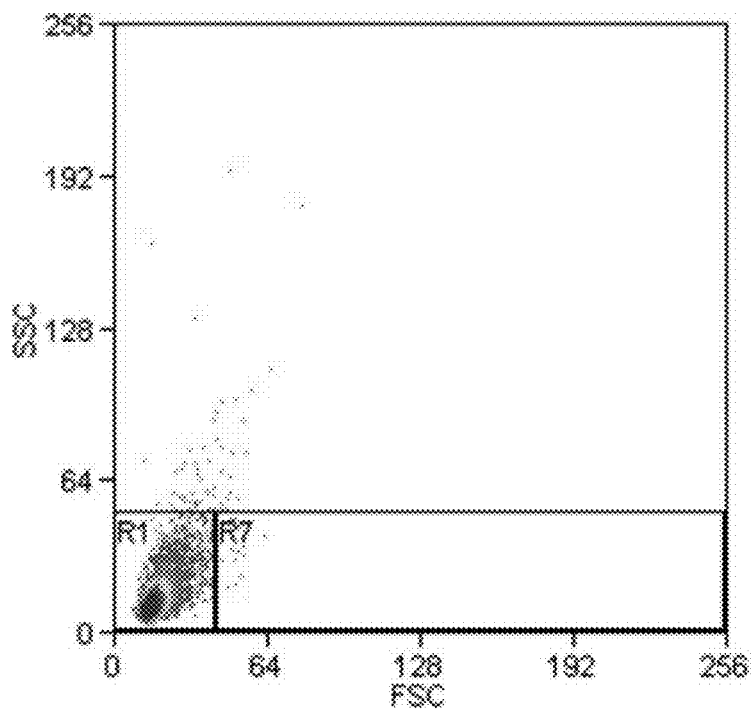
FIG. 17A depicting MEF control cells (<15 µm)
Figure 17B:
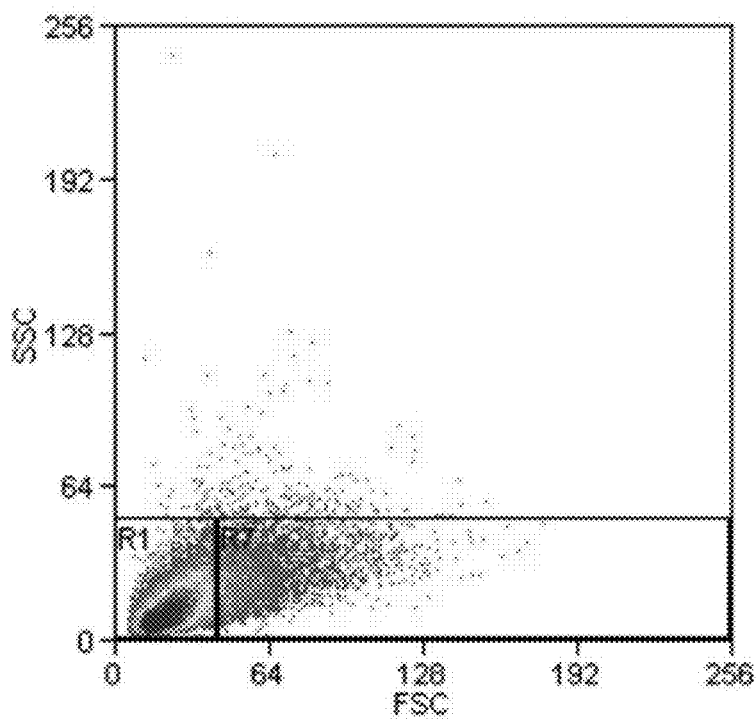
FIG. 17B depicting the oocyte-like cells of FIG. 16.

The presence and characteristics of these large oocyte-like cells were confirmed by substantially isolating and purifying them from the cultures of FIG. 16 as follows: using standard flow cytometry sizing beads, a gate was generated (R1) showing all the events 15 micrometer ($\mu$) and smaller; MEF cells were homogenous population all accumulated in R1 (FIG. 17A); significant numbers of large cells (>15$\mu$) in the germ cell cultures of FIG. 16 grown on MEF. Some of these cells were about 60-70 micrometer in diameter.

Materials and Methods

Culture of Ovarian Germline Stem Cells:

GFP+ cells were cultured on MEF feeders in PM-1™ medium in a concentration of 5000-10000 per well of a 4-well plate. Culture was maintained at 37° C. and half of the medium was changed every other day. Every two weeks cells were transferred either mechanically or enzymatically (collagenase) to a new MEF plate.

Characterization of Ovarian Germ-Line Stem Cells:

Freshly isolated GFP-positive cells were used for telomerase assay and gene expression profiling. For ovarian histology, ovaries were fixed in 4% paraformaldehyde (PFA) in 1M sucrose overnight at 4° C. and mounted in cryostat freezing medium. Five micron sections were prepared and localization of the GFP+ cells was determined using fluorescent microscopy. Localization of germline stem cells in the ovary was confirmed by Oct-4 and VASA double labeling. For immunocytochemistry (ICC), cultured ovarian germ-line stem cells were fixed in 2% PFA for 30 min at room temperature, washed in PBS and kept at 4° C. To characterize cultured ovarian germ-line stem cells, VASA, Oct-4, Nanog and alkaline phosphatase staining was performed using bright field ICC, as described further below.

RT-PCR and QRT-PCR Analysis:

Total cellular RNA was isolated using an RNeasy mini kit (Qiagen) according to the manufacturer's recommendations. The isolated RNA was then transcribed to cDNA using a Quantitect RT kit. Transcribed cDNA was purified using QIAquick PCR purification kit. For each RT-PCR reaction, 20 ng of cDNA template was used in a 25 $\mu$L reaction volume with HotStar Taq Plus (Qiagen) and appropriate primers. All targets were amplified for 30 cycles. Amplification products were identified by size on a 2% agarose gel. For QRT-PCR, 5 ng of cDNA template was used in a 25 $\mu$L reaction volume with Quantitect Sybr Green PCR master mix and the reaction mixtures were amplified using a BioRad iCycler. Each sample was assayed in triplicate and normalized to a GAPDH control.

Example 5

Isolation of Human Male Germline Stem Cells

Human testes collected as testicular biopsies from patients with non-obstructive azospermia or remnant of testes tissue collected after orchiectomy were used for this study. All the tissues were donated with the informed consent of the patients. Tissues were transferred in PBS-antibiotics at 4° C. within 24 hr of collection. The procedure of processing human testicular tissue is similar to that for primate as disclosed in Example 2.

Before cell isolation, a tissue sample was taken for ICC, and two small pieces of testes were taken for RNA and DNA extractions. Following cell isolation and determination of viability and cell number, samples were taken for RNA and DNA analysis. Methods for ICC, RNA and DNA extractions are similar to the primate as disclosed in Example 2. In addition, cells were labeled for expression of cell surface markers previously developed for separation of primate germline stem cells were used by magnetic cell sorting and flow cytometry. Antibodies and methods used for flow cytometry is similar to that used for separation of primate germline stem cells as disclosed in Example 2.

The population of germ cells was also enriched by tagging with magnetic microbeads and passing the cells through a magnetic column. Freshly isolated testicular cells were labeled with biotinylated antibodies for SSEA-4 or for $\alpha$6-integrin and Thy-1. Once biotinylated, the cells were labeled with streptavidin magnetic microbeads. Magnetically-labeled cells were selected for by passing the cells through a column in the presence of a magnet.

Magnetically-labeled cells were removed from the column by removing the column from the magnet and freeing the cells to be washed off of the column. This process was successful in enriching the population of cells positive for each of the markers up to 22× the original percentage in freshly isolated cells. In addition, magnetic sorting could provide a population as high as 90% purely labeled cells. This enrichment process was used in conjugation with fluorescent flow cytometry. By magnetically sorting the cells before performing fluorescent flow cytometry, the amount of time needed to sort fluorescently-labeled cells was greatly reduced and the number of fluorescently-labeled cells that could be sorted was greatly increased.

Sorted cells were then used for RT-PCR and DNA analysis. Also, some samples cells were subjected to a spermatogonial transplantation assay using immunodefficient mice as recipients. The techniques for spermatogonial stem cell transplantation are similar to the mouse and primate as disclosed in Examples 1 and 2.

Immunohistochemical staining on frozen sections prepared from both testicular biopsies and remnant testes tissue revealed that there are many α6-integrin+ cells at the basement membrane of tubular cross sections. Also SSEA-4+ cells and GFR α1+ cells were found at the basement membrane of the seminiferous tubules.

Figure 30A:
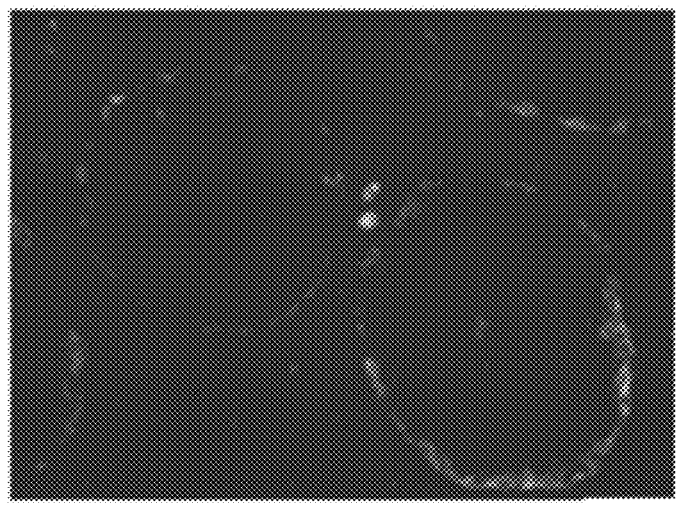
FIG. 30 depicts human whole testicular tissue (THT) stained with SSEA-4 (FIG. 30A) and VASA (FIG. 30B).
Figure 30B:
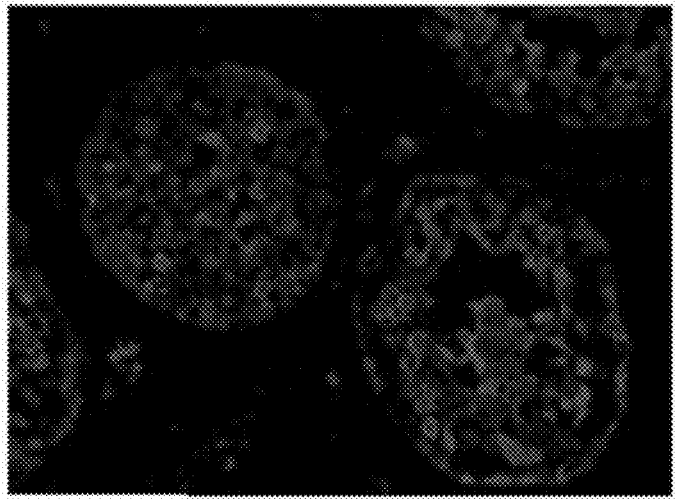
Figure 31A:
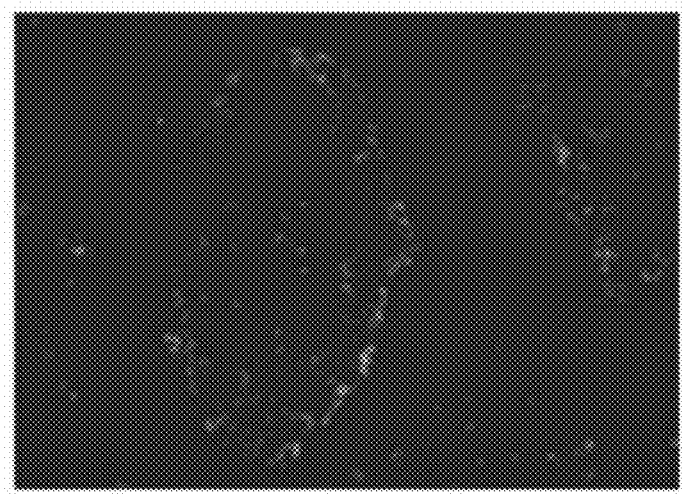
FIG. 31 depicts THT stained with GFR-α (FIG. 31A) and VASA (FIG. 31B).
Figure 31B:
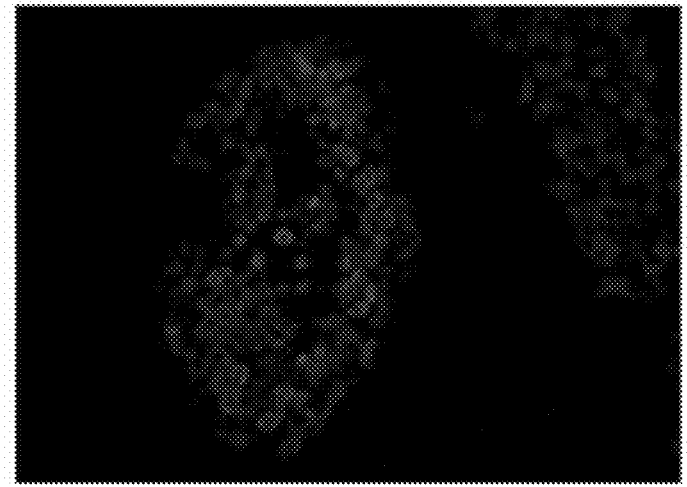
Figure 32A:
FIG. 32 depicts THT stained for VASA (FIG. 32A) and Nanog (FIG. 32B).
Figure 32B:
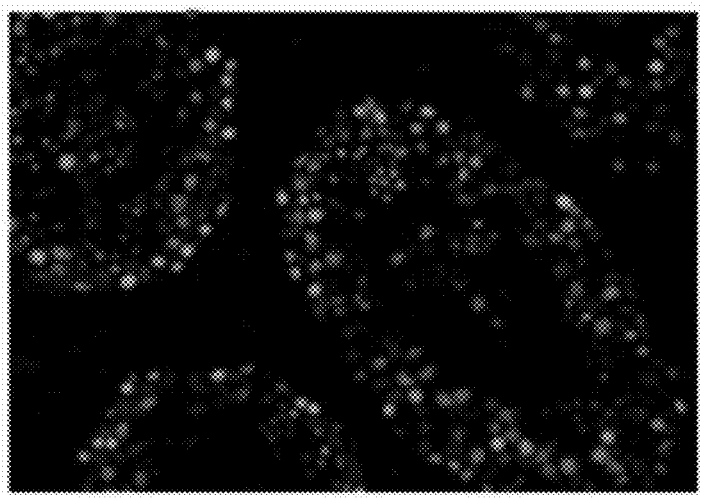
Figure 33A:
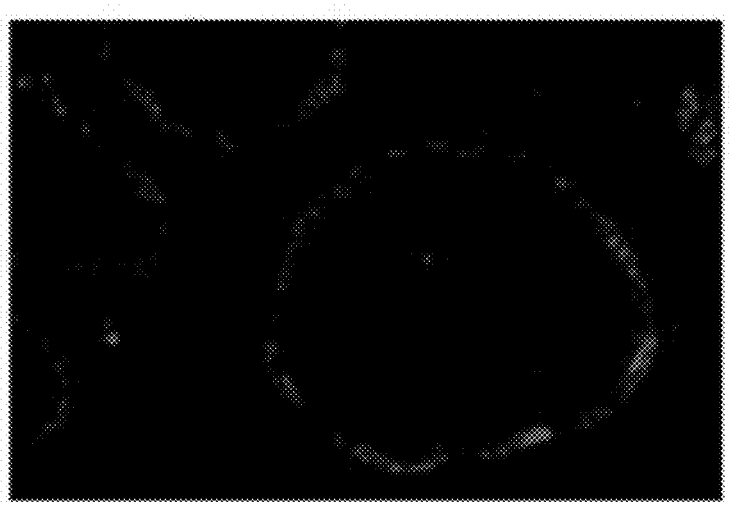
FIG. 33 depicts THT stained for SSEA-4 (FIG. 33A) and α6-integrin (FIG. 33B).
Figure 33B:
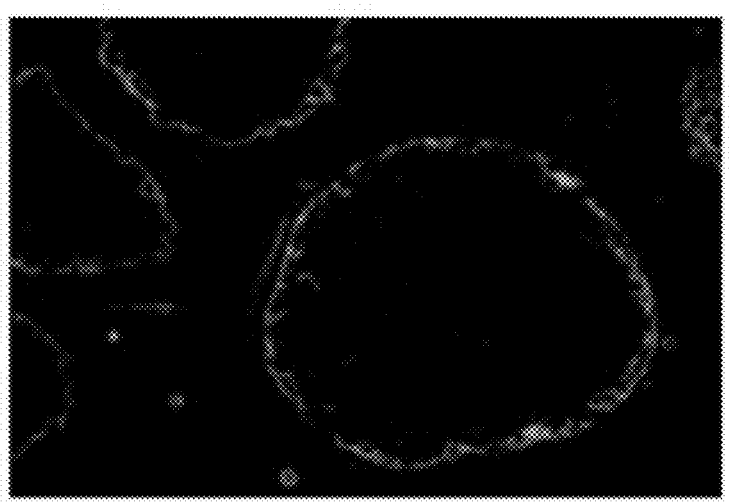
Figure 34A:
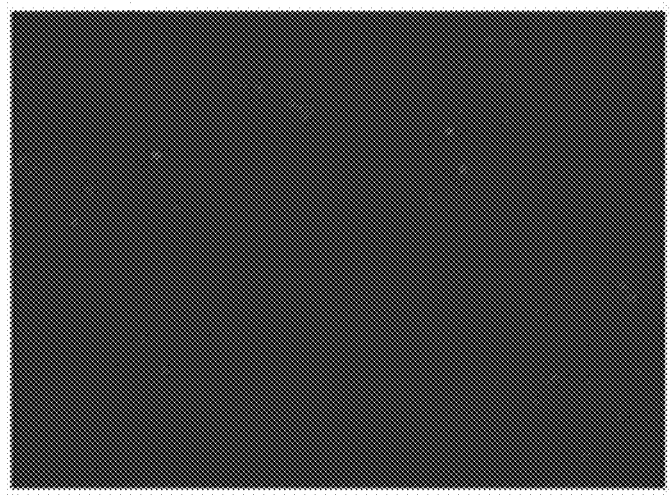
FIG. 34 depicts negative controls for FIGS. 30-33 consisting of human testis sections stained only with secondary antibody.
Figure 34B:
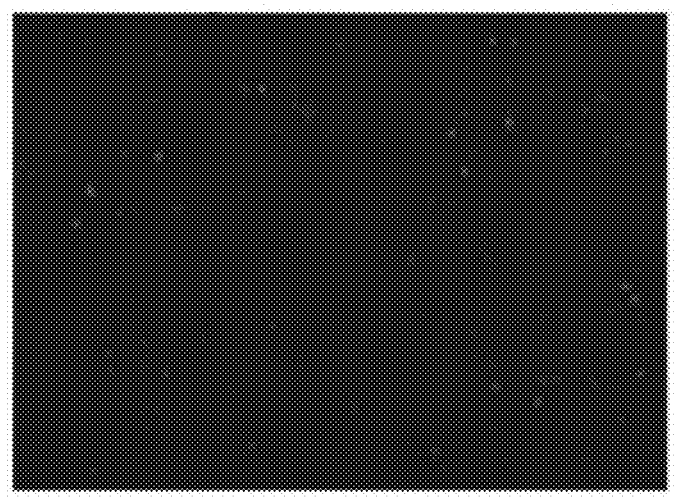
Figure 35A:
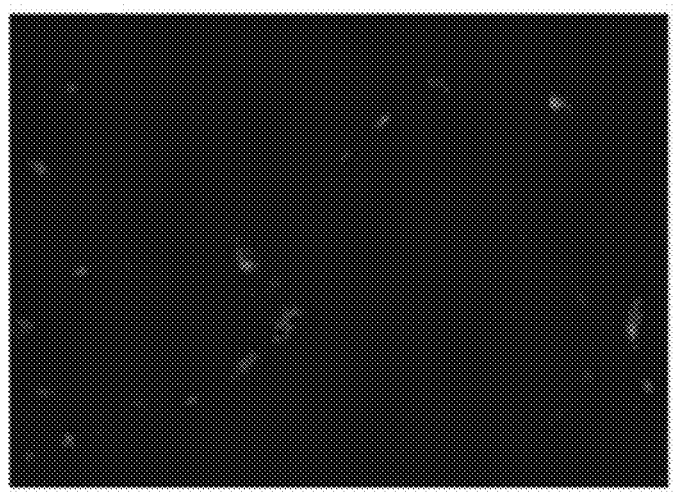
FIG. 35 depicts THT SSEA-4+ magnetic bead sorted cells transplanted into busulfan-treated recipient mouse testes and after one month stained for SSEA-4 (FIG. 35A) and human nuclear protein (FIG. 35B).
FIGS. 35C and D depicts the negative control.
Figure 35B:
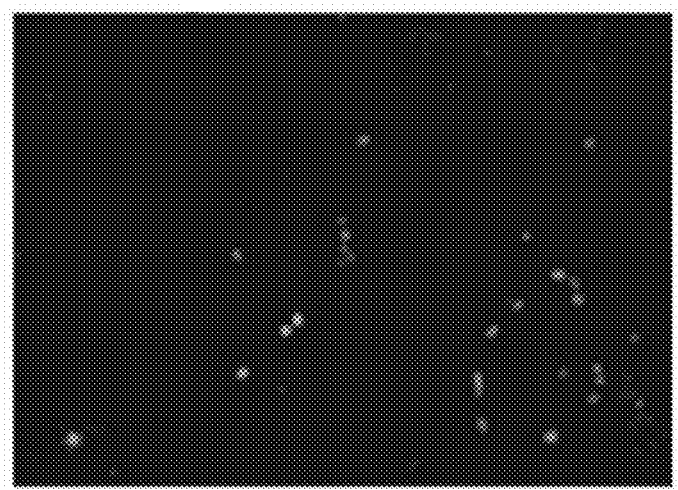
Figure 36A:
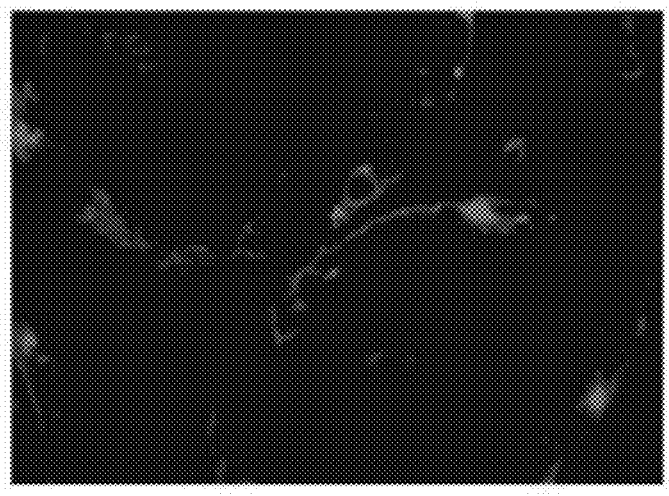
FIG. 36 depicts THT SSEA-4+ magnetic bead sorted cells transplanted into busulfan treated recipient mouse testes and after one month stained for α6-integrin (FIG. 36A) and human nuclear protein (FIG. 36B).
Figure 36B:
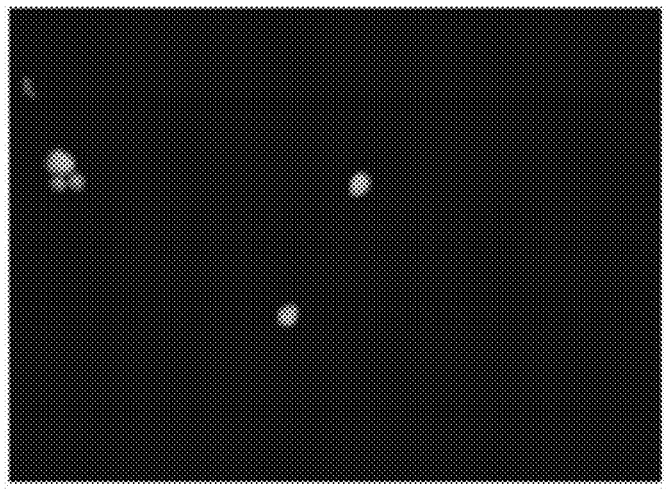
Figure 37A:
FIG. 37 depicts THT SSEA-4+ magnetic bead sorted cells transplanted into busulfan treated recipient mouse testes and after one month stained for SSEA-4 (FIG. 37A) and α6-integrin (FIG. 37B).
Figure 37B:
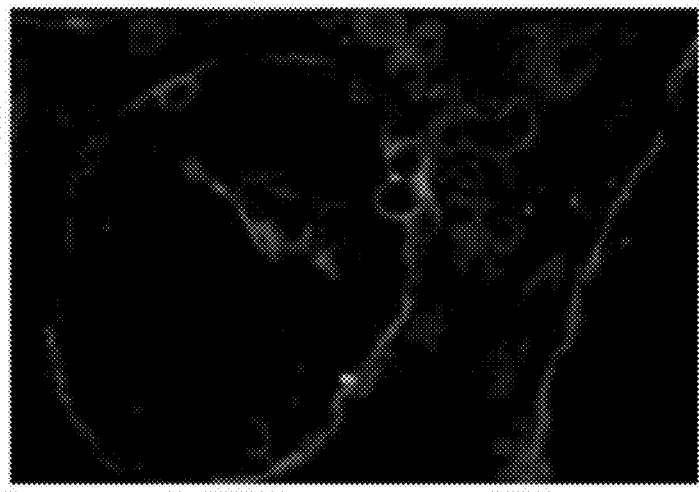
Figure 38A:
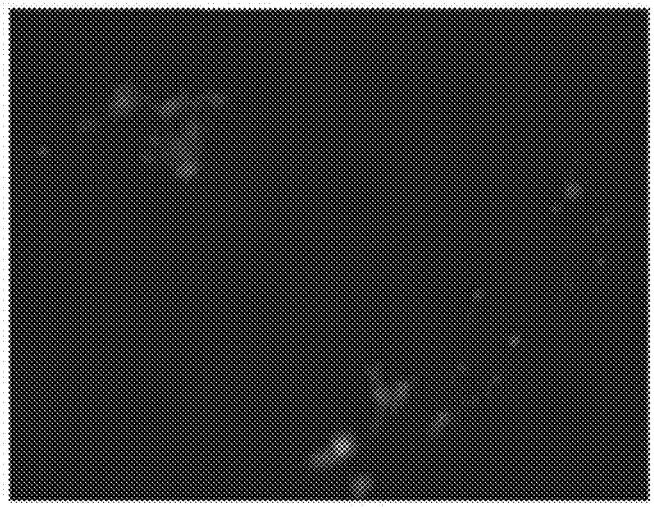
FIG. 38 depicts the negative control for FIGS. 36 and 37 consisting of human testis sections stained only with second antibody.
Figure 38B:
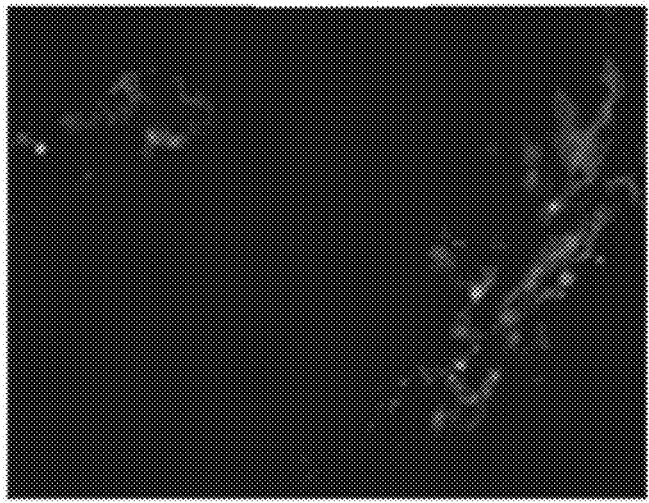

The following ICC was performed: whole human testes tissue (THT) stained for SSEA-4 and VASA (FIG. 30); THT stained for GFR-α and VASA (FIG. 31); THT stained for VASA and Nanog (FIG. 32); bHT-1 (biopsy human testes tissue) stained for SSEA-4 and α6-integrin (FIG. 33). Negative controls consisted of human testis sections stained only with secondary antibody (FIG. 34). Human THT SSEA-4+ magnetic bead sorted cells were transplanted into busulfan-treated recipient mouse testes and after one month were sectioned and stained for the following markers: SSEA-4 and human nuclear protein (HNP, FIG. 35); α6-integrin and HNP (FIG. 36); SSEA-4 and α6-integrin (FIG. 37). Negative controls consisted of human THT transplanted cells in mouse testis sections stained only with secondary antibody (FIG. 38). All stains contain a general nuclear dye.

Flow cytometry analysis confirmed immunohistochemical observation and positive populations for α6-integrin were found in samples collected from human testes. In addition a distinct population of Thy-1+ cells were found. Co-localization of Thy-1 and α6-integrin showed that there are three subpopulations of Thy-1+ cells within human testes: 1) aThy-1 medium and α6-integrin low, 2) a Thy-1 high and α6-integrin medium, and 3) a Thy-1 high and α6-integrin negative. Most of the α6-integrin+ cells were Thy-1−. There were also clear population of SSEA-4+ (10-12%) and GFR-α+ (1-5%) cells found in human testes. Magnetic sorting significantly enhanced the percentage of SSEA-4+ cells to 44% indicating a 4 fold increase for this marker.

Quantitative RT-PCR analysis revealed that among the samples tested SSEA-4+ cells and GFR-α+ cells express highest levels of spermatogonial stem cell markers including C-RET, PLZF, and TERT and germ cell markers including VASA and DAZL. Telomerase activity is indicative of spermatogonial stem cells. Spermatogonial stem cell transplantation revealed that SSEA-4+ cells colonize testes of recipient mice and repopulate, indicating that these cells are functional spermatogonial stem cells.

Figure 45A:
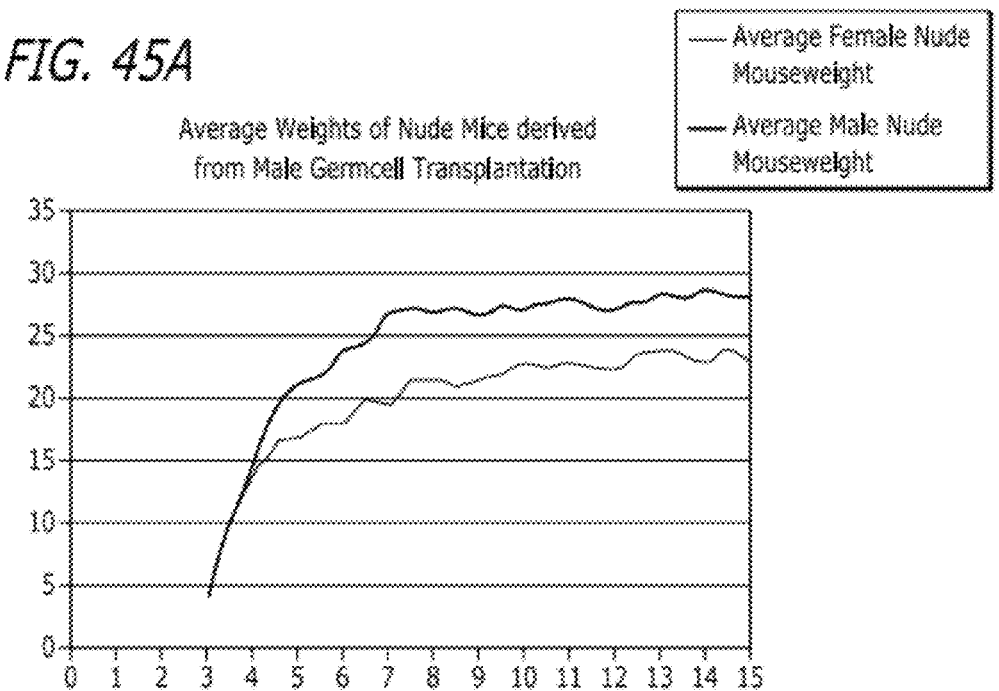
FIG. 45A depicts the nude offspring and FIG. 45B depicts the non-nude offspring.
Figure 45B:
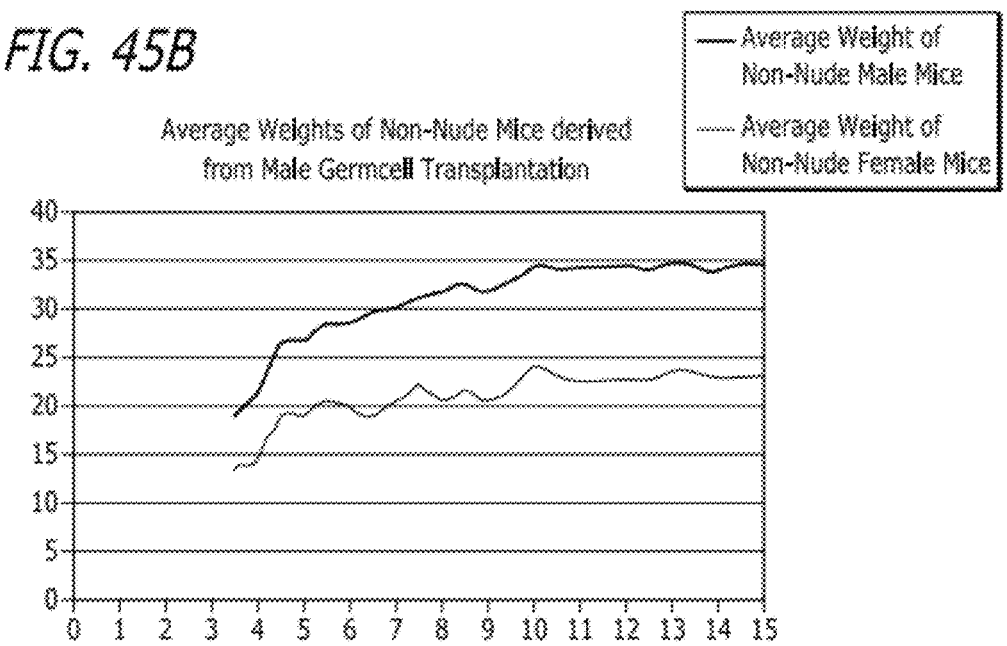

It has been shown that infertile male mice can be made fertile through transplantation of male germ line stem cells (GSC's) from a donor mouse and that these mice can then produce offspring. However, the properties of mice derived from this method had not been previously examined. The aim of this study was to determine the properties of mice derived from GSC transplantation and compared to the known growth patterns of the parental strain. FIG. 45 depicts the average growth of male (FIG. 45A) and female (FIG. 45B) F1 mice created through breeding of mice derived from male GSC transplantation. These growth rates are similar to the growth rates of the parental mice as provided by the vendor (data not shown).

Example 6

Phenotypic Characteristics of Human Spermatogonial Stem Cells

Human testicular cells were enriched for spermatogonial stem cells (SSCs) by magnetic sorting for SSEA-4 and the enriched population was microinjected into the testes of a recipient mouse. One month after transplantation, testes were harvested and cryosections were made. The identity of human cells in the mouse testes was determined using human nuclear protein (HNP) antibody conjugated to alexa-488. Co-localization of HNP with germ cell, somatic cells, stem cells and pluripotent markers (Table 3) were used to assess the phenotypic characteristics of human SSC in the mouse testes.

Extensive colonization of human cells as detected by HNP staining in the mouse testes indicates the presence of highly enriched population of SSC in the SSEA-4 magnetic sorted cells. All the human cells colonized the mouse testes were positively stained for germ cell marker VASA and negatively stained for LHR, a marker for testicular sertoli and leydig cells. This indicates that all the colonized cells are germ cells. Among the markers used in this study only 15% of the human cells expressed SSEA-4, 31% expressed α6-integrin and 45% of them expressed GPR125 on their surface. Almost all the human cells colonized mouse testes expressed c-Kit indicating that this marker is needed for SSC self renewal. Among the pluripotent markers testes, no Oct-4+ or TRA-160+ cells were found, but 29% of human cells showed Nanog expression. This indicates there is a population of cells among human SSCs with pluripotent characteristics. Almost all the SSEA-4 cells were also positive for α6-integrin. Also all the SSEA-4+ cells were positive for c-Kit indicating that only the c-Kit+ population of SSCs have the ability of colonization in the recipient testes.

TABLE 3

| Marker | Percentage of positive cells |
| --- | --- |
| VASA | 100 |
| LH-R | 0 |
| SSEA-4 | 15 |
| Alpha-6 integrin | 31 |
| GPR-125 | 45 |
| c-Kit | 96 |
| Nanog | 29 |
| Oct-4 | 0 |
| TRA1-60 | 0 |

This study clearly demonstrates that human SSCs have phenotypic characteristics of VASA+, c-Kit+, LHR−, TRA1-60−, Oct4− and subpopulations of human SSCs are SSEA4+, α6-integrin+, GPR125+ and Nanog+. This indicates that different populations of SSCs are present in human testes.

Luteinizing Hormone Receptor (LHR) does not co-localize with monkey, human, or mouse germ cells as indicated by VASA, SSEA4, GFRα, and α6-integrin co-localization studies. LHR is expressed on Sertoli and Leydig cells as indicated by the location and morphology of those positive cells. Connexin-43 appears to stain both germ cells located at the basement membrane, Sertoli cells, and possibly Leydig cells.

Example 7

Mouse Potency Assay

Fertility Assessment

Transplantation of male germline stem cells from a donor animal to the testes of an infertile recipient has been previously described. Donor germ cells colonize the recipient's testis and produce donor-derived sperm, such that the recipient male can distribute the genetic material of the germ cell donor. Germ cell transplantation represents a functional reconstitution assay for male germline stem cells and as such has vastly increased our ability to study the biology of stem cells in the testis and define phenotypes of infertility. First developed in rodents, the technique has now been used in a number of animal species, including domestic mammals, chicken and fish. There are major applications for this technology in animals: first, to study fundamental aspects of male germline stem cell biology and male fertility; second, to preserve the reproductive potential of genetically valuable individuals by male germ cell transplantation within or between species. Therefore, transplantation of male germ cells is a uniquely valuable approach for the study, preservation and manipulation of male fertility in animals.

To validate the GFP germ cell transplantation assay, the optimal transplantation number of GFP germ cells were determine for transplantation into busulfan treated mice. The optimum transplantation cell number of GFP germ cells is determined by mating of the transplanted GFP germ cell nude male mouse with a nude female mouse. The GFP+ offspring from those matings will determine if the transplanted GFP germ cells restored fertility and produced viable GFP offspring. The GFP offspring are then used to validate the GFP germ cell transplantion assay by comparing the parameters described below with the total cells transplanted and/or other parameters (marker expression, testes weight, etc.). After GFP pups are born, those GFP offspring from the transplanted GFP germ cell sire are used to verify fertility and germline transmission of GFP germ cells into the next progeny by mating again with nude mice.

Each individual GFP+ transplanted male mouse is mated with 4 nude female mice. Two females are mated with each male every night. The four females are cycled every night depending on their estrus cycle. The males will mate for three weeks, have a one week break, and begin another three weeks of mating if the females have not formed a vaginal plug. These procedures will give the females the optimum opportunity to become pregnant, while the break periods will allow the male to recover from continuous matings. Each morning, the mice are checked for vaginal plugs as a positive indicator of successful mating. This mating procedure is continued for 5-7 months post transplantation. If no females become pregnant, matings will continue for an additional 2 months.

After the mating period, the matings stop and testes from the GFP transplanted mice are analyzed by flow analysis, sperm analysis for GFP, and histology to determine the number of GFP+ and SSC+ marker expressed in the testis. The F1 progeny are also assayed for GFP using fluorescence and PCR. As nude mice do not have fur, any pup with fur should have been generated from the GFP positive sperm.

In order to assess the fertility and germline transmission of GFP or coat color from the F1 progeny, they are allowed to mature to the age of 2 months and then mated with 2 nude mice (male or female) for two months to ensure pregnancies. After the F1 mice produce F2 progeny, the F2 GFP+ and/or coat color+ mice will be screened for GFP with fluorescence and PCR. This will verify trans-generational germline transmission of the GFP+ cells. F2 progeny which prove to be GFP+ are then sacrificed and the reproductive organs collected for histology to verify complete spermatogenesis with GFP+ sperm.

Fresh testes cells isolated from prepubescent mice can restore fertility in busulfan-treated mice and 87% of the mice regained their fertility either by natural mating or using assisted reproductive techniques. To determine whether cryopreserved testicular cells can restore fertility, 5-8 week old male nude mice were treated with busulfan and the animals become infertile after a month. Cells from 2-5 days old prepubescent GFP+ pups were frozen and used as donor cells for transplantation. Mice received one of four treatment regimens: nine mice received cells ($5 \times 10^5$) that have been frozen manually; nine received cells ($5 \times 10^5$) that have been frozen with controlled rate freezing method; nine were received cells ($1.25 \times 10^5$) that have been frozen with controlled freezing protocol; and nine other received a smaller number of cells ($5 \times 10^4$) that have been frozen with controlled rate freezing protocol. Three months after transplantation, animals were mated with two females each and the efficiency of the mating was determined by plug check and the number of pregnancies and GFP pups were recorded. One of these animals that regained fertility, but produced nude pups, was sacrificed and the presence of GFP sperm was determined using flow cytometry and fluorescent microscopy (FIG. 46). Flow cytometry analysis of this showed that there is a small population of GFP+ sperm in the left testis while no GFP+ sperm were found in the right testes. GFP+ tubules were found in both right and left testis of the mouse indicating that transplanted cells have survived and colonized recipient testis. Based on flow data only 0.5% of the spermatozoa are GFP positive.

Example 8

In Vitro or In Vivo Maturation of Human or Mouse Spermatogonial Stem Cells (SSC) or Early Stage Spermatogenic Cells (ESSC) to Produce Viable Offspring Mammalian spermatogenesis is a highly synchronous process by which mitotic spermatogonia, meiotic spermatocytes, and haploid spermatids develop in close association with somatic Sertoli cells. Spermatogenesis is regulated mainly by endocrine factors and also by testicular paracrine/autocrine growth factors. These factors are produced by Sertoli cells, germ cells, peritubular cells and interstitial cells, mainly Leydig cells and macrophages. The interactions and the ratio between Sertoli and germ cells in the seminiferous tubules ensure successful spermatogenesis. Culture of spermatogonial stem cells (SSCs) has been hampered because of some obstacles such as the low number of stem cells in the testis, absence of specific markers to identify SSCs, in addition to difficulties in keeping the SSCs alive in culture. Recently, growth factors important for the proliferation and differentiation of SSCs have been identified, such as glial cell line derived neurotrophic factor (GDNF), stem cell factor (SCF) and leukemia inhibitory factor (LIF); also, markers for SSCs at different stages were reported. In vitro culture of SSCs can be used as a powerful tool in studying the biomolecular factors involved in the regulation of SSCs growth/proliferation and differentiation.

There are three options for ex-host maturation of spermatogenic cells: (1) ex host/in vivo maturation under the skin or testes of a surrogate animal, preferably non-human (reimplanation or autologous transplantation of spermatogonial stem cells into the same host is not considered ex host maturation and is covered elsewhere; (2) ex host/in vitro culture of the isolated spermatogenic cells, or (3) ex host culture of seminiferous tubules. Studies in variety of animal models demonstrated that xenotransplantation of testis segments from an immature stage under the skin or grafted to the testis of immunodefficient mice result in significant progression and in some cases complete spermatogenesis. Surprisingly, despite of the complete disruption of the testes structure and Sertoli-germ cell interaction, in mouse and bovine, some cells progressed to round and elongated spermatids with haploid DNA. In the mouse, ICSI demonstrated that these haploid cells are capable of fertilizing a mature egg. The advantage of culture of seminiferous tubules is that the intact structure of the seminiferous tubules is maintained since the seminiferous tubules are considered as the functional units of sperm production within the testis.

Example 9

Transplantation of Spermatogonial Stem Cells into Human Testis Using Ultrathin Endoscopic Microinjection Technique Spermatogonial stem cell transplantation technique in rodents was developed more than a decade ago using a glass capillary and micro dissection microscopy. In the mouse, the anatomy and size of the testis provides feasible access to rete testis via efferent ductus allowing fast and reliable transplantation of sufficient number of SSCs into the lumen of the seminiferous tubules by a single injection into the efferent ductus. Rete testis in rodents is visible from outside of the testis and is located in a far enough distance from the testicular artery and vein.

In larger mammals, however the anatomy and size of the testis is different. First, the rete testis is located in the testis in the close vicinity of testicular blood supply. Secondly, there are multiple efferent ducti connecting the rete testis to epidydimis. Finally the size of testes requires higher volume of cell suspension to fill in the testes (milliliter rather than microliter volumes). In bovine and monkey, ultrasound guided methods have been developed for transplantation of SSCs into the testes by injection of a large needle into the testes lumen. However these protocols are inefficient and invasive as in both methods the injection in some cases results damage to the rete testis and hemorrhage.

Also disclosed herein is a microinjection device for human testes allowing access from outside to human testis segments, including the epidydimis, and having the ability to maneuver into individual efferent ductus allowing access to rete testes without damaging the arteries and veins. This device consists of two parts: An endoscopic capillary catheter, which has a light source and a camera allowing the operator to guide the catheter, and an internal narrower catheter that passes through the ductus efferent and transfers the cell suspension into the rete testes. The catheter is inserted into the epidydimis via a small incision and is guided to the efferent dustus. Prior to cell injection, an ultrasound contrast solution (Levovist) is injected and the flow of the solution is monitored by an ultrasound device to ensure that the solution is passing through the rete testis into the seminiferous tubules.

Advantage of this device is non-invasiveness and reliable access to human testicular lumen. This device can also be used for diagnostic purposes of male infertility, for example finding the exact location of obstructive azospermia. The device can also be used to collect cells and tissue from epidydimis and rete testes in a less invasive manner.

Example 10

Prepubescent Male Germline Stem Cells and their Use in Infertility Treatment

Treatments for blood-borne cancers, which are the most common childhood cancers, tend to require alkylating agents, combined with total-body irradiation and bone marrow transplantation. These treatments not only destroy malignant cells, but may also have a cytotoxic effect on the rapidly dividing spermatogonia. As a result, spermatogenic failure and infertility may occur during adulthood. Adolescents and adult men have the option of cryobanking their semen before cancer treatment and, by artificial insemination, IVF or ICSI, they can father children who are genetically their own.

Prepubescent patients are at a greater risk of losing their fertility since they have not completed spermatogenesis. Their seminiferous epithelium contains only Sertoli cells and different types of spermatogonia, among which are the stem cells. Because of the absence of mature gametes, cryo-preservation of immature tissue is currently the only means by which fertility may be preserved in young boys.

Testis cell transplantations have been performed using donor testis from a wide variety of animals, mostly using immunocompromised mice as the recipient. The animals that have been used as donors in experiments where the recipient was mice includes; mice, rats, hamsters, rabbits and dogs, cattle, monkeys, and humans. Progeny derived from the donor testis cells has only been shown in mice and rats.

Strategies to preserve the fertility of prepubescent patients include the isolation and cryopreservation of germline stem cells. These germline stem cells can be auto-transplanted into the patient after chemotherapy and/or radiation therapy. However, autotransplantation of germline cells from cancer patients poses the risk of transmission of malignant cells. Therefore, germline cells should be completely isolated from malignant cells. Disclosed herein is a method, based on flow cytometry sorting, that differentially selects for germline stem cells and to purify them from cancer cells.

Also disclosed herein is a physiological relevance assay for germline stem cell transplantation. The results of the assay will allow decisions about the amount of stem cells needed to restore fertility. It is further used to evaluate stability, viability and potency of germline stem cells at the time of tissue collection and before release. A mouse model is used since surface markers for spermatogonial stem cells in this species are well characterized and a transplantation technique is available. This transplantation technique will test functionality of germline stem cells in the busulfan-treated immunodeficient mouse testes allowing complete progression of spermatogenesis of the donor cells in the recipient animal.

1. Determination of Suitable Antibodies for Testicular Support Cells.

Leutinizing hormone receptor (LHR) is a specific marker to differentiate germ cells from somatic cells. LHR only binds to Sertoli cells and Leydig cells in the testis.

TABLE 4

| Cell Surface Marker | | Intra-Cellular Marker | | Positive staining on Cell Types |
|---|---|---|---|---|
| Adult | Pre-pubescent | Adult | Pre-pubescent | |
| CD3620 | AMH | | Inhibin alpha | Sertoli, |
| Class I MHC | | Vimentin | Vimentin | Sertoli, |
| Leu M3 | | | Cytokeratin | Sertoli, |
| | CLA-1/SR-BI | | | Sertoli, Leydig, spermatid acrosome vessicle |
| | HSL | | | Sertoli, Leydig, spermatogonia, golgi region of spermatocytes, nucleus of spermatids |
| | | GalC | GalC | Sertoli, Leydig, connective tissue of intertubular space |
| A2B5 | | CNPase | CNPase | Sertoli, Leydig, connective tissue of intertubular space |
| Thy-1 | | GFAP | GFAP | Leydig |
| O4-antigen (O4) | | Nestin | | Leydig |
| | p75/NTR | | COL-1 | Connective Tissue PM cells in 13.5pc mice |
| | | | Inhibin βA | Connective Tissue PM cells in13.5pc mice |
| | | | Caldesmon1 | Connective Tissue PM cells in13.5pc mice |
| | | | Tropomyosin1 | Connective Tissue PM cells in13.5pc mice |

2. Separation of Germline Stem Cell from Cancer Cells

The objective of this study is to enrich germline stem cells while removing any tumor cells from a patient sample, a method is developed that differentially selects and isolates germline stem cells from a heterogeneous cell population; to quantify the selection process to a point where contaminating cancer cells have been depleted enough for clinical application. This includes the evaluation of how many cancer cells are required to initiate tumor growth. In order to treat each patient according to its disease phenotype, a method for disease specific immunophenotyping will be developed. To do this the specific cell surface marker expression for a specific cancer type will be assessed and used in the depletion of cancer cells from a patient sample.

The main concern of this procedure is the isolation of germline stem cells. A procedure for the negative selection of germ cells from leukemic mice by flow cytometry sorting has been established with antibodies against two surface markers expressed in blood cancer cells including MHC class I and common leukocyte antigen (CD45). This procedure leads to successful transplantation of mouse germline cells into recipient testes without transmission of leukemia in mice. For further exclusion of malignant cells, human germ cells are positively selected with specific markers for germ cells such as CD90, CD49f, SSEA-4 and GFR-α. In addition, other indicators for cancer can be employed such as DNA ploidy detection. The goal of this model is to restore fertility without reintroducing cancer into a patient.

The experiments will determine the feasibility of a positive or negative selection for germline stem cells, a threshold when a tumor can be re-transplanted in a mouse model and a disease specific surface marker expression topology.

3. Spermatogonial Stem Cell Potency Assay

To reach conclusions about the ability of different germline stem cell populations to restore fertility in busulfan-treated testis, a potency assay is needed. Each of the populations was compared to a negative control to determine the increase in efficiency. This allows conclusions about the necessity of co-transplanted cell types such as Leydig cells, Sertoli cells or myoid cells. Increasing amounts of germline stem cells should yield a higher efficiency of transplanted cells and restoration of fertility. To be able to unambiguously recognize donor cells from the recipient, germline stem cells are isolated from transgenic GFP mice (NAGY, Jackson Labs) testes. To mimic prepubescent human patients, juvenile male mice between 7-10 days were used for collection of germline stem cells.

TABLE 5

| Transplanted cells | Number of recipient mice | Total cells needed | Number of Donor pups | Mice for mating |
|---|---|---|---|---|
| $1.5 \times 10^6$ | 3 | $4.5 \times 10^6$ | 3 | 1 |
| $7.5 \times 10^5$ | 6 | $4.5 \times 10^6$ | 3 | 2 |
| $5.0 \times 10^5$ | 9 | $4.5 \times 10^6$ | 3 | 2 |
| $2.5 \times 10^5$ | 18 | $4.5 \times 10^6$ | 3 | 2 |
| $1.0 \times 10^5$ | 18 | $1.8 \times 10^6$ | 3 | 2 |
| 0 | 5 | 0 | 0 | 2 |
| Total | 59 | | 15 | 11 |

Transplantation Efficiency Analysis.

An active round of spermatogenesis lasts about 35 days in the mouse, therefore all but 2 of the transplanted mice were sacrificed 4 weeks after transplantation. The testis were dissected and weighed as an indicator of active spermatogenesis. The testes were then digested into a single cell suspension and the expression of GFP detected by flow cytometry. This allowed for the determination of the number of GFP+ cells originating from the donor stem cells. The testes were also assessed by flow cytometry for the same markers to reach conclusions about the amount of germline stem cells present originating from the donor and the endogenous recipient.

Detection of Restoration of Fertility.

The two remaining mice were used for mating 8 weeks post transplantation. Each male mated with two nude females. The generated offspring were assayed for their GFP expression or fur color to demonstrate what the originating strain was. The offspring from each transplanted mouse were observed for eventual abnormalities. Results are depicted in Table 6.

Example 11

Differentiating and Testing Functionality of Mouse Ovarian Cultured Germ Cells Ovarian tissue transplantation (OTT) is becoming an increasingly popular strategy for fertility preservation and propagation of ovarian follicles. The spectrum incorporates OTT in twins discordant for premature ovarian failure (POF) and to restore ovarian function (OF) in women with ovarian dysgenesis using ovarian tissue from matched donors, i.e. heterologous transplantation. Another proposed indication is to prolong the reproductive life in otherwise healthy women. The potential uses proposed for harvested ovarian tissue are: in vivo/in vitro maturation of primordial follicles, xenografting of ovarian tissue, or using a novel method to subsequently differentiate germ cells while using blood plasma clots and grafting them with ovarian tissue for maturation and development of oocytes.

are checked for follicle and oocyte development by histological examination. To test functionality of the differentiated transplanted cells co-grafted into host ovary, the mice are naturally mated to see if there are any functional oocytes that have differentiated, are fertilizable, and able to yield live pups from the transplanted cells. To test which clot method could be most successful for differentiation and propagation, four clot conditions co-grafted to host ovaries in the ovarian bursa and subcutaneous space are used: 1) cultured OG2 female GS cells on MEF (Day 0); 2) early EB's (2 day old) from cultured OG2 female GS Cells; 3) late oocyte-like cells from EB's (6 day old) from cultured OG2 female GS cells; 4) freshly isolated ovarian cells and follicles from 4-6 day old FVB GFP mice (used as a positive control).

Methods:

Germ Cell Embryoid Formation:

A 6-well plate containing a culture of OG2 female colonies is obtained at ~80% confluence (colonies had minimal contact with each other). The media is aspirated and the wells are washed once with PBS and 700 µL of warm trypsin was added to each well. The plate is then placed in a 37° C. incubator for 4 min. Each well of the E-well plate is

TABLE 6

| Animal # | Testis | Total # cells injected | Total # GFP+ cells injected | Total # GFP+/GFRα+ cells injected | Total # GFP+/α6+ cells injected | Total # GFP+/cKit− cells injected | Total # GFP+/ c-Kit−/α6+ cells injected | Fertile (Y/N), natural/ICSI |
|---|---|---|---|---|---|---|---|---|
| 1 | RT | 101,563 | 80,539 | 325 | 46,414 | 41,742 | 22,648 | Y, natural |
|   | LT | 113,281 | 89,832 | 363 | 51,770 | 46,559 | 25,262 |  |
| 2 | RT | 117,188 | 97,734 | 47 | 62,227 | 52,734 | 32,813 | Y, natural |
|   | LT | 101,563 | 84,703 | 41 | 53,930 | 45,703 | 28,438 |  |
| 3 | RT | 234,375 | 210,000 | 2,086 | 96,563 | 144,375 | 52,031 | Y, ICSI |
|   | LT | 234,375 | 210,000 | 2,086 | 96,563 | 144,375 | 52,031 |  |
| 4 | RT | 187,500 | 165,938 | 1,013 | 97,688 | 68,625 | 30,750 | Y, natural |
|   | LT | 250,000 | 221,250 | 1,350 | 130,250 | 91,500 | 41,000 |  |
| 5 | RT | 250,000 | 208,000 | 3,750 | 87,500 | 117,500 | 40,750 | Y, ICSI |
|   | LT | 250,000 | 208,000 | 3,750 | 87,500 | 117,500 | 40,750 |  |
| 6 | RT | 500,000 | 378,500 | 1,850 | 219,500 | 191,500 | 117,500 | Y, natural |
|   | LT | 468,750 | 354,844 | 1,734 | 205,781 | 179,531 | 110,156 |  |
| 7 | RT | 750,000 | 672,000 | 6,675 | 309,000 | 462,000 | 166,500 | Y, ICSI |
|   | LT | 750,000 | 672,000 | 6,675 | 309,000 | 462,000 | 166,500 |  |
| 8 | RT | 888,889 | 757,333 | 23,556 | 316,444 | 328,889 | 790,222 | N, ICSI ND |
|   | LT | 944,444 | 804,667 | 25,028 | 336,222 | 349,444 | 839,611 |  |
| 9 | RT | 1,000,000 | ND | ND | ND | ND | ND | Y, ICSI |
|   | LT | 1,000,000 | ND | ND | ND | ND | ND |  |
| 10 | RT | 234,375 | ND | ND | ND | ND | ND | N, ICSI ND |
|    | LT | 218,750 | ND | ND | ND | ND | ND |  |
| 11 | RT | 750,000 | ND | ND | ND | ND | ND | N |
|    | LT | 750,000 | ND | ND | ND | ND | ND |  |
| Total # |  | Range | Range | Range | Range | Range | Range | Total # |
| 11 |  | 101,563-1,000,000 | 80,539-672,000 | 41-6,675 | 46,414-309,000 | 41,742-462,000 | 22,648-166,500 | 8 |

RT = right testis;
LT = left testis;
ND = not determined;
α6 = α6-integrin

To develop a method of differentiating female mouse OG2 germ cells into follicles and/or oocytes by engrafting mouse OG2 germ cells with ovarian tissue cells together in blood plasma clots onto functional ovaries or by developing them engrafting into the subcutaneous space on the back of nude mice. The goal of the experiment is to determine if plasma clots function as a graft medium to differentiate germ cells into immature or mature oocytes while co-culturing them with functional ovaries. To test for early stages of follicle development, 4 cell-clots are engrafted into the subcutaneous space on the back of the nude mouse and one clot is removed once every 7 days for 28 days and the clots triturated to wash OG2 female cells off of the MEF layer and then breakup the MEF layer as much as possible. After each well is triturated all wells are micropipetted into a 50 mL conical tube containing an equal volume (4.2 mL) of PM1™+15% FBS+GFs. One mL of PM-1+15% FBS+GFs is used to wash out the first three wells of the 6-well plate and combined with cells from the previous step 6 and this step is repeated for the last three wells of the 6-well plate. The cells are then spun down at 400×g for 5 min and the supernatant aspirated with vacuum aspiration and then a 200 µL pipette is used to aspirate the remaining supernatant. The cells are resuspended in 8 mL of PM-1+15% FBS, no 3-mercaptoethanol, no GFs. Two mL of this cell suspension is pipetted into each of 4 wells of a 6-well non-adhesive plate and the plate is placed in a 37° C. incubator for 2-9 days with 50% media change every two days. The media is changed by pipetting 1000 μL of media in wells.

Digestion of Support Ovarian Tissue.

Ovaries of 4-8 day old LacZ/Oct4 GPF OG2 mice are isolated and bisected with fine dissection scissors. The bisected ovaries are transferred to 2 ml of HEPES-buffered DMEM containing 5% FCS and collagenase (1.5 mg/ml). Ovaries in digestion solution are incubated in a 37° C. water bath for 30 min, with gentle pipetting every 10 min. 12 ml of HEPES-buffered DMEM containing 5% FCS is added to stop the digestion of ovaries and digestion mixture after 30 min. The cells are spun at 80×G for 10 min at 4° C. Supernatant is removed and cells washed twice by centrifugation.

Preparing Ovarian Support Cells Mixture with Germ Cells for Differentiation.

The digested cells from one ovary are used as support cells for germ cells for each condition. 100K GS cells from each condition are added to one completely digested OG2/LacZ ovarian cell pellet. For only late EB from GS Cells (Day 6), instead of using 100K GS cells, 100 oocyte-like cells (40-70 μm) are manually picked and added to one completely digested OG2/LacZ ovarian cell pellet. The cell mixture is mixed completely with gentle tapping. Cells are spun at 80×G for 10 min at 4° C. then all the supernatant removed.

Making of Blood Plasma Clot.

The prepared cell mixtures are spun down at 80×G for 5 min. The supernatant is carefully removed and 20 μl of venous plasma is added. Re-suspend cells in venous plasma by gentle tapping to vortex cells and plasma. Remove 20 μl of plasma and cells and make a drop on 6 cm dish and add 0.5 μl of 1M $CaCl_2$ to the plasma drop. Cover the dish and place plasma drop with cells into 37° C. incubator. Incubate for 30 min to allow clot to form. After 30 min of incubation clots hardened to a gelatin like consistency and are ready for transplantation into the ovarian bursa next to the ovary.

Transplantation of Venous Clots with Germ Cells into Ovarian Bursa.

A 6-8 week nude mouse is anesthetized with 0.5 ml of Avertin. Wipe the back of the recipient mouse with 70% ethanol and then make two single small longitudinal incisions (less than 1 cm) in the skin with fine dissection scissors near the midline at the level of the last rib (one incision to the right of the midline and the other to the left of the midline). Slide the skin to the left or right until the incision is over the ovary (orange-pink) or fat pad (white), both of which are visible through the body wall. Then pick up the body wall with forceps and made a small incision (avoiding larger blood vessels) just over the ovary with forceps. Using a blunt forceps, pick up the fat pad and pulled out the left ovary, oviduct, and uterus, which will be attached to the fat pad. Slip a serrefine clamp onto the fat pad and laid it down over the back so that the ovary, oviduct, and uterus remained outside the body wall. Gently pick up the mouse and place it on the stage of a stereo microscope with its head to the left. Carefully find the ovary and made a tiny incision (2 mm) with fine dissection scissor into the ovarian bursa. Pick up previously made plasma clot with cells and carefully inserted clot into the tiny incision of the ovarian bursa. Using forceps, gently place the clot into the ovarian bursa incision site. Unclip the serrefine clamp and remove the mouse from the stage of the stereomicroscope. Use forceps to pick up the fat pad and place the ovary, oviduct, and uterus back inside the body wall. Sew up the body wall with one or two stitches (optional) and close the skin with wound clips. Repeat on the opposite side (right side) of the mouse. The following day checked on general health of transplanted mouse. Seven days after transplantation wound clips are removed.

Transplantation of Venous Clots with Germ Cells into Subcutaneous Space in the Back of Mouse.

While the mouse is still under anesthesia from implantation in ovarian bursa, use scissors to separate muscle from skin from the two original incision sites. Insert two clots for each incision site (total of 4 clots per mouse) into the subcutaneous space. Insert one clot to the right of the incision site and the other clot to the left of the incision site. Repeat procedure for the second incision site for the additional 2 clots. One subcutaneous inserted clot is removed once every 7 days for 28 days by surgical removal. The removed clots are fixed in 5 ml of 4% paraformaldhyde, embedded in OTC, cryo-sectioned at 8 μm and stained with heamatoxylin and eosin to shoe if differentiation and propagation of follicles are forming by morphology. Slides are stained with oocyte specific antibodies if necessary.

Mating of Transplanted Nude Mice.

Transplanted nude mice are checked 21 days after surgery and then daily to determine if mouse was in estrus. Closure of the introitus is taken as an indication of estrogen deficiency and re-opening as a sign that oestrogenic follicles has emerged in the graft. After vaginal opening or 3 weeks post-operation (whichever was earlier), host females are paired with fertile males. The females are inspected daily for signs of mating (vaginal plugs). Those that mated re allowed to litter. At 6-12 weeks after transplantation, all the hosts are autopsied, the status of the reproductive tract is examined, and the graft from the ovarian capsule is removed and fixed in 5 ml of 4% paraformaldhyde, embedded in OTC, cryo-sectioned at 8 μm and stained with heamatoxylin and eosin.

Example 12

Identification and Characterization of Repopulating Spermatogonial Stem Cells from the Adult Human Testis Spermatogonial stem cells (SSCs) maintain spermatogenesis by self renewal and continuous production of spermatozoa during the entire life. Histological and ultra structural studies revealed that in non-primate mammals, the $A_s$ (A single) spermatogonia are considered to be the stem cells of spermatogenesis. Upon division of the A spermatogonia, the daughter cells either migrate away from each other and become two new stem cells, or stay together through an intercellular bridge and become A-paired (Apr) spermatogonia. The Apr spermatogonia develop further into chains of four, eight or 16 A-aligned (Aal) spermatogonia. The Aal spermatogonia differentiate into A1 spermatogonia and after six mitotic divisions result in A2, A3, A4 and, finally, B spermatogonia, which give rise to spermatocytes at the last mitotic division.

Unlike rodents, in human and other primates classical histological studies of nuclear morphology indicate that two types of undifferentiated spermatogonia are present on the basement membrane of testicular seminiferous epithelium, designated as $A_{dark}$ and $A_{pale}$ spermatogonia. Morphological characterization of spermatogonial stem cells on testicular biopsies from patients having undergone semicastration for malignant tumors and radio- and chemotherapy showed that the stem cells of the human testis most likely are the $A_{pale}$ spermatogonia, recent studies in adult Rhesus monkey testes also revealed that $A_{dark}$ spermatogonia represent a reserve stem cell population which rarely divide and are activated following cytotoxic insult, whereas $A_{pale}$ spermatogonia are active stem cells that undergo regular self-renewing divisions to maintain spermatogenesis under normal circumstances. This indicates that both human and primate spermatogenesis have similar ontogeny, thus characteristics of the subpopulations of SSCs between these two species might be similar.

In general, due to the unavailability of specific markers, phenotypic and molecular characteristics of SSCs in adult human testes are poorly understood. Using rhesus monkeys, enriched populations of SSCs from the adult primate testes were characterized and isolated. Using selected markers found at the surface of the primate SSCs, the identity of different populations of SSCs in the adult human testes was investigated. In addition, enriched populations of human SSCs were transplanted into the recipient mouse testes and the identity of the repopulating human spermatogonial stem cells in the recipient mouse testes was investigated.

Materials and Methods

Tissue Preparation and Cell Isolation.

Testicular tissues devoid of tumor contamination were obtained from patients who underwent an orchiectomy and were generously donated by two patients. Testicular biopsies were obtained from patients undergoing the TESE (testicular biopsy and testicular sperm extraction) procedure. All patients have signed the informed consent form prior tissue collection. A small portion of tissue was extracted and used in this study. Testicular tissues and biopsies were surgically removed, placed in PBS supplemented with penicillin/streptomycin and transported from as little as two hr to overnight on ice. Testicular tissue samples were taken for histology and molecular biological analysis. Seminiferous tubules of the remaining tissue were finely minced and digested with collagenase A (1 mg/mL) and DNase (10 U/mL) in a reciprocating 37° C. water bath for 15 min. After collagenase digestion, the undigested tissue was allowed to settle and cells in the supernatant were removed. The undigested tissue was further digested in an enzyme cocktail consisting of 1.5 mg/mL collagenase A, 1.5 mg/mL hyaluronidase type V, 0.5 mg/mL trypsin, and 10 U/mL DNase in DMEM in a reciprocating 37° C. water bath for 20 min. After straining out remaining undigested tissue, isolated cells were centrifuged at 400 g for 10 min. Cell pellets were re-suspended in MEM+HEPES+5% FBS and placed in tissue culture coated 15 cm dishes in a 5% $CO_2$ humidified incubator until analysis. Testicular biopsy samples were only digested in the enzyme cocktail and were generally used for only one purpose due to their small size.

Flow Cytometry and Magnetic Sorting.

For cell surface characterization and sorting, cells were stained with selected stem cell markers used for characterization of primate SSCs including CD90-FITC, CD49f-PE, and CD117-APC and SSEA-4 (Table 10). Cells were stained for 30 min in MEM+HEPES+5% FBS (complete medium) on ice, washed once, and re-suspended in complete medium and kept on ice until flow analysis. Flow analysis was accomplished on an InFlux Cell Sorter. Fluorescein (FITC) and phycoerythrin (PE) were excited with a 488 nm 200 mW laser and emission was collected with 530/40 and 580/30 band pass filters, respectively. Allophycocyanin (APC) was excited with a 638 nm 25 mW laser and emission was collected with a 670/40 band pass filter. For magnetic sorting, cells (up to $200\times10^6$) were resuspended in DMEM+ 10% FBS and SSEA-4-biotin was added (1:200) and was incubated on ice for 1 hr. Labeling buffer containing PBS, BSA (0.5%) and 2 mM EDTA is prepared and degassed for 10 min. Labeling buffer was added to the SSEA-4 stained cells and centrifuged at 400 g for 10 min. SSEA-4 cells resuspended in 1.8 mL of buffer and 200 µL of streptavidin microbeads was added. Also 100 µL of SSEA-4-FITC conjugated antibody was added to be able to check the purity of the magnetically separated cells by flow cytometry. and incubated at 4° C. for 20 min. 10 mL of buffer added to the tube, centrifuged at 400 g for 7 min.

Histological and Immunohistochemical Staining.

Tissues were fixed overnight in 4% paraformaldehyde (PFA) and transferred into 20% sucrose for overnight equilibration. Tissues were frozen in OCT compound and cryo-sections were prepared at 8 µm thickness and stored at −80° C. For histology, sections were washed in PBS and stained with Mayer hematoxilin for 5 min, washed with distilled water for 5 min and mounted using an aqueous mounting medium. The sections were then analyzed using brightfield microscopy. For immunohistochemical staining, testicular sections were blocked and permeabilized using 0.1% Triton-X/2% BSA/5% sheep serum. Slides were then stained with germ cell and SSC specific antibodies as described in Table 10. DAPI was used for nuclear visualization. Following multiple washes in distiled water cells were preserved using aqueous fluorescent preservative. Slides were analyzed using an Olympus BX-61 microscope with SlideBook™ imaging software. For quantification studies, approximately 25 tubule cross sections per slide were counted and the data from 4 slides were pooled together and presented in this study.

RNA Extraction and Real Time PCR Analysis.

Total cellular RNA was isolated using RNeasy Mini Kit (Qiagen Inc.) according to the manufacturer's recommendations. The isolated RNA was then transcribed to cDNA using the Quantitect RT kit (Qiagen) and later purified with the QIAquick PCR purification kit (Qiagen). For each RT-PCR reaction, 20 ng of cDNA template was used in a 25 µL reaction volume with HotStar Taq Plus (Qiagen) and respective primers (Table 11). All targets were amplified for 30 cycles. Amplification products were identified by size on a 2% agarose gel. For QRT-PCR, 5 ng of cDNA template was used in a 25 µL reaction volume with Quantitect Sybr Green PCR master mix (Qiagen) and run on a BioRad iCycler. Each sample was assayed in triplicate and normalized to a GAPDH control.

TABLE 10

| Antigen | Antibody Source | Working Dilution | Method |
| --- | --- | --- | --- |
| CD49f | BD Pharmingen | 1:100 | Flow cytometry |
| CD49f | Santa Cruz Biotech. | 1:200 | ICC |
| CD29 | Chemicon | 1:100 | Flow cytometry |
| CD90 | BD Pharmingen | 1:100 | Flow cytometry |
| CD117 | BD Pharmingen | 1:100 | Flow cytometry |
| CD117 | Santa Cruz Biotech. | 1:100 | ICC |
| SSEA-4 | eBiosciences | 1:200 | Flow cytometry |
| SSEA-4 | Chemicon | 1:200 | ICC |
| SSEA-4-biotin | eBiosciences | 1:200 | MACS |
| Streptavidin microbeads | Miltenyi Biotec | 1:20 | MACS |
| GFR-α1 | R&D Biosystems | 1:100 | Flow cytometry, ICC |
| GPR-125 | Abcam | 1:250 | ICC |
| Oct-4 | Santa Cruz Biotech | 1:50 | ICC |
| Tra-1-60 | Chemicon | 1:100 | ICC |
| DDX4 (VASA) | Abcam | 1:200 | ICC |
| VASA | R&D Biosystems | 1:100 | ICC |

TABLE 10-continued

| Antigen | Antibody Source | Working Dilution | Method |
|---|---|---|---|
| Nanog | Bethyl | 1:100 | ICC |
| HNP | Chemicon | 1:250 | ICC |
| Alexa 488 | Invitrogen | 1:500 | ICC |
| Alexa 568 | Invitrogen | 1:500 | ICC |
| FITC | Jackson | 1:200 | Flow cytometry |
| DAPI | Invitrogen | 1:10.000 | ICC |
| TO-PRO-3 | Invitrogen | 1:100 | Flow cytometry |
| Hoechst 33342 | Invitrogen | 1:1000 | Flow cytometry |
| Alexa 488 antibody labeling kit | Invitrogen | | ICC |

TABLE 11

| Gene | 5' sequence | 3' sequence | DNA size (bp) |
|---|---|---|---|
| C-Kit | AGGTGACACTATAGAATAGCA CGGTTGAATGTAAGGCT (SEQ ID NO: 1) | AGGTGACACTATAGAATAGCAC GGTTGAATGTAAGGCT (SEQ ID NO: 2) | 151 |
| GFRα1 | AFFTFACACTATAGAATATCAG CAAGTGGAGCACATTC (SEQ ID NO: 3) | GTACGACTCACTATAGGGAAGCA TTCCGTAGCTGTGCTT (SEQ ID NO: 4) | 256 |
| PLZF | AGGTGACVACTATAGAATATT CATCCAGAGGGAGCTGTT (SEQ ID NO: 5) | CTACGACTCACTATAGGGACCTC GTTATCAGGAAGCTCG (SEQ ID NO: 6) | 155 |
| c-Ret | AGGTGACACTATAGAATAACA TTGCCCAGCAACTTAGG (SEQ ID NO: 7) | GTACGACTCACTATAGGGAGGT GGCTCCTTTCTCAACTG (SEQ ID NO: 8) | 219 |
| GPR125 | AGGTGACACTATAGAATACTT GGCGCAGATGTGATAGA (SEQ ID NO: 9) | GTACGACTCACTATAGGGAGAA AAGTTGGCTGCTTCCAC (SEQ ID NO: 10) | 215 |
| Dppa5 | AGGTGACACTATAGAATAG AAAGTTCCCGAAGACCTGA (SEQ ID NO: 11) | GTACGACTCACTATAGGGAACTG GAGCATCCACTTGGTC (SEQ ID NO: 12) | 252 |
| FGFR3 | AGGTGACACTATAGAATATG GGTTTTCTCATCACTCTGC (SEQ ID NO: 13) | GTACGACTCACTATAGGGAGTT GGACTCCAGGGACACCT (SEQ ID NO: 14) | 247 |
| hTERT | AGGTGACACTATAGAATATT GTCAAGGTGGATGTGACG (SEQ ID NO: 15) | GTACGACTCACTATAGGGAGG CTGGAGGTCTGTCAAGGT (SEQ ID NO: 16) | 227 |

Telomerase Assay.

The SYBR Green real time quantitative telomeric repeat amplification protocol (RQ-TRAP) has been adapted from Wege et al (Wege H, Chui M S, Le H T, Tran J M, Zern M A (2003) SYBR Green real-time telomeric repeat amplification protocol for the rapid quantification of telomerase activity. Nucl. Acids Res. 31, e3.). Tissue or cell pellets were washed once in PBS and re-suspended and homogenized in a prepared lysis buffer containing 1× Chaps lysis buffer and 400 U/ml RNaseOut Inhibitor at a volume of 1,000 cells/μl. After 25 min of incubation on ice, the cell lysates were centrifuged at max speed for 10 min at 4° C. The supernatant was then transferred to a new micro centrifuge tube and the protein concentrations were determined at A280 nm with the ND-1000 spectrophotometer. Reactions were done in 25 μl volumes containing 500 ng protein lysate, Quantitect SYBR Green PCR mix (Qiagen), 1 μg TS primer, 0.5 μg ACX primer, and nuclease-free water. For every reaction plate assayed, each sample was tested in triplicate along with a no template control (lysis buffer), a positive control (ESC cells), and a standard curve prepared from Human ESC protein lysates (1000 ng, 200 ng, 40 ng, 8 ng, 1.6 ng). Using the iCycler iQ5 (Bio-Rad), the reactions were incubated for 20 min at 25° C., for 15 min at 95° C., and amplified in 40 PCR cycles for 30 seconds at 95° C. and 90 seconds at 60° C. The threshold cycle values (Ct) were determined from semi-log amplification plots (log increase in fluorescence versus cycle number) and compared with the standard curve. The software default setting for the threshold is 10 times the mean of the standard deviation of the fluorescence reading of each well over the first 10 cycles, excluding cycle 1. Telomerase activity was expressed as a percentage relative to human ESCs.

Spermatogonial Stem Cell Transplantation.

Spermatogonial stem cell transplantation technique was used to test the functionality of cell populations by colonization in recipient mice testes. Eight week old immune deficient Athymic Nude-Foxn1$^{nu}$ male mice (Harlan) were treated with a single intraperitoneal busulfan injection (40 mg/kg) and were used as recipients. One month after busulfan treatment, 0.3-0.8×10$^6$ SSEA-4+ magnetically sorted adult human testicular cells were transplanted into the seminiferous tubules via rete testis injection. Four weeks after transplantation, the mice were sacrificed and the testes were fixed in 4% PFA and cryosections were made. The identity of human spermatogonial stem cells in the mouse testes was recognized using human nuclear protein antibody in combination with other stem cell or germ cell markers. All animal experiments were conducted in accordance with the National Research Council's Guidelines for the Care and Use of Laboratory Animals.

Statistical Analysis.

Except otherwise indicated all the experiments are repeated three times. Two sample student T test and ANOVA test were used for statistical analysis and $P<0.05$ was considered as significant.

Results

Isolation and Enrichment of Spermatogonial Stem Cells.

Cells isolated from testicular biopsies collected from obstructive azoospermic men showed similar morphology and distribution of spermatogenic cells to the normal human testes indicating that spermatogenesis is in progress in these patients. On average $0.5 \times 10^6$ cells was isolated from each sample with the viability of 87%. Spermatogonial stem cells were morphologically detectable among the other cells as round cells with large nucleus to cytoplasm ratio, 1-3 nucleoli and cytoplasmic Inclusions (FIG. 39). For enrichment of spermatogonial stem cells dissociated cells from adult human testicular tissues were analyzed for various cell surface markers using flow cytometry. Expression profile of adult human testicular cells stained with various stem cell markers are presented in FIG. 43. Among the surface markers used for characterization of SSCs, SSEA-4 has been shown to be expressed on SSCs in the adult Rhesus monkey testes, was abundantly expressed in the human testes. Human testicular cells isolated from both testicular biopsies and donated tissues were tested and it was found that 13.3±1.4% of cells express SSEA-4 on their surface. Another subset of SSC markers that have been described in rodent and primate testes are CD49f ($\alpha$6-integrin), CD90 (Thy-1), CD117 (c-Kit), and in combination CD49f+/CD90+/CD117−(Triple Stain). In the adult human testes, 25±2.5% of cells express CD49f and 13±5% are CD90+. Interestingly, in contrast to the monkey testes, there was no population of Triple Stained cells in the human testes. (FIG. 39E-H)

Histological and Immunohistochemical Staining of Testicular Sections.

Figure 39A:
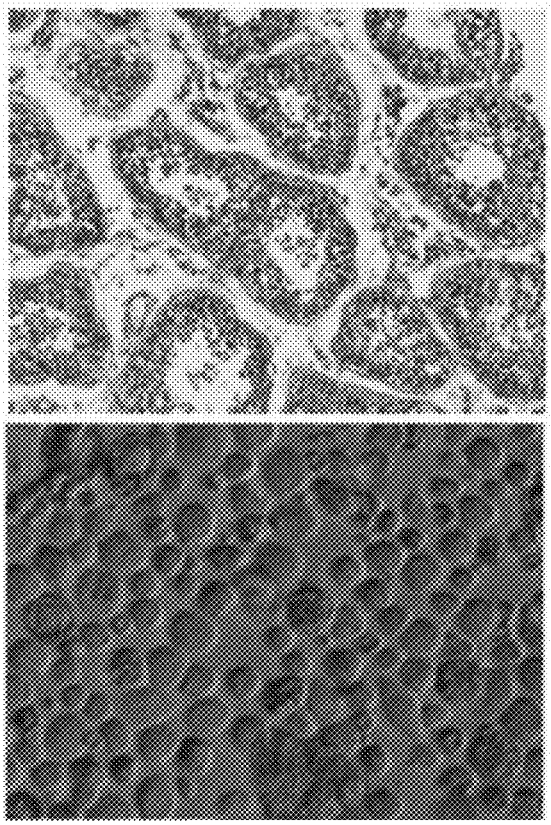
FIG. 39 depicts the morphology and cell surface marker analysis of adult human testicular cells. Note the morphology of the testes obtained from the obstructive azoospermic men (FIG. 39A) are similar to normal human testes (FIG. 39B). Also after isolation cells with similar morphologies were obtained from both normal testes (FIG. 39C) and testes collected from azoospermic patients (FIG. 39D). Note SSCs were present in both testes isolates and could be identified as round cells with large nucleus:cytoplasm ratio, 1-3 nucleoli and cytoplasmic inclusions. Flow cytometry analysis of surface markers SSEA-4, CD49f and CD90 in isolated cells from adult human testes (FIG. 39E-H). Distinct populations of SSEA-4+, CD49f+ and CD90+ cells were found in the adult human testicular biopsies and no population of double stained cells for CD49f and CD90 was found in the adult human testes (FIG. 39E-F). Histogram representation of four independent flow analyses is presented in FIG. 39I.
Figure 39B:
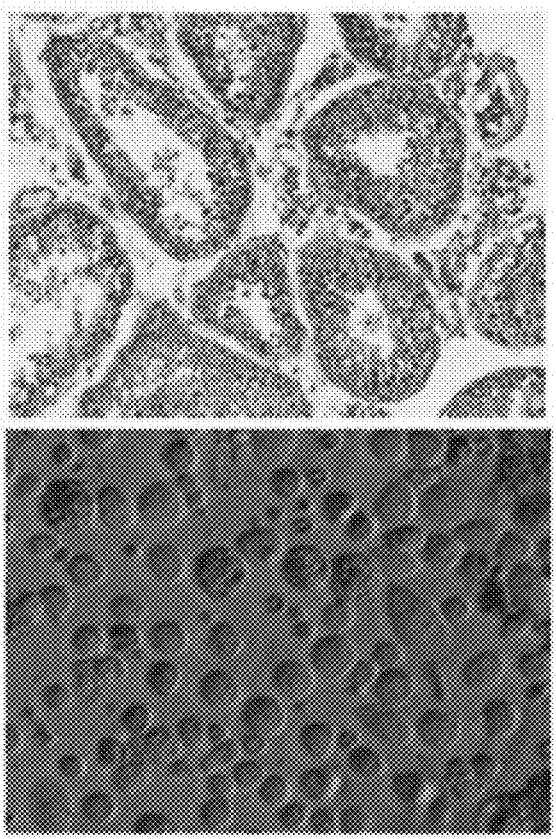
Figure 39C:
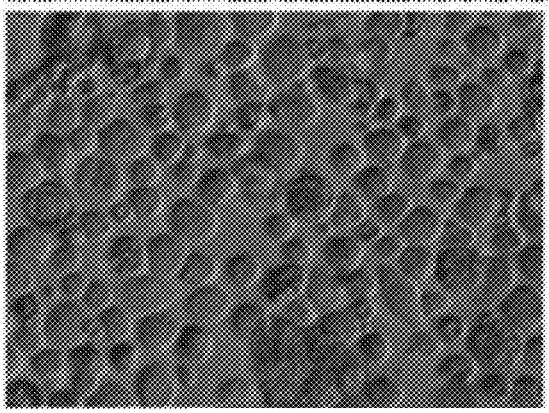
Figure 39D:
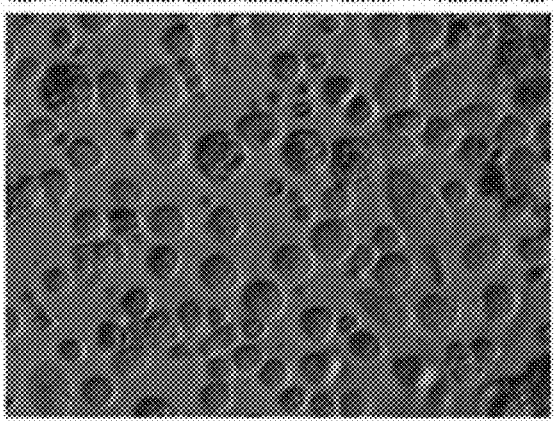
Figure 39E:
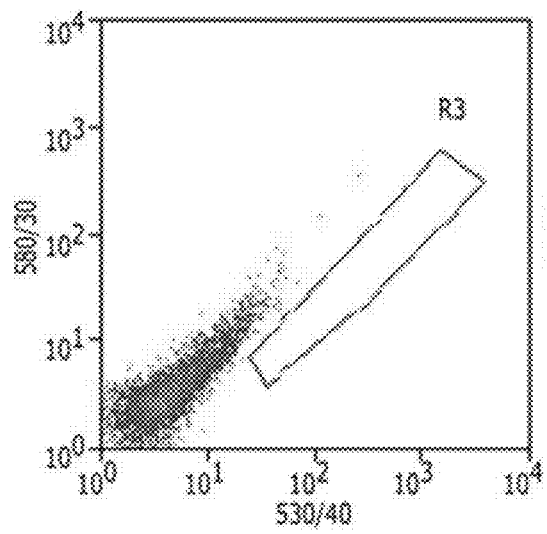
Figure 39F:
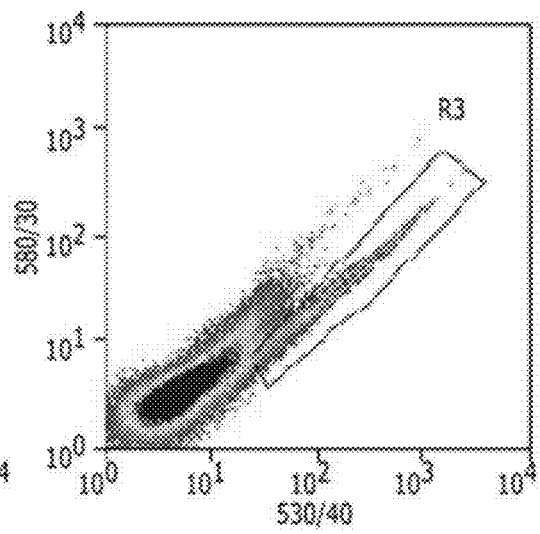
Figure 39G:
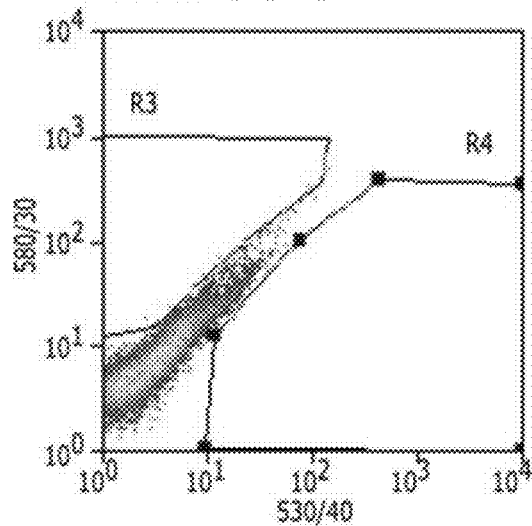
Figure 39H:
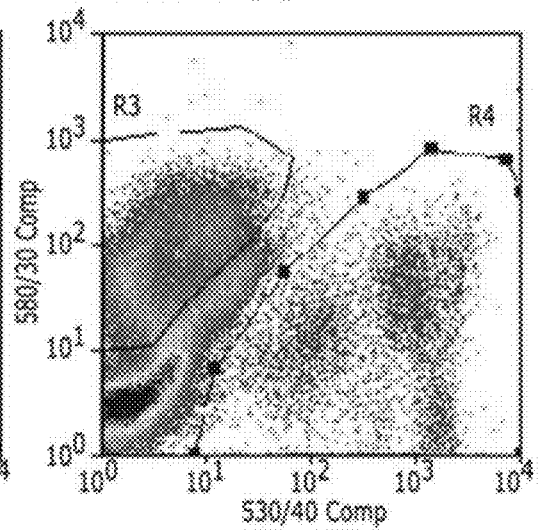
Figure 39I:
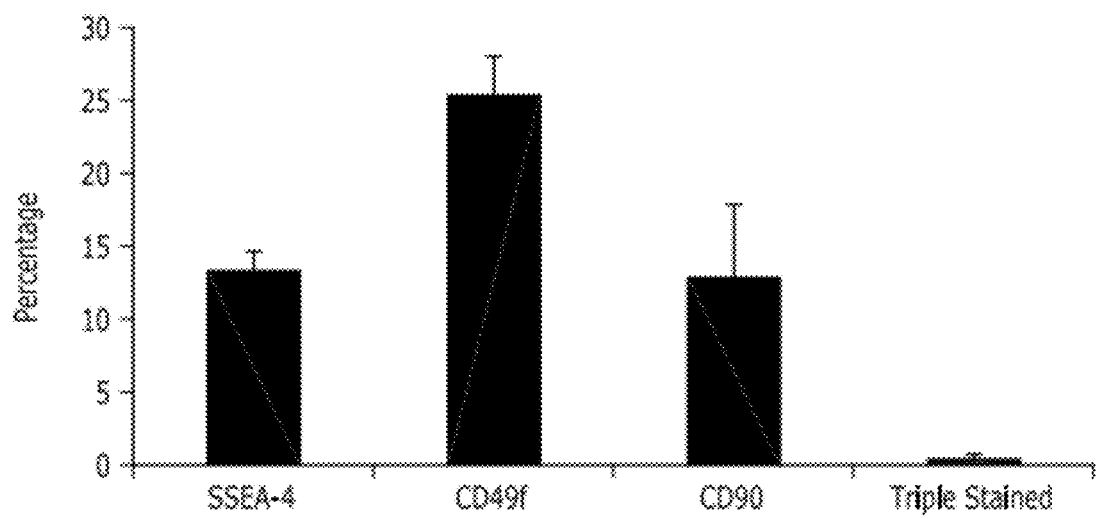
Figure 40:
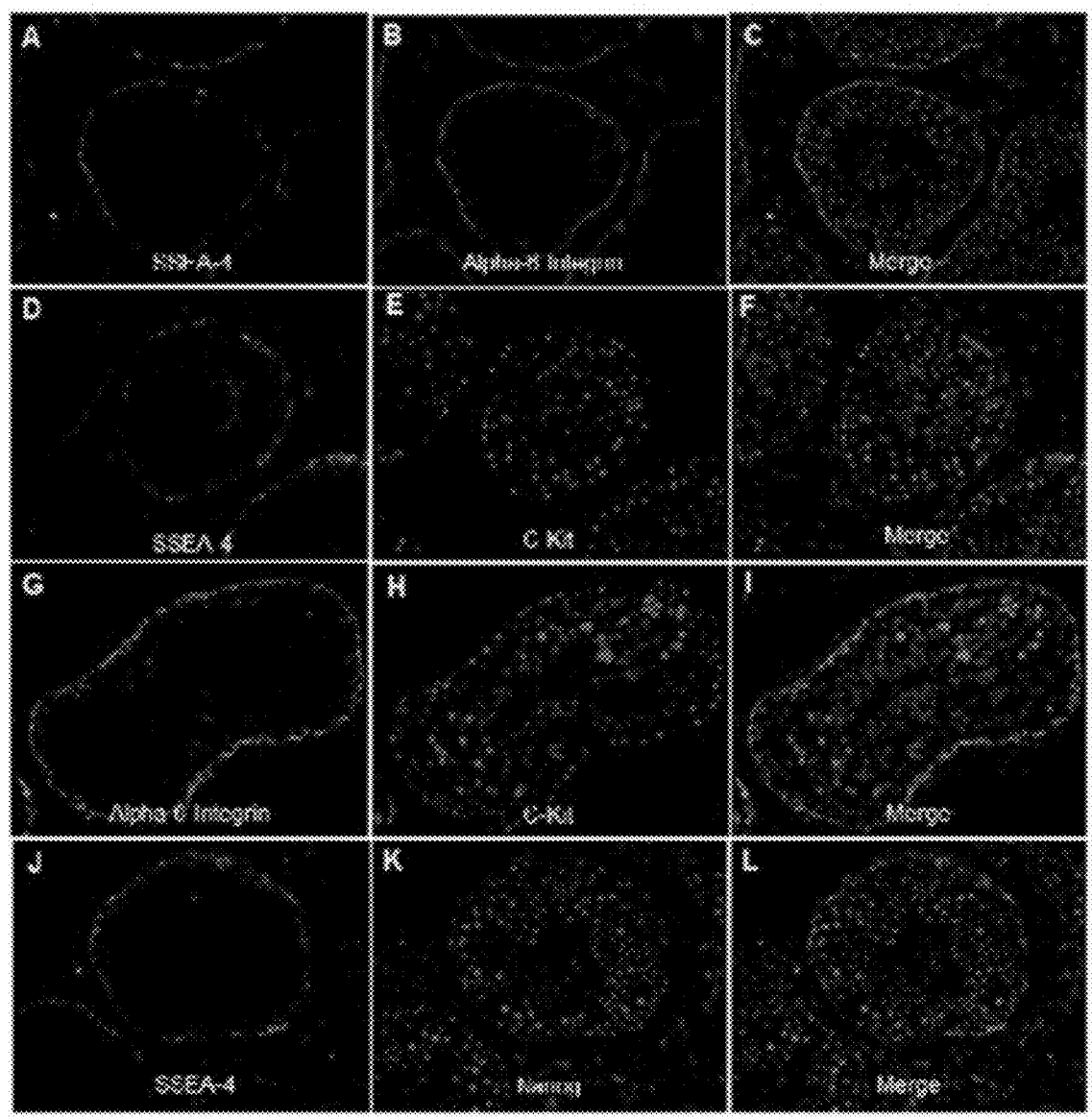
FIG. 40 depicts the immunohistochemical localization of spermatogonial stem cell markers in adult human testes. Co-localization of SSEA-4 and CD49f at the basement membrane of seminiferous tubules (FIG. 40A-C). SSEA-4 is specifically localized in subpopulation of spermatogonia at the basement membrane of the seminiferous tubules presumably the SSCs. All SSEA-4+ cells were also positive for CD49f, while there are some CD49f+ cells that are SSEA-4-. C-Kit was found in both cells located at the basement membrane of seminiferous tubules and in more advanced germ cells (FIG. 40D-F). Co-localization of SSEA-4 and c-Kit revealed that some of the SSEA-4+ cells possess c-Kit and some are c-Kit-. Co-localization of CD49f with c-Kit (FIG. 40G-I) showed that the majority of CD49f+ cells at the basement membrane of tubular cross sections were also positively stained for c-Kit. Expression pattern of Nanog in adult human testes was similar to c-Kit and it was present in both undifferentiated and differentiated germ cells (FIG. 40J-L). Co-localization of SSEA-4 with Nanog showed that some of the SSEA-4+ cells in adult human testes are Nanog+.

Histological examination revealed that testicular biopsies have a similar morphology when compared to the donated tissues after hematoxylin-eosin staining (FIG. 39A-B). Human testicular tissues were taken for immunohistochemical examination to better understand the distribution and marker expression of human SSCs. SSEA-4 and CD49f, also known as $\alpha$6-integrin, have interesting staining patterns in adult human testes, which is very similar to previous observations in the monkey testes (FIG. 40). According to histological quantifications, almost all of the germ cells adjacent to the basement membrane of seminiferous tubules express CD49f (28.7±1.2 per tubule cross section), a marker that has been found at the surface of rodent and monkey SSCs and other multipotent stem cells. Also, many of the cells along the basement membrane of seminiferous tubules express SSEA-4 (18±1 per tubule cross section), a pluripotent marker found in human embryonic stem (ES) and embryonic germ (EG) cells and adult Rhesus monkey SSCs. Interestingly, the majority (88.3%) of SSEA-4+ cells co-localize with CD49f. No specific immunoreactions were found for CD90 in the adult human testes. Unexpectedly, it was observed that most germ cells localized c-Kit, a receptor for stem cell factor and an early marker for germ cell differentiation, in the nucleus rather than on their surface. Approximately 75% of SSEA-4+ cells co-localized with c-Kit, suggesting the possibility of the existence of two different populations of SSCs in adult human testes. Also co-localization of CD49f and c-Kit showed that the majority (73.6%) of the CD49f+ cells at the basement membrane of seminiferous tubules co-express c-Kit which is very similar to that of SSEA-4. All the SSEA-4+ cells were also positive for germ cell marker VASA while only 50% of CD-49f+ cells showed VASA staining indicating that CD-49f is also expressed at the surface of the testicular somatic cells. Contrary to this, luteinizing hormone receptor (LHR) is not expressed on VASA+ cells in the seminiferous tubules, but appears to stain the cytoplasm of Sertoli and Leydig cells in human testes, indicating that LHR is expressed only in the somatic cells and not germ cells in adult human testes (FIG. 44). There were clear populations of cells at the basement membrane of human testes expressing Oct-4 indicating the existence of a population of cells among human SSCs with pluripotent characteristics.

Real Time PCR and Telomerase Assay.

Figure 41A:
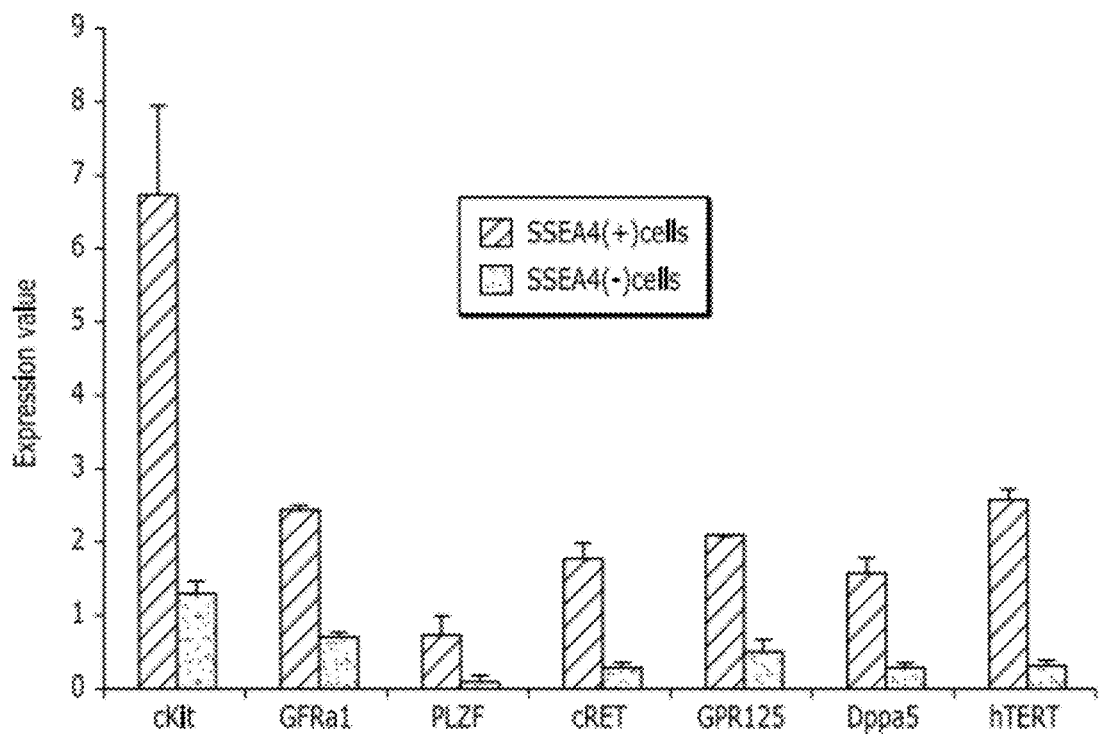
FIG. 41 depicts the quantitative RT-PCR analysis and telomerase activity of enriched population of SSCs isolated from adult human testes. SSEA-4+ cells showed significantly ($P<0.05$) higher expression levels of SSC specific genes including GFR-α1, C-Ret, GPR-125 and hTERT (FIG. 41A). In addition, c-Kit was remarkably increased in the SSEA-4+ cells as compared to the negative cells. Telomerase activity of SSEA-4+ cells was also significantly ($P<0.01$) higher than freshly isolated non sorted cells (FIG. 41B).
Figure 41B:
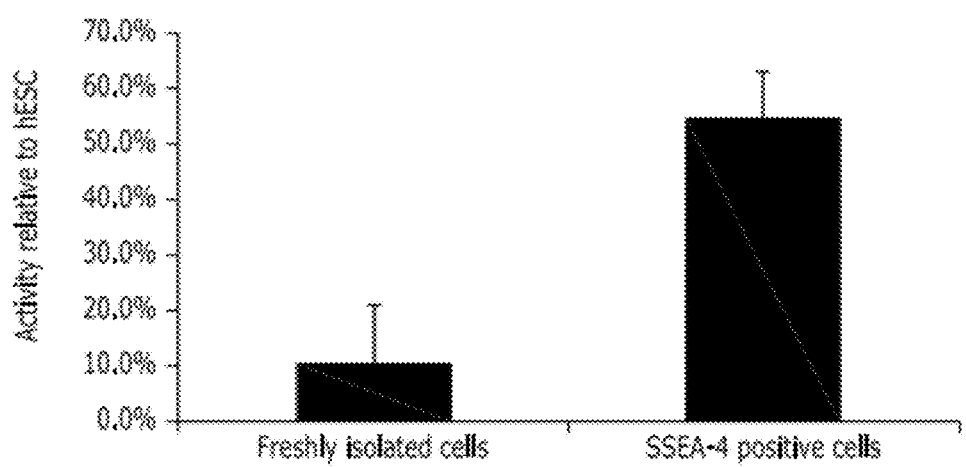

Gene expression analysis was performed on SSEA-4+ and SSEA-4− cells to test for spermatogonial stem cell specific expression. All of the genes including c-Kit, GFR$\alpha$-1, PLZF, c-RET, and GPR-125 were expressed at least 3-fold and up to 7-fold greater in the SSEA-4+ population (FIG. 41A). Remarkably, SSEA-4+ cells showed a much higher (24-fold) expression level for FGFR-3 (data not shown), indicating that FGFR-3 and its ligand FGF9 might be involved in human SSC proliferation and self-renewal. Moreover higher expression level of h-TERT in SSEA-4 sorted cells indicates their high level of telomerase activity and their repopulation capability. SSEA-4 positively sorted cells were compared with none sorted cells from the testis against human embryonic stem cells (hESCs) for telomerase activity (FIG. 41B). The none sorted cells showed an average of 10.4%±10.32% telomerase activity as compared to hESCs (100%), while SSEA-4+ cells had about 5-fold more expression as compared to the none sorted cells 54.6% (+/−7.8%), which is also approximately 2-fold less than hESC telomerase expression. This supports the finding of upregulated h-TERT expression and suggests at least prolonged replication capabilities in SSEA-4 positive cells.

Spermatogonial Stem Cell Transplantation.

Figure 42:
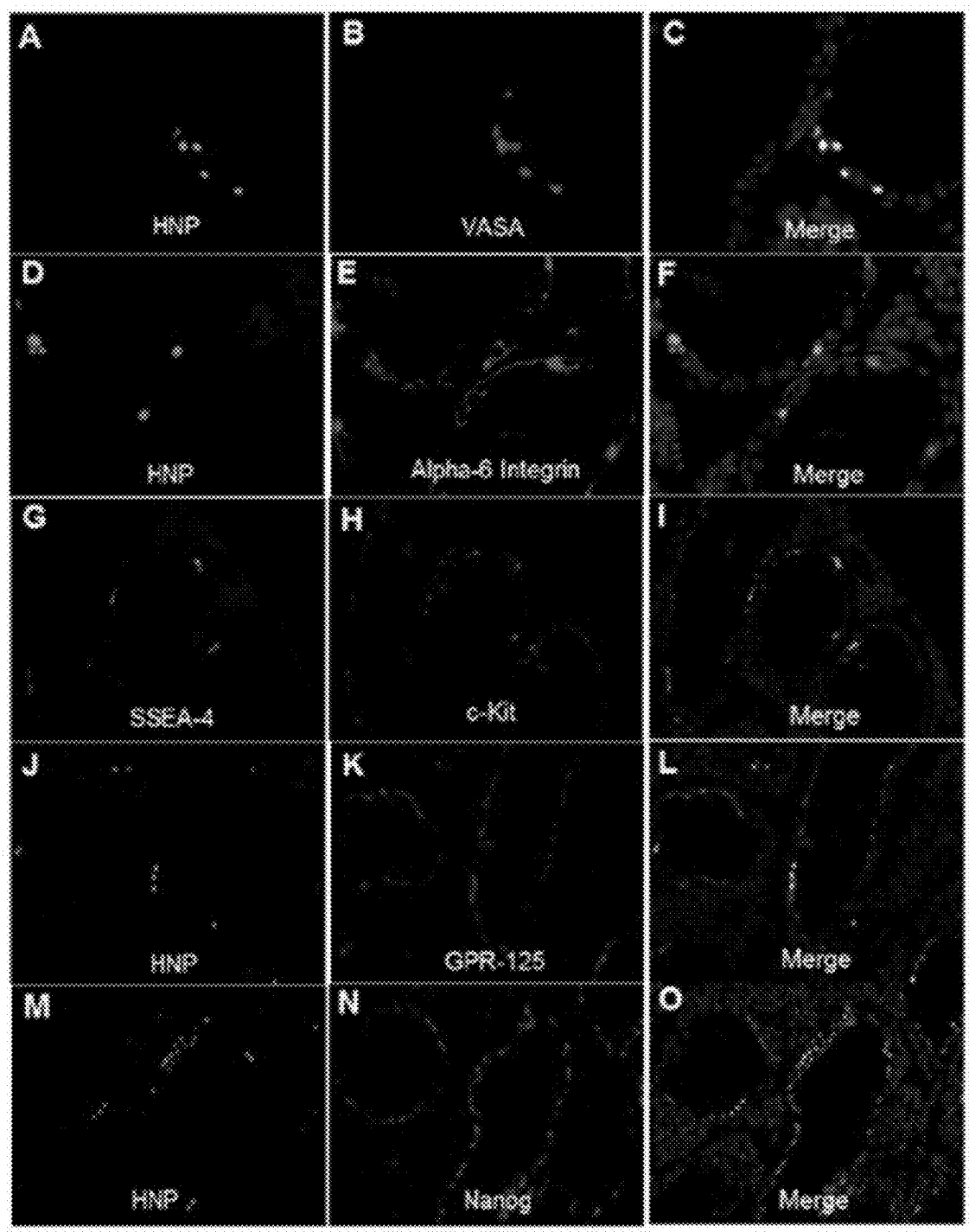
FIG. 42 depicts the expression of specific markers in human spermatogonial stem cells repopulating in the mouse testes. The identity of human cells in the mouse testes was detected by human nuclear protein (HNP) antibody (FIG. 42A). Note all the human cells colonized mouse testes are positively stained for germ cell specific marker VASA (FIG. 42B-C). Some of the human cells at the basement membrane of the mouse testes co-localized CD49f and some were negative for this marker (FIG. 42D-F). Co-localization of SSEA-4 with c-Kit showed that all the SSEA-4+ cells in the mouse testes express c-Kit (FIG. 42G-I). Among human cells colonized in the mouse testes some co-localize with GPR-125 and some are positively stained with pluripotent marker Nanog (FIG. 42J-L). Co-localization of HNP with c-Kit revealed that all the human cells in the mouse testes are c-Kit+ (FIG. 42M-O).
Figure 43:
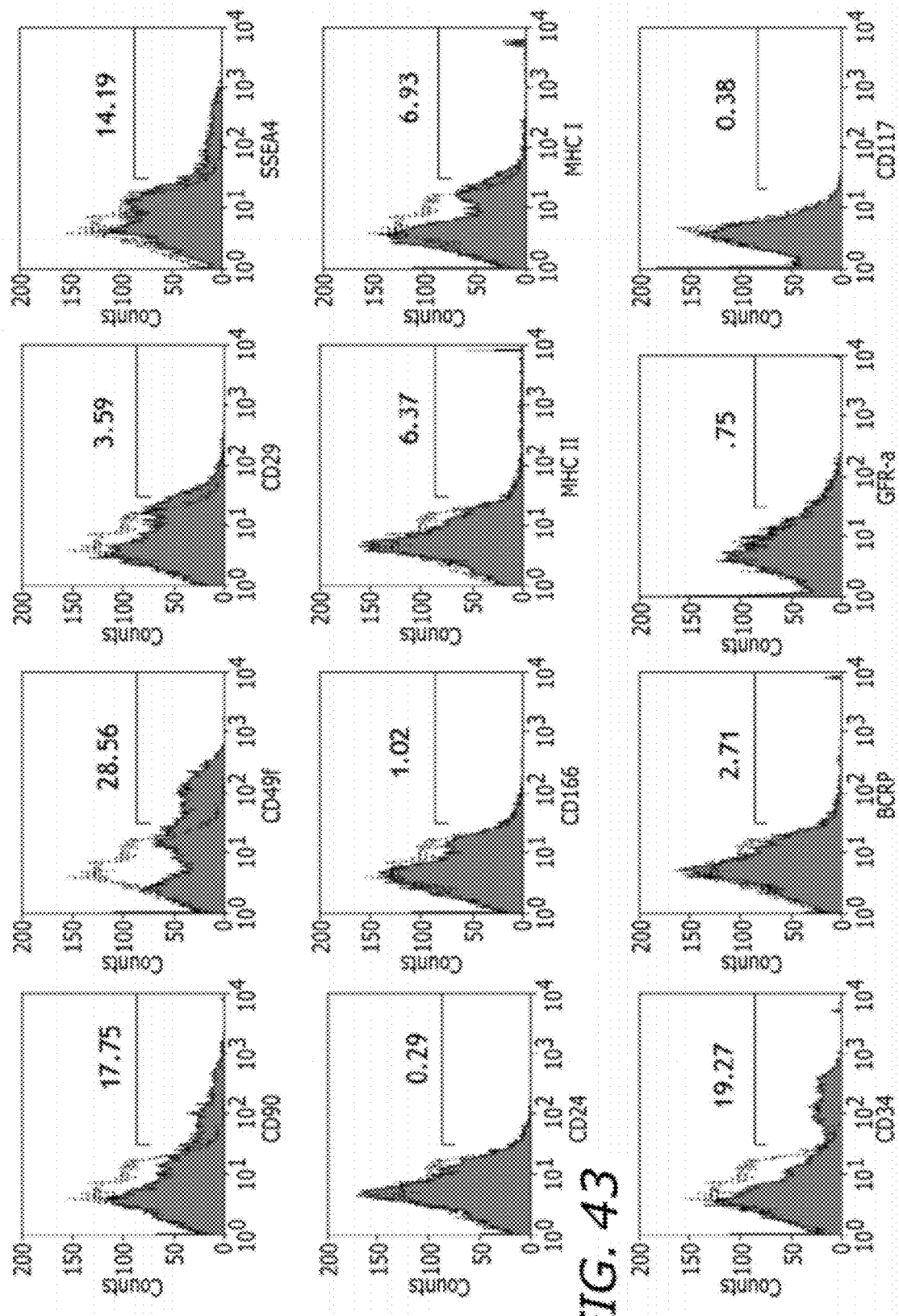
FIG. 43 depicts the expression pattern of cell surface markers used for characterization of human spermatogonial stem cells by flow cytometry. There was a minute amount of cells (1-2%) found in adult human testes expressing GFR-α1, CD24, CD117 and CD166. BCRP, CD29, MHCI and MHCII were moderately (2-5%) expressed in adult human testicular cells. CD90, CD49f, CD34, and SSEA-4 were abundantly found at the surface of cells isolated from adult human testes. The value represents the actual amount of positive cells minus any auto fluorescent events.
Figure 44C:
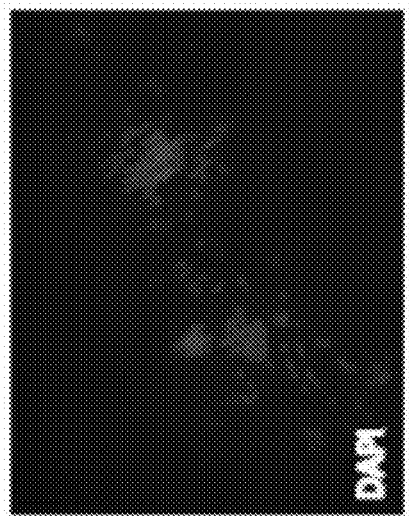
FIG. 44 depicts ex host matured testicular cells by light microscope (FIGS. 44A and F) with H&E staining (FIGS. 44B and D), DAPI staining (FIG. 44C), and PNA staining (FIG. 44E).
FIG. 44G depicts flow cytometry of mouse testicular cells, mouse sperm and ex host matured cells at day 22 of culture.
Figure 44B:
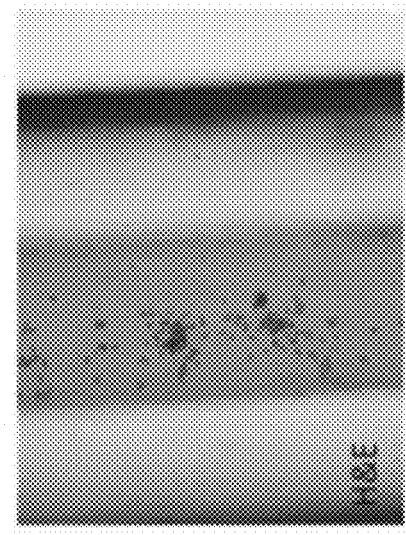
Figure 44A:
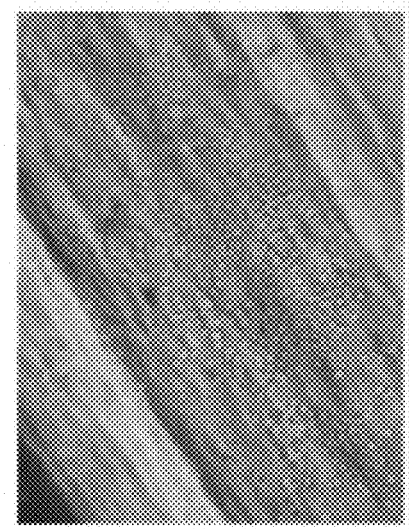
Figure 44F:
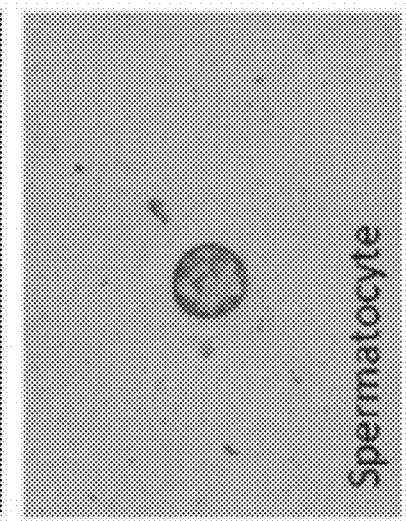
Figure 44E:
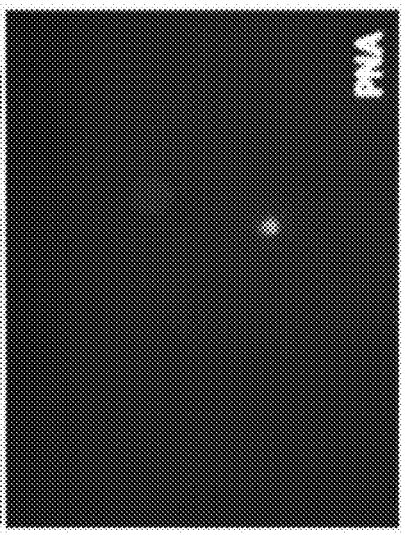
Figure 44D:
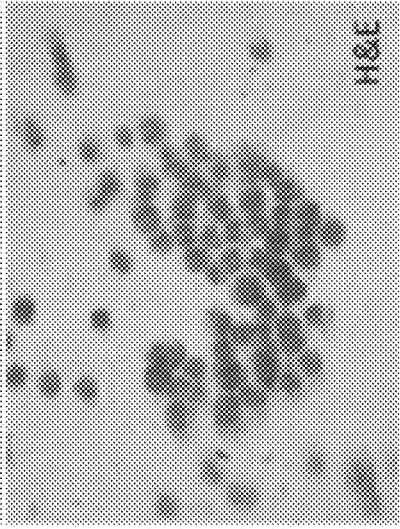
Figure 44G:
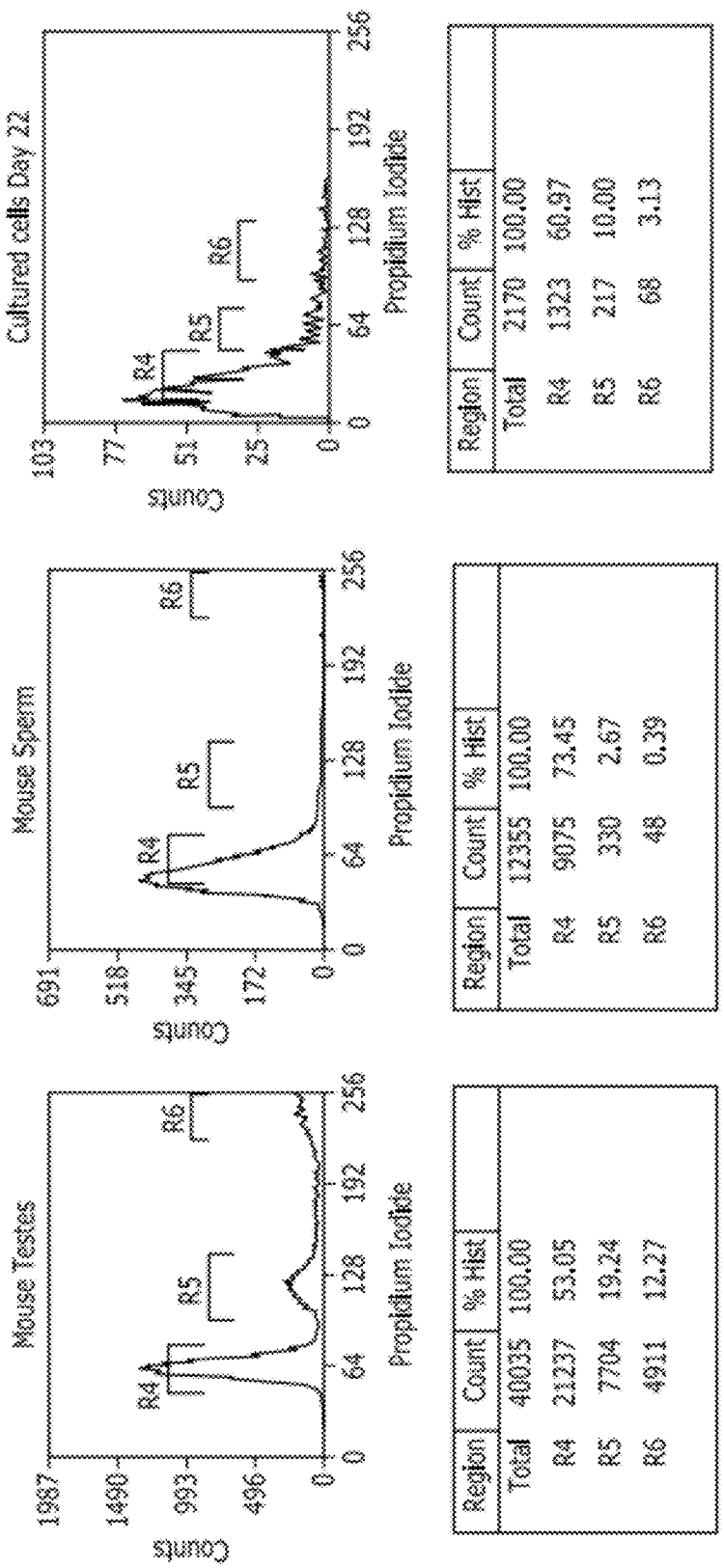

Co-localization studies were done on mouse testes that have been transplanted with enriched population of human spermatogonial stem cells to test their colonization efficiency and unravel markers expressed on the surface of human SSCs repopulating in the mouse testes. Summary of the localization of these markers is presented in Table 12. Using HNP together with SSEA-4, CD49f, and c-Kit, of the cells that are positive for human nuclear protein, 28.1% (±3.6%) are positive for CD49f, 94.9% (±1.3%) are positive for c-Kit, and 14.2% (±3.6%) are positive for SSEA-4. Furthermore, we observed that 100% of the SSEA4+ cells are also positive for c-Kit, further indicating the possibility that only SSEA-4+/c-Kit+ cells can integrate into recipient mouse testes and therefore are the SSCs that are self-renewing among the SSEA-4+ population. Co-localization studies with $\alpha$6-integrin and SSEA-4 have demonstrated that 95.63% (±1.6%) of SSEA-4+ cells are also positive for $\alpha$6-integrin. Considering these results, and the fact that $\alpha$6-integrin co-localizes with HNP, 2-fold more than SSEA-4 and HNP, two populations of $\alpha$6-integrin+ cells, $\alpha$6-integrin+/SSEA4+ and $\alpha$6-integrin+/SSEA-4−, are SSCs that can repopulate the recipient testis. It should also be noted that $\alpha$6-integrin+ cells only account for about a quarter of the integrated cells, meaning that about 75% of the SSCs that have integrated have yet to be characterized with a surface marker by flow cytometry. Although almost all of the integrated cells stain positively for c-Kit, it is localized in the nucleus in most cells and c-Kit+ cells were not found by flow cytometry (FIG. 43). Co-localization of HNP with other cell surface markers revealed that human SSCs colonized in the mouse testes do not express CD-29 ($\beta$1-integrin), a marker that is expressed on the surface of mouse SSCs (FIG. 42). However 42.8% of HNP cells co-localized with GPR-125 indicating this marker is expressed at the surface of a population of repopulating human SSCs. Also, 28.3% of the HNP positive cells co-localized with pluripotent marker Nanog indicating that about one third of repopulating human SSCs might have pluripotent characteristics.

TABLE 12

| Marker | Co-localization with HNP (%) |
|---|---|
| VASA | 100 |
| c-Kit | 49.8 ± 2.9 |
| GPR-125 | 42.8 ± 2.6 |
| LH-R | 0 |
| CD49f | 28.1 ± 3.6 |
| CD29 | 0 |
| SSEA-4 | 14.2 ± 3.6 |
| Nanog | 28.3 ± 1.5 |
| Oct-4 | Not determined |
| Tra-1-60 | 0 |

Discussion

This study clearly demonstrates that spermatogonial stem cells in the adult human testes have phenotypic and molecular characteristics distinct from the mouse and similar but not identical to primate SSCs. First, the localization and expression of selected markers in the human testes sections and isolated cells were studied. Immunohistochemical studies demonstrated that among the markers tested, SSEA-4 is specifically expressed at the surface of human SSCs. All SSEA-4 cells were located at the basement membrane of the seminiferous tubules and co-localized germ cell marker VASA. This is very similar to the previous observations in the adult primate testes. However the percentage of SSEA-4+ cells in the adult human testes was much higher in the human (13%) than the monkey (2%) testes. Molecular biological analysis also revealed that SSEA-4 sorted cells have higher expression level of all the SSC specific genes and a high level of telomerase activity indicating the presence of spermatogonial stem cells in this population. Previous studies showed that SSCs isolated from mouse and adult primate testes express CD49f and CD90 and are negative for CD117. Expression of CD49f and CD90 in isolated human testes cells has already been reported. This immunohistochemical study revealed that CD49f in human testes was localized along the basement membrane of seminiferous tubules suggesting that this marker is expressing in both the SSCs as well as the differentiating type A spermatogonia. Also expression of some CD49f positive cells outside seminiferous tubules indicates that CD49f, although expressed in human SSCs, is not a specific marker and cannot be used alone for enrichment of SSCs from human testes. Flow cytometry analysis confirmed immunohistochemical staining and showed that there are distinct populations of cells within the adult human testes positively stained for CD49f or CD90, however in contrast to primate there was no population of double positive cells present in the human testes. Similar to SSEA-4, the percentage of CD49f+ and CD90+ cells also was much higher in the adult human testes as compared to the monkey testes.

While flow cytometry analysis revealed that there are very few CD117+ cells in the adult human testes, immunohistochemical staining showed localization of c-Kit in many cells at the basement membrane of seminiferous tubules as well as the cells in the luminar compartment of the human testes. A similar localization pattern of c-Kit protein in human testes has been reported by other investigators. Recently it was shown that c-Kit expression in undifferentiated spermatogonia is stage specific indicating involvement of this protein during early stages of human spermatogenesis. C-Kit is a tyrosine kinase membrane protein which is expressed in hematopoietic stem cells and progenitor cells and in several non hematopoietic tissues including gonads. There is a large body of evidence showing the involvement of c-Kit and its ligand stem cell factor (SCF) in a variety of functions during germ cell development including migration and colonization, proliferation and differentiation. Cells in the adult human testes express c-Kit protein in their nucleus and not on their membrane. Nuclear localization of c-Kit might explain why these cells could not be detected by flow cytometry. Although c-Kit is generally a membrane protein, its cytoplasmic and nuclear localization has been reported. Double localization of SSEA-4 with c-Kit showed that there are two populations of SSEA-4+ cells in the adult human testes, one with and the other without c-Kit expression. Based on the studies in the mouse SSCs are shown to be c-Kit negative.

In the adult primate, SSEA-4+ cells are the actively dividing population of spermatogonial stem cells capable of repopulating recipient mouse testes. Human SSCs were purified by SSEA-4 magnetic sorting and SSEA-4+ cells were transplanted into the testes of busulfan treated recipient mouse testes. SSEA-4+ cells were found at the basement membrane of the majority of mouse seminiferous tubules following transplantation indicating the presence of functional SSCs in this population. Surprisingly, all the human cells colonized recipient testes were c-Kit+, indicating that only the c-Kit+ fraction of SSEA-4 sorted cells were able to colonize recipient testes and therefore are the active SSCs in the human testes. RT-PCR analysis also revealed that SSEA-4 sorted cells have a very high expression level of c-Kit and FGFR3. Expression of c-Kit in human SSCs might indicate the involvement of this receptor and its ligand SCF in colonization and/or repopulation of human SSCs. There is a large body of evidence demonstrating that c-Kit and SCF are key regulators of germ cell migration adhesion and proliferation. Also, high expression of FGFR3 in human SSCs might indicates involvement of its ligand in proliferation and self-renewal of human SSCs. Fibroblast growth factors (FGFs) and their receptors (FGFRs) are key signaling molecules for early embryonic and germ cell development. FGFs has been shown to promote survival and maintenance of mouse and human SSCs. In vitro studies showed that FGF9 is a very potent ligand for FGFR3. Therefore addition of FGF9 and SCF to the culture medium of human SSCs might be beneficial for their survival and proliferation in vitro.

Also, a subpopulation of integrated human cells in the mouse testes expressed GPR-125 on their surface, indicating that this marker also is expressed on repopulating human SSCs. Expression of GPR-125 in the mouse and human testes sections has been reported. Subpopulations of repopulating human SSCs in the mouse testes are positively stained for pluripotent marker Nanog. Expression of pluripotent markers Nanog and SSEA-4 in some of the SSCs indicates that subpopulation of the SSCs in the adult human testes might have multipotent ability to differentiate into other cell lineages. Generation of multipotent cell lines from the mouse and human testes supports multipotentiality of human SSCs suggests clinical application of these cells for regenerative diseases other than the restoration of fertility. On the other hand, immunolocalization of Nanog in human testes was not only limited to the undifferentiated SSCs but was also localized in all the germ cells even in the lumen of the seminiferous tubules. This observation is very similar to the adult primate testes suggesting a different role for transcription factor Nanog in the advanced germ cells. The nature of such a role for Nanog is yet to be determined, however it has been reported that pluripotent marker Oct-4 is a survival factor for germ cells and its down regulation will result in apoptosis and cell death rather than differentiation.

The transplantation study also demonstrated niche compatibility between the human and mouse seminiferous tubules for spermatogonial stem cell colonization. Interestingly the percentage of SSEA-4+ (14%) cells and CD49f+ (28%) cells in the recipient mouse testes was very similar to that of the human testes (13% for SSEA-4 and 27% for CD49f) indicating that human SSCs have the ability to colonize and repopulate empty mouse testes at the level very similar to its natural environment suggesting that mouse testes has provided favorable environment for the colonization of human SSCS. However any development further than limited spermatogonial proliferation was not found neither in this study nor in previous studies using bovine, porcine, primate or human SSCs. Although mouse testes cannot provide appropriate environment to support complete spermatogensis from higher species, its basement membrane of seminiferous tubules has the ability to selectively attract and house human spermatogonial stem cells in the manner very similar to the human testes.

In summary, repopulating spermatogonial stem cells in the adult human testes have phenotypic characteristics of SSEA-4+, CD49f+, CD90+, GPR-125+ and c-Kit+. About one third of SSCs express Nanog indicating the existence of populations of spermatogonial stem cells in the adult human testes with pluripotent characteristics. The results have direct implications for isolation and purification of spermatogonial stem cells from adult human testes for clinical applications, culture expansion or differentiation purposes. In addition, expression of pluripotent markers in subpopulations of human SSCs indicates potential application of these cells for cell replacement therapy and tissue regeneration.

Example 13

Ex Host Maturation of Murine Spermatogenic Cells

This study is aimed to investigate whether testicular cells isolated from immature mice can colonize and reconstitute spermatogenesis in artificial somniferous tubules. Medical grade polyethylene tubes (TYGON®, Saint-Gobain Corporation) with the inner diameter of 250 µm and an outer diameter of 300 µm were cut in 10 cm pieces, connected to a 30 gauge needle and used as artificial somniferous tubules. The tubes were washed with 1 ml of 70% ethanol followed by three washes in distilled water and clean air. The tubes were then autoclaved and sealed in sterile bags until use. Extracellular matrix of the testes was extracted from 2 adult mice by decellularization using a mixture of Triton-X-100 and deoxycholate for 24 hr at 37° C. followed by digestion with trypsin and EDTA for 24 hr at 37° C. on a reciprocal shaker. The extracted ECM was solubilized by collagenase (1 mg/ml) for 30 min at 37° C. and the collagenase was then inactivated by adding EDTA. The solubilized ECM was stored at −20° C. in small aliquots. The day before the tubes were to be loaded with cells, they were coated with ECM and incubated at room temperature for 2 hr under ultraviolet light for sterilization and then held at 4° C. until use.

Testes from immature (3-4 days old) GFP or OG2 mice were isolated and loaded in the concentration of $1\text{-}2\times10^4/\mu l$. Approximately 10 µl of cell suspension was needed to fill in each tube. The tubes were then placed in 6 cm dish containing 8 ml of PM-1™ medium supplemented with growth factors including GDNF, FGF, EGF and LIF and cultured at 32° C. in a humidified atmosphere containing 5% $CO_2$. The medium was changed every other day in the tube as well as the 6 cm dish. Culture was continued for 21 days and every day the tubes were examined under the light microscope for topographical examination. After 7 days in culture, maturation inducing factors including FSH (20 ng/ml), SCF (30 ng/ml) and retinoic acid (0.5 µM) were added. After 14 days in culture, GDNF, FGF, EGF and LIF were removed from the culture and the contents of some tubes were flushed by a 1 ml syringe and samples were taken for histological and DNA content analyses. In addition some cells were used for RNA extraction and gene expression analysis. In some experiments, tubes were not coated with ECM and in some other experiments different combinations of maturation inducing factors alone or with other factors like (GNDF, FGF, EGF and LIF) were examined. At the end of the culture period, cells with the morphology of spermatid and sperm were collected and their ability to fertilize eggs was determined by ICSI, or in vitro fertilization (IVF). Furthermore, the ability of the fertilized eggs to develop into embryos was analyzed. Also embryos are tested for the GFP expression and their ability to develop to term was determined after embryo transfer to foster mothers.

Figure 47:
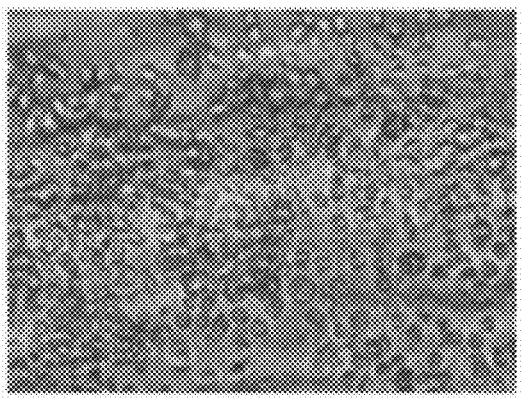
FIG. 47 depicts ex host matured cells with the size and morphology of spermatids.
Figure 48:
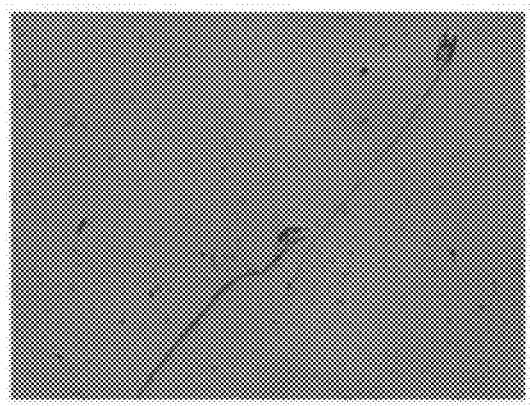
FIG. 48 depict ex host matured testicular cells matured into sperm.

Histological examination of testes sections from a 4 day old OG2 mouse showed that in semniferous tubules, there were only primitive germ cells and immature Sertoli cells and no advanced germ cells were found at this stage of testicular development. Light microscopical examination of the tubes revealed that testes cells attached to the tubes and their number increased during the first week of culture (FIG. 53A). Tubes coated with ECM contained more cells than the non-coated tubes. Germ cell colonies with various sizes were found through out the tube. In some areas colonies were more abundant and even in some parts the cells completely covered the surface of the tubes. H&E and DAPI staining of segments of the tube after day 7 confirmed the light microscopical examination and showed the presence of the colonies and chain of cells within the tube (FIG. 53B-D). Light microscopical examination of the cells collected after 7 and 14 days showed that small cells similar to the morphology of round and elongated spermatids were present. Also some very small cells with condensed nucleus similar to sperm head were found. H&E staining confirmed the presence of cells similar to round spermatids and sperm heads. Immunohistochemical localization of the Peanut Agglutinin (PNA), a lectin that specifically satin acrosome and acrosomal vesicles, showed that round cells and condensed cells express PNA indicating that presence of acrosomal structure in these cells (FIG. 53E). After 18 days in culture more elongated cells were found resembling elongated spermatids (FIG. 47). Also cells with the appearance of mature sperm containing head, acrosome, mid piece and tail were found attached to the dish (FIG. 48). Swimming sperms were found after day 10 in culture and their number increased with the progression of the experiment.

Figure 49A:
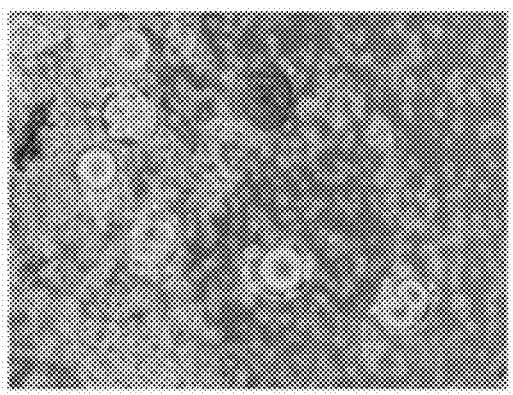
FIG. 49 depicts an in vitro fertilization culture of fertilized eggs formed from ex host matured sperm and normal ova (FIG. 49A) and embryos produced therefrom (FIG. 49B).
Figure 49B:
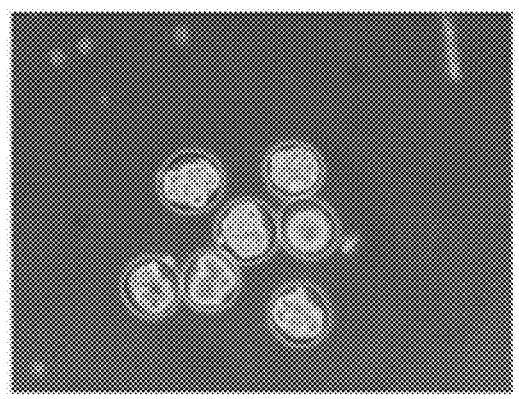

The fertilizing ability of the sperm produced in artificial tubules was tested by an IVF procedure. An 8 weeks old female CD-1 mouse was super ovulated by injections of PMSG (10 IU) followed by HCG (20 IU) after 62 hr of PMSG injection. Twelve hours after HCG, the mouse was sacrificed and eggs were collected and denuded in 0.1% hyaluronidase and transferred to 100 ml of M2 medium under mineral oil. An artificial seminiferous tubule after 22 days of culture was flushed with a 1 ml syringe and the cells were collected and centrifuged at 800×G for 10 min at 4° C. Supernatant was removed and the cells were resuspended in 200 μl of human tubular fluid (HTF) and kept at 32° C. Thirty microliters of the cell suspension collected from the artificial tubule was added to the eggs. After overnight incubation at 37° C., most of the eggs (6/7) were developed to embryos (FIG. 49). The identity of the in vitro produced embryos is determined by GFP PCR.

Artificial tubules coated with adult testes ECM support maturation of spermatogenic cells. Cells with the morphology and characteristics of spermatocytes were found indicating that many cells entered meiosis after 5-7 days of culture. Also cells with the morphology of round spermatids and elongated spermatids were found indicating that some of the germ cells entered spermiogenesis. While nuclear condensation occurred in most of the cells, elongation was not completed and delayed. Eventually some cells with the morphology of the mature sperm were formed. These cells contained all the characteristics of a fully mature spermatozoa including a clear condensed head, acrosome, mid piece and tail. Sperm produced in artificial tubes fertilized eggs by in vitro fertilization, indicating that these cells have the ability to swim to the egg, bind to the zona pellucida, penetrate the zona and fuse with oolema, and finally were able to activate the eggs to produce embryos.

Example 14

Ex Host Maturation of Murine Ovarian Germline Cells

Ovarian germline stem cells (OGSC) derived from mouse ovary can produce oocyte-like cells with the diameter of 40-60 μm which resemble primary oocytes. These cells are further matured by follicle engineering using granulosa cells followed by in vitro development of the follicles or by transplantation of the follicles into ovariectomized mice mice—ex host/in vivo maturation.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Certain embodiments of this invention are described herein, including the best mode known to the inventors for carrying out the invention. Of course, variations on those embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are individually incorporated herein by reference in their entirety.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method for maturing prepubertal germline cells into haploid gametes ex host comprising:

culturing testicular cells obtained from a prepubertal subject in vitro in artificial seminiferous tubules disposed within a cell culture medium and wherein said testicular cells comprise germline stem cells, Leydig cells, Sertoli cells, and peritubular cells, wherein said culturing causes maturation of said germline cells into functional sperm.

2. The method of claim 1 wherein said prepubertal testicular cells are cryopreserved prior to maturation.

3. The method of claim 1 wherein said culturing comprises culture of immature testicular germline cells in the presence of at least one growth promoting factor selected from the group consisting of glial cell line-derived growth factor, fibroblast growth factor, leukemia inhibitor factor and epidermal growth factor.

4. The method of claim 1 wherein said culturing comprises culture of immature testicular germline cells in the presence of at least one maturation-inducing factor selected from the group consisting of follicle stimulating hormone, stem cell factor and retinoic acid.

5. The method of claim 1 wherein said artificial seminiferous tubules comprise biocompatible tubing coated with extracellular matrix.

6. The method of claim 5 wherein said extracellular matrix is testicular extracellular matrix.

7. The method of claim 6 wherein said testicular extracellular matrix is from the same subject as said testicular germline cells.

* * * * *

SEQUENCE LISTING

```
<160> NUMBER OF SEQ ID NOS: 16

<210> SEQ ID NO 1
<211> LENGTH: 38
<212> TYPE: DNA
<213> ORGANISM: Artificial Sequence
<220> FEATURE:
<223> OTHER INFORMATION: 5' c-Kit primer

<400> SEQUENCE: 1
aggtgacact atagaatagc acggttgaat gtaaggct                                38

<210> SEQ ID NO 2
<211> LENGTH: 38
<212> TYPE: DNA
<213> ORGANISM: Artificial Sequence
<220> FEATURE:
<223> OTHER INFORMATION: 3' c-Kit primer

<400> SEQUENCE: 2
aggtgacact atagaatagc acggttgaat gtaaggct                                38

<210> SEQ ID NO 3
<211> LENGTH: 38
<212> TYPE: DNA
<213> ORGANISM: Artificial Sequence
<220> FEATURE:
<223> OTHER INFORMATION: 5' GFRalpha1 primer

<400> SEQUENCE: 3
aggtgacact atagaatatc agcaagtgga gcacattc                                38

<210> SEQ ID NO 4
<211> LENGTH: 39
<212> TYPE: DNA
<213> ORGANISM: Artificial Sequence
<220> FEATURE:
<223> OTHER INFORMATION: 3' GFRalpha1 primer

<400> SEQUENCE: 4
gtacgactca ctatagggaa gcattccgta gctgtgctt                               39

<210> SEQ ID NO 5
<211> LENGTH: 39
<212> TYPE: DNA
<213> ORGANISM: Artificial Sequence
<220> FEATURE:
<223> OTHER INFORMATION: 5' PLZF primer

<400> SEQUENCE: 5
aggtgaccac tatagaatat tcatccagag ggagctgtt                               39

<210> SEQ ID NO 6
<211> LENGTH: 39
<212> TYPE: DNA
<213> ORGANISM: Artificial Sequence
<220> FEATURE:
<223> OTHER INFORMATION: 3' PLZF primer

<400> SEQUENCE: 6
ctacgactca ctatagggac ctcgttatca ggaagctcg                               39

<210> SEQ ID NO 7
<211> LENGTH: 38
<212> TYPE: DNA
<213> ORGANISM: Artificial Sequence
```

```
<220> FEATURE:
<223> OTHER INFORMATION: 5' c-Ret primer

<400> SEQUENCE: 7
aggtgacact atagaataac attgcccagc aacttagg                              38

<210> SEQ ID NO 8
<211> LENGTH: 39
<212> TYPE: DNA
<213> ORGANISM: Artificial Sequence
<220> FEATURE:
<223> OTHER INFORMATION: 3' c-Ret primer

<400> SEQUENCE: 8
gtacgactca ctatagggag gtggctcctt tctcaactg                             39

<210> SEQ ID NO 9
<211> LENGTH: 38
<212> TYPE: DNA
<213> ORGANISM: Artificial Sequence
<220> FEATURE:
<223> OTHER INFORMATION: 5' GPR125 primer

<400> SEQUENCE: 9
aggtgacact atagaatact tggcgcagat gtgataga                              38

<210> SEQ ID NO 10
<211> LENGTH: 39
<212> TYPE: DNA
<213> ORGANISM: Artificial Sequence
<220> FEATURE:
<223> OTHER INFORMATION: 3' GRP125 primer

<400> SEQUENCE: 10
gtacgactca ctatagggag aaaagttggc tgcttccac                             39

<210> SEQ ID NO 11
<211> LENGTH: 38
<212> TYPE: DNA
<213> ORGANISM: Artificial Sequence
<220> FEATURE:
<223> OTHER INFORMATION: 5' Dppa5 primer

<400> SEQUENCE: 11
aggtgacact atagaataga aagttcccga agacctga                              38

<210> SEQ ID NO 12
<211> LENGTH: 39
<212> TYPE: DNA
<213> ORGANISM: Artificial Sequence
<220> FEATURE:
<223> OTHER INFORMATION: 3' Dppa5 primer

<400> SEQUENCE: 12
gtacgactca ctatagggaa ctggagcatc cacttggtc                             39

<210> SEQ ID NO 13
<211> LENGTH: 39
<212> TYPE: DNA
<213> ORGANISM: Artificial Sequence
<220> FEATURE:
<223> OTHER INFORMATION: 5' FGFR3 primer

<400> SEQUENCE: 13
aggtgacact atagaatatg ggttttctca tcactctgc                             39
```

```
<210> SEQ ID NO 14
<211> LENGTH: 39
<212> TYPE: DNA
<213> ORGANISM: Artificial Sequence
<220> FEATURE:
<223> OTHER INFORMATION: 3' FGFR3 primer

<400> SEQUENCE: 14
gtacgactca ctatagggag ttggactcca gggacacct                    39

<210> SEQ ID NO 15
<211> LENGTH: 38
<212> TYPE: DNA
<213> ORGANISM: Artificial Sequence
<220> FEATURE:
<223> OTHER INFORMATION: 5' hTERT primer

<400> SEQUENCE: 15
aggtgacact atagaatatt gtcaaggtgg atgtgacg                     38

<210> SEQ ID NO 16
<211> LENGTH: 39
<212> TYPE: DNA
<213> ORGANISM: Artificial Sequence
<220> FEATURE:
<223> OTHER INFORMATION: 3' hTERT primer

<400> SEQUENCE: 16
gtacgactca ctatagggag gctggaggtc tgtcaaggt                    39
```